US011167104B2

(12) United States Patent
Hammer et al.

(10) Patent No.: US 11,167,104 B2
(45) Date of Patent: Nov. 9, 2021

(54) THERMOFORMED MASK

(71) Applicant: Fisher & Paykel Healthcare Limited, Auckland (NZ)

(72) Inventors: Jeroen Hammer, Auckland (NZ); Adam Alexander Tebbutt, Auckland (NZ); Andrew Chun Mon Fan, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/474,520

(22) PCT Filed: Dec. 29, 2017

(86) PCT No.: PCT/NZ2017/050179
§ 371 (c)(1),
(2) Date: Jun. 27, 2019

(87) PCT Pub. No.: WO2018/124889
PCT Pub. Date: Jul. 5, 2018

(65) Prior Publication Data
US 2021/0100969 A1 Apr. 8, 2021

Related U.S. Application Data

(60) Provisional application No. 62/441,036, filed on Dec. 30, 2016.

(51) Int. Cl.
*A61M 16/06* (2006.01)
(52) U.S. Cl.
CPC .... *A61M 16/0622* (2014.02); *A61M 16/0694* (2014.02); *A61M 2205/0216* (2013.01)

(58) Field of Classification Search
CPC ............ A61M 16/06–0694; A61M 2205/0216
See application file for complete search history.

(56) References Cited

U.S. PATENT DOCUMENTS

| 3,815,596 A | * | 6/1974 | Keener | A61M 16/06 128/205.17 |
| 10,357,626 B1 | * | 7/2019 | Baker | A61M 16/06 |
| 2005/0005940 A1 | * | 1/2005 | Gunaratnam | A61M 16/0683 128/206.27 |

(Continued)

FOREIGN PATENT DOCUMENTS

| WO | WO 2015/193408 | 12/2015 |
| WO | WO 2018/124889 | 7/2018 |

OTHER PUBLICATIONS

International Search Report and Written Opinion for PCT/NZ2017/050179 dated May 25, 2018 in 17 pages.

*Primary Examiner* — Valerie L Woodward
(74) *Attorney, Agent, or Firm* — Knobbe, Martens, Olson & Bear, LLP

(57) ABSTRACT

Respiratory masks made of thermoformed EVA foam are provided. A mask can include a seal that contacts a user's face in use and a housing permanently joined to the seal. Both the seal and housing can be made of EVA foam. The seal and housing can be made of EVA foam having different densities. The mask can further include a frame removably or permanently coupled the housing. Headgear can be coupled to the frame and can couple the mask to the user's face in use.

14 Claims, 73 Drawing Sheets

(56) References Cited

U.S. PATENT DOCUMENTS

| | | | |
|---|---|---|---|
| 2011/0005524 A1* | 1/2011 | Veliss | A61M 16/0655 128/206.24 |
| 2011/0146684 A1* | 6/2011 | Wells | A61M 16/0605 128/205.25 |
| 2012/0080035 A1* | 4/2012 | Guney | A61M 16/0611 128/205.25 |
| 2012/0204879 A1* | 8/2012 | Cariola | A61M 16/0655 128/206.24 |
| 2012/0204881 A1* | 8/2012 | Davidson | A61M 16/0683 128/206.25 |
| 2013/0139822 A1 | 6/2013 | Gibson et al. | |
| 2014/0150799 A1 | 6/2014 | Daly | |
| 2014/0158136 A1 | 6/2014 | Romagnoli et al. | |
| 2014/0216462 A1* | 8/2014 | Law | A61M 16/0616 128/205.25 |
| 2016/0271350 A1 | 9/2016 | Lang et al. | |
| 2016/0279371 A1 | 9/2016 | Dravitzki et al. | |

* cited by examiner

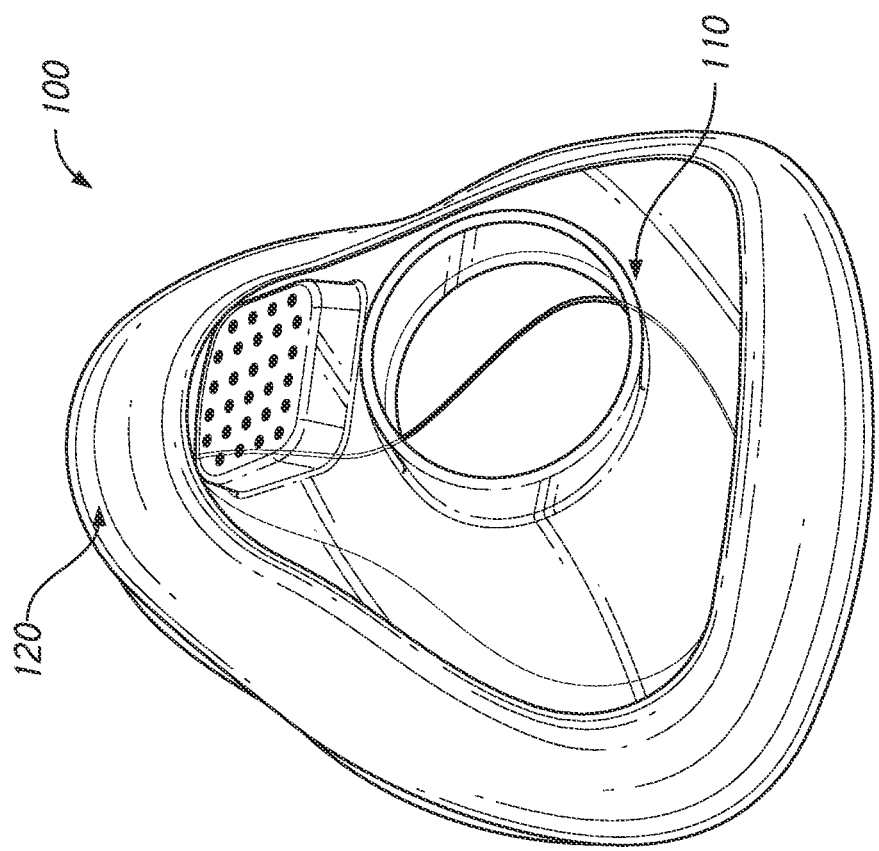
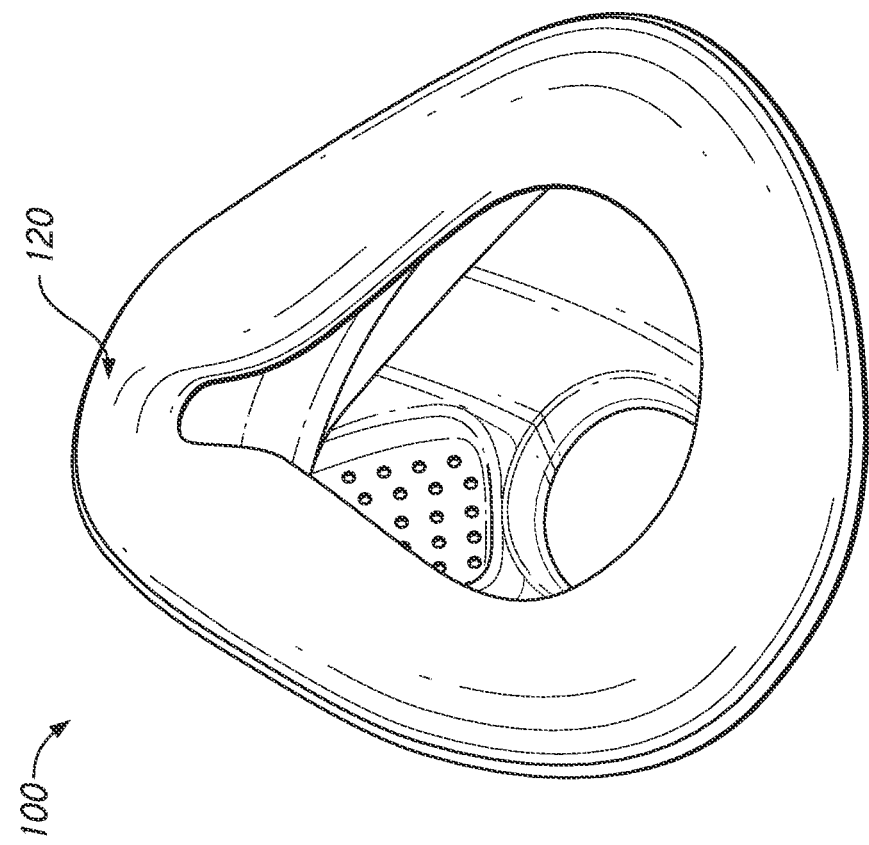
FIG. 1

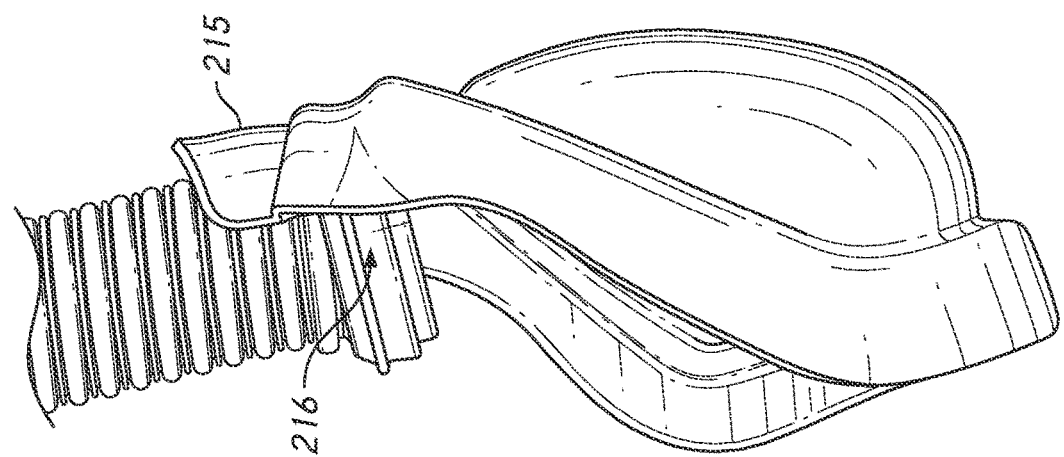
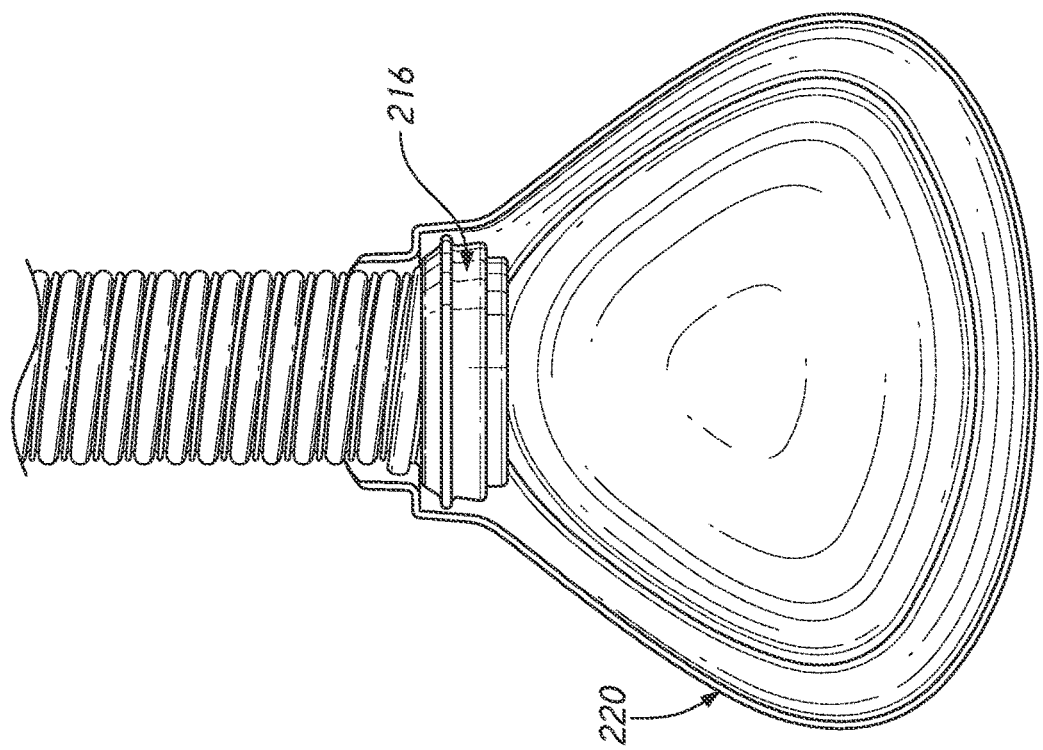
FIG. 9B
FIG. 9A

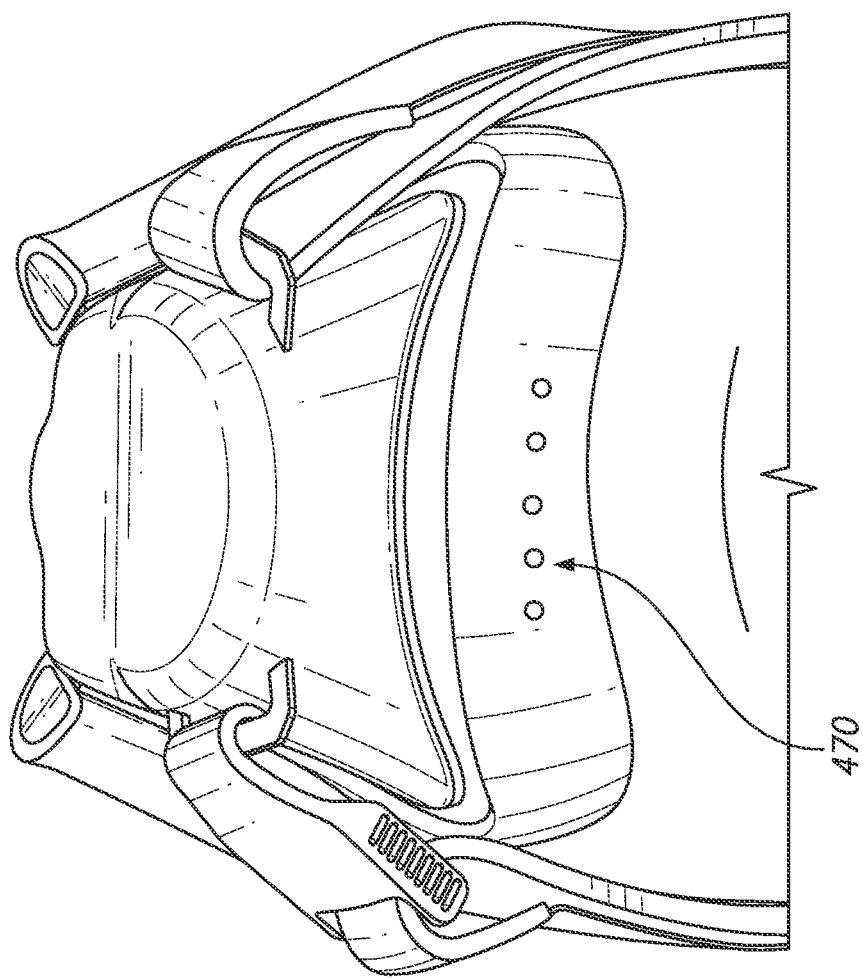

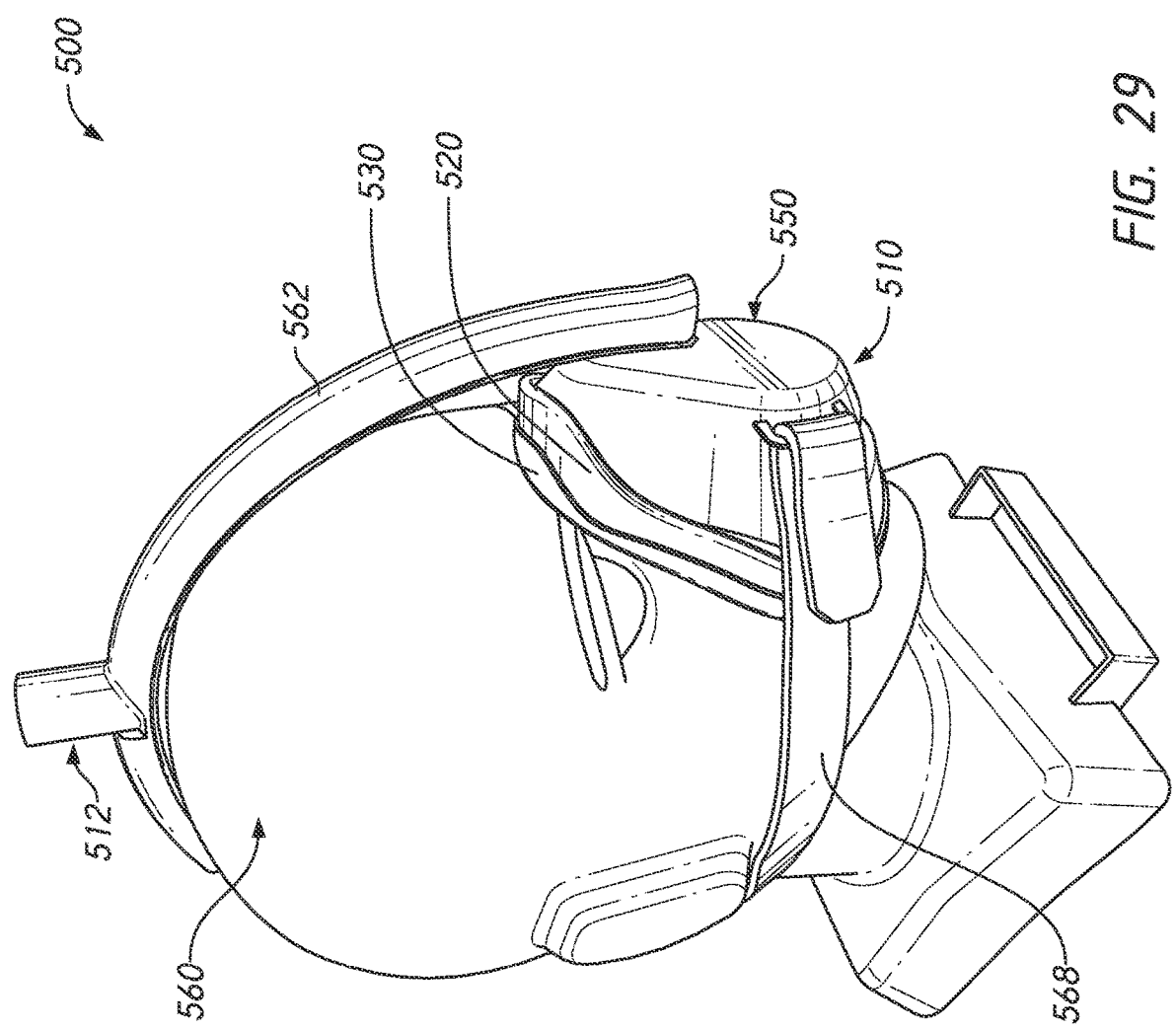

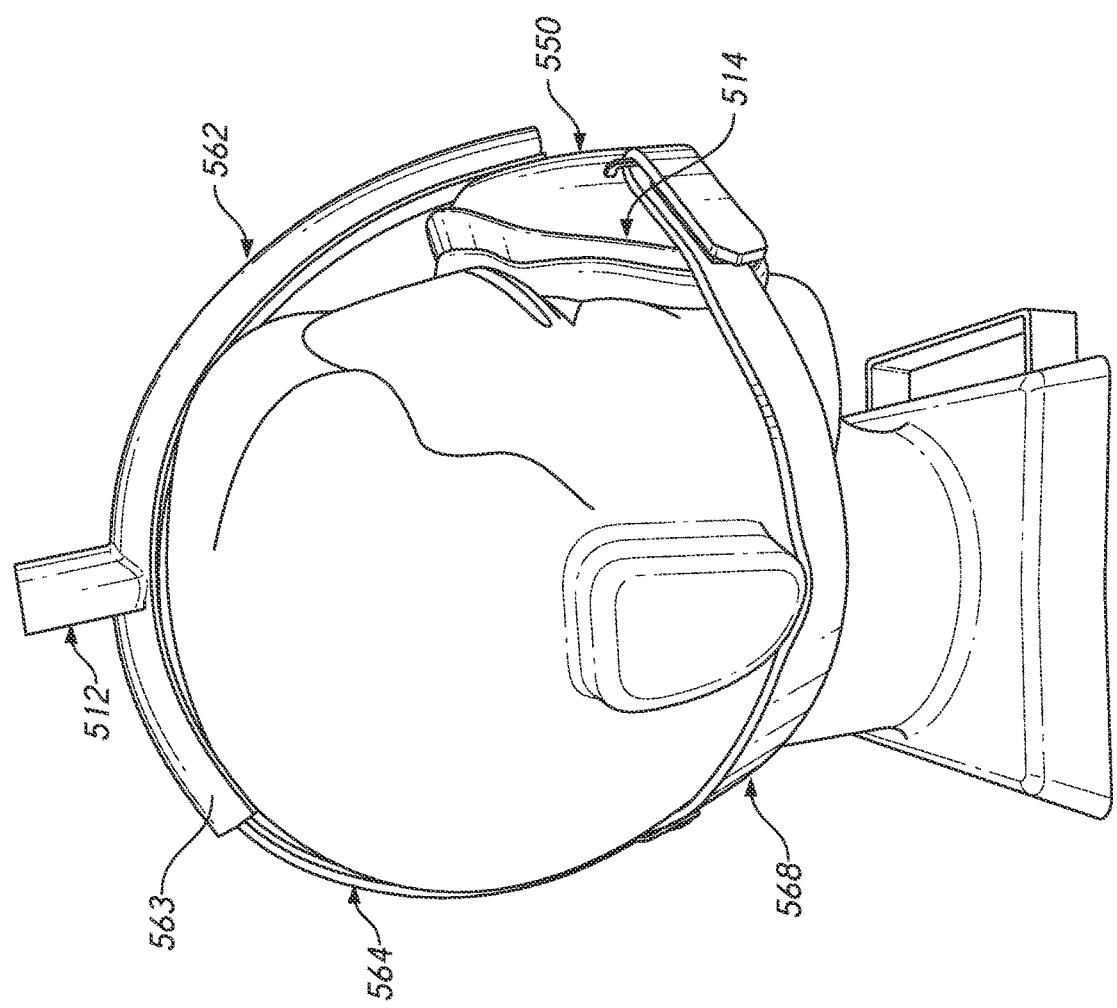

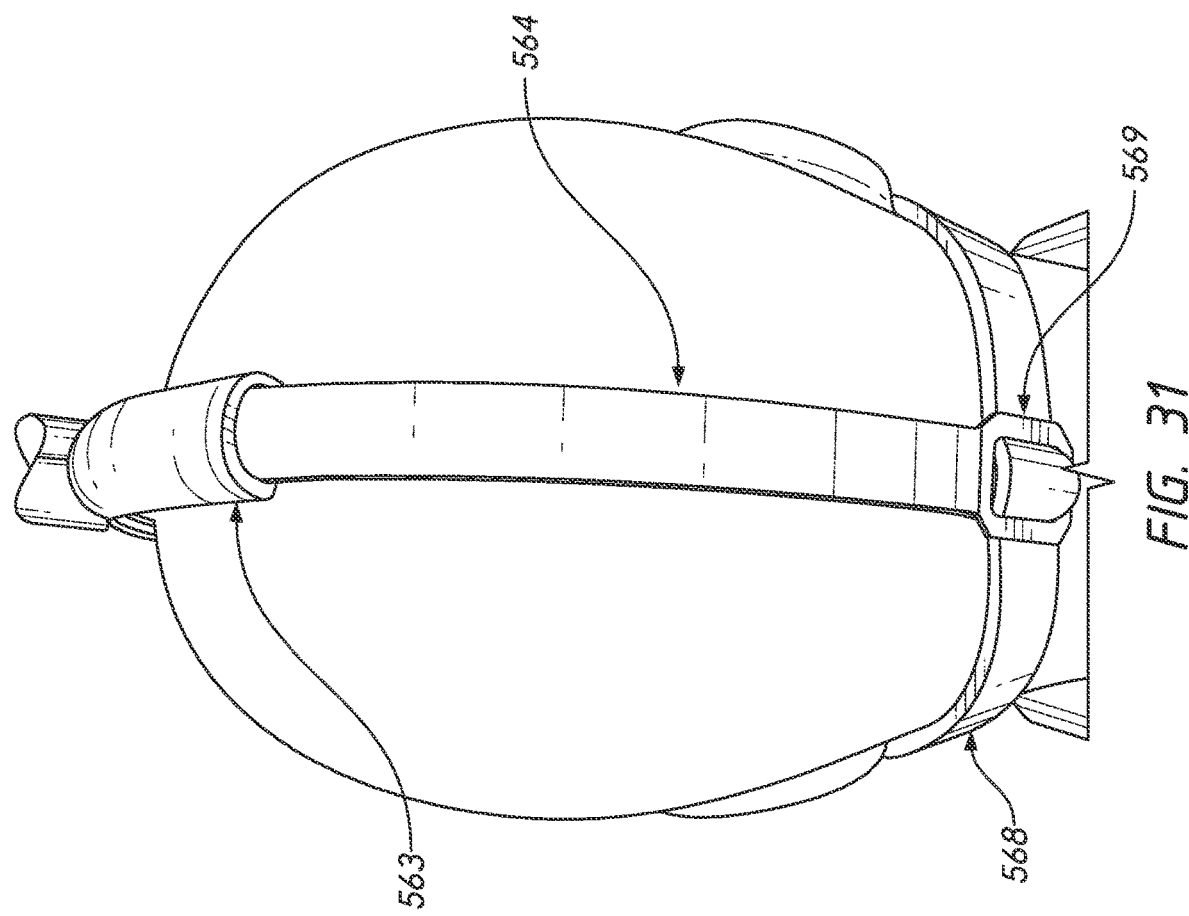

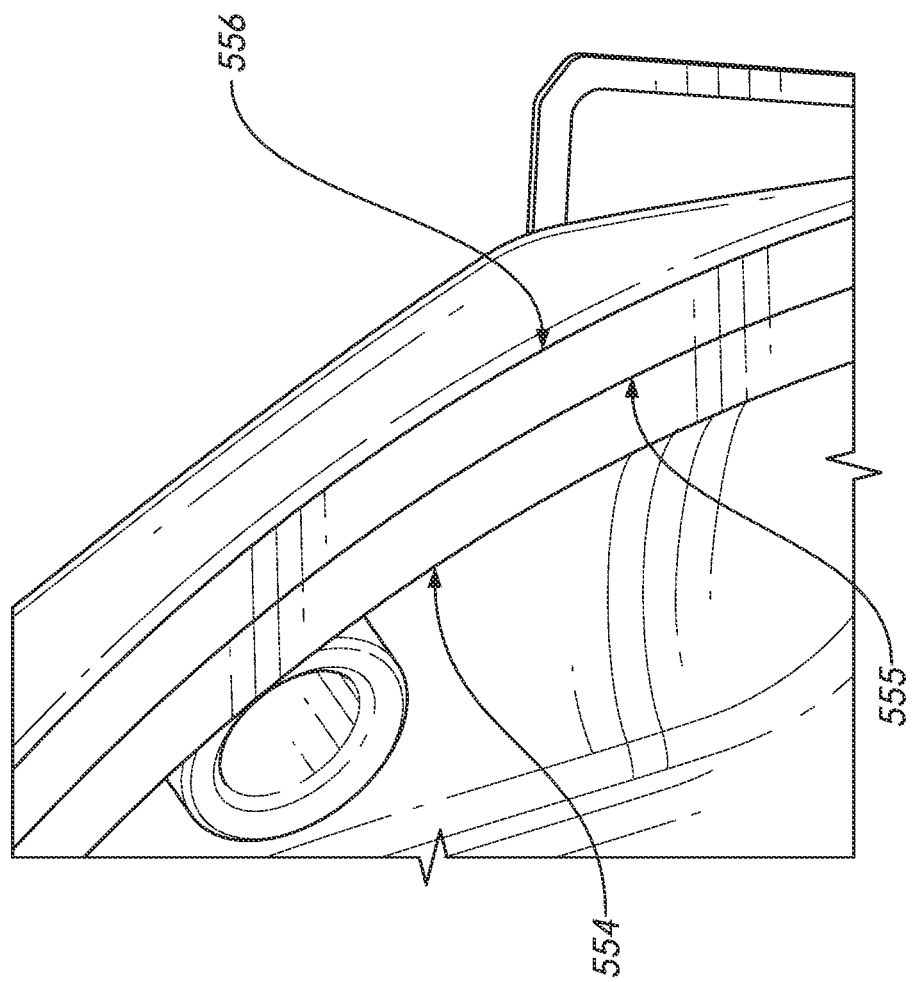

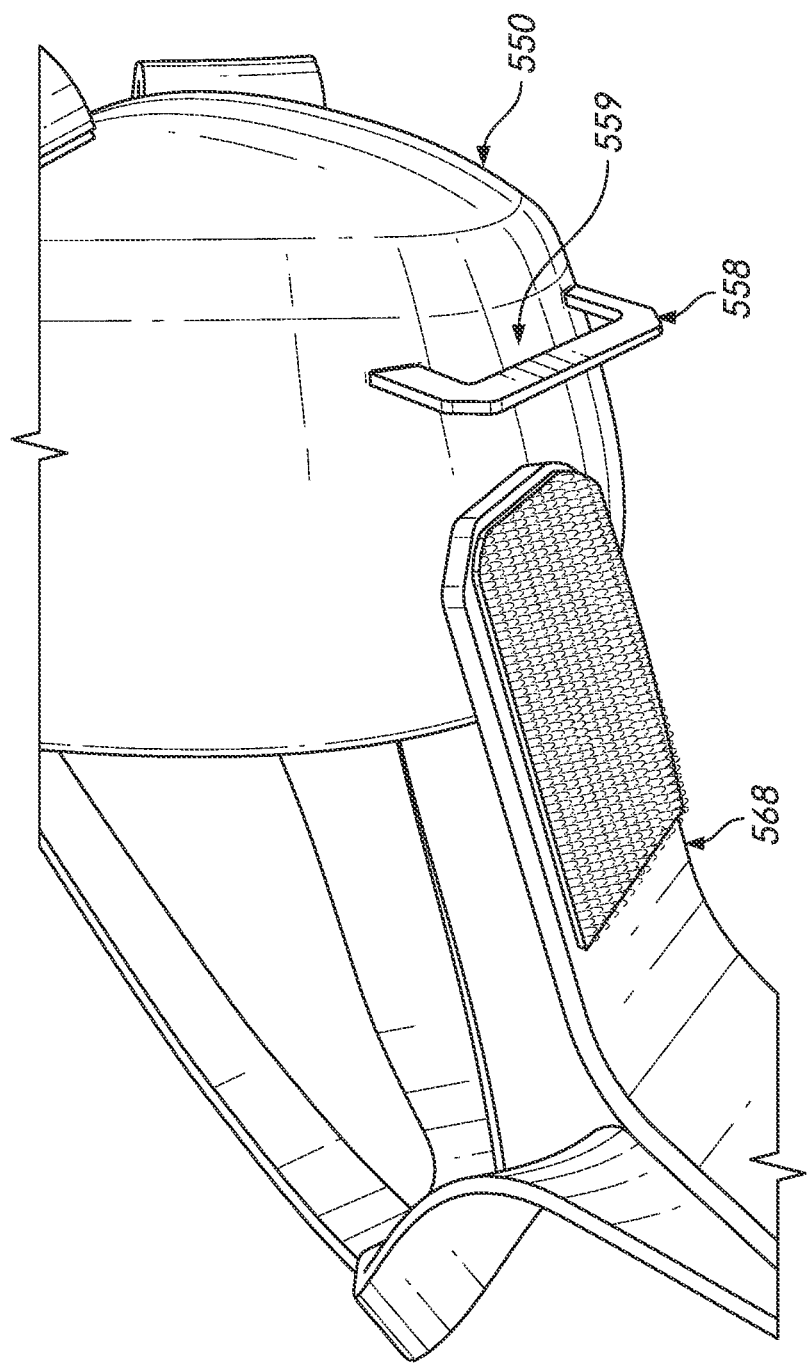

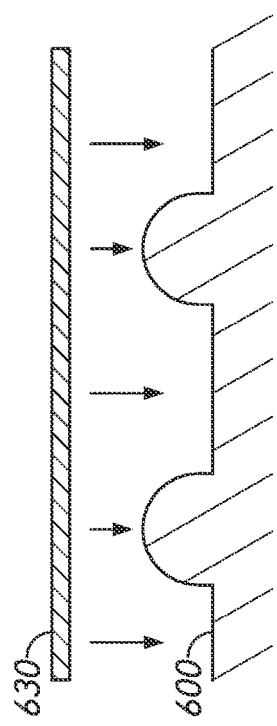
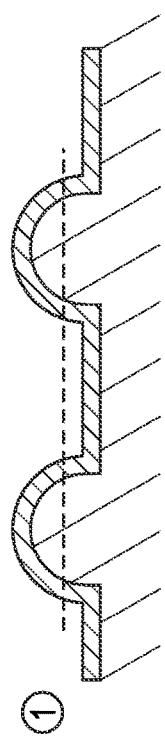
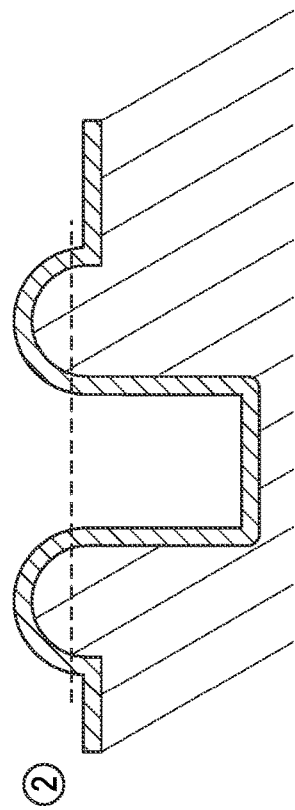
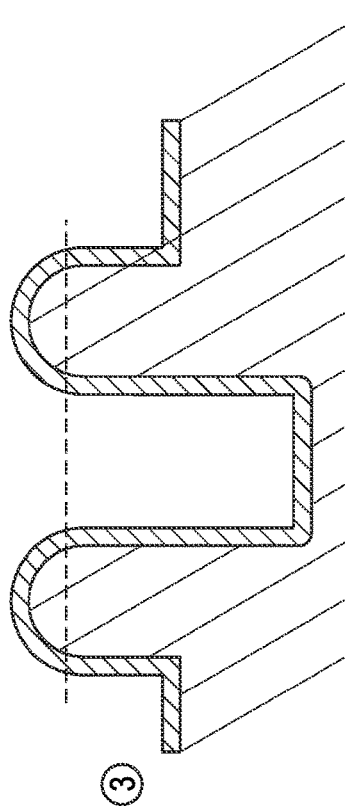
FIG. 42A
FIG. 42B
FIG. 42C
FIG. 42D

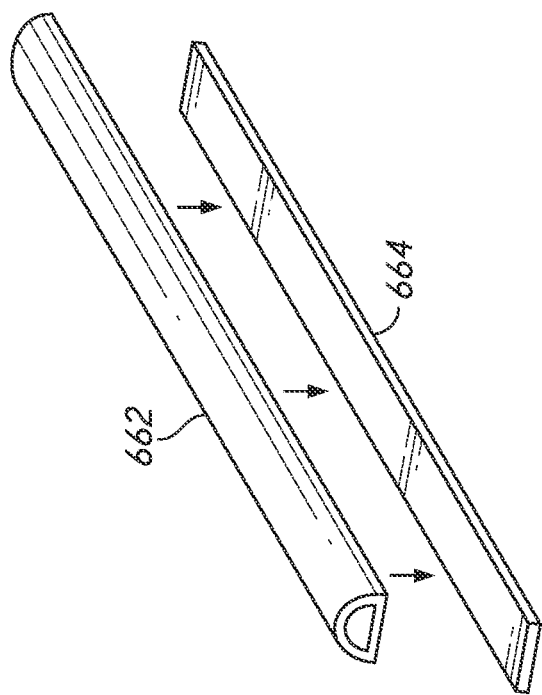
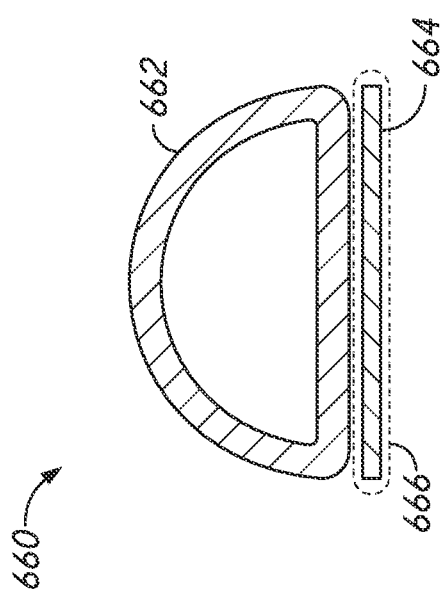
FIG. 43B
FIG. 43A

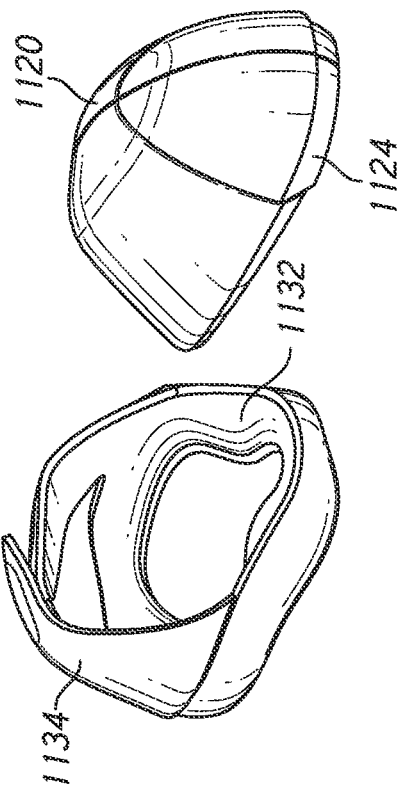
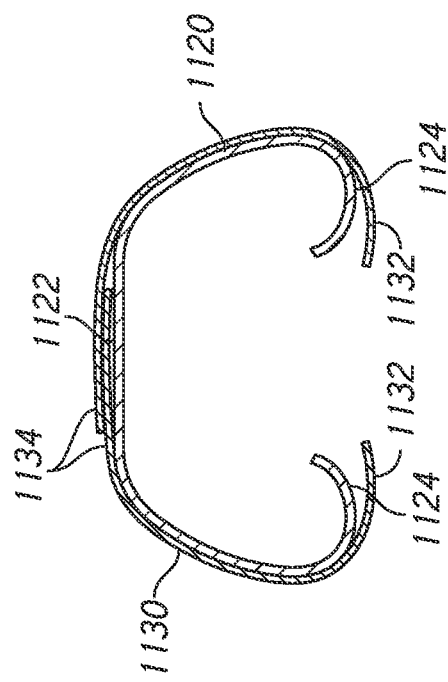
FIG. 73     FIG. 74
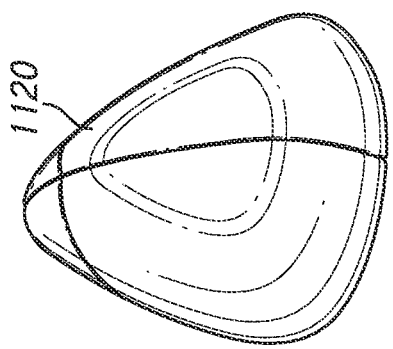
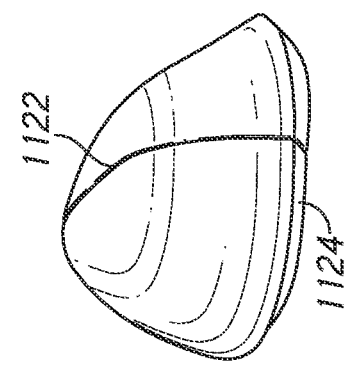
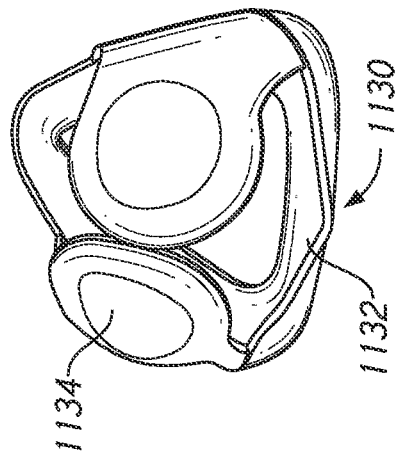
FIG. 75     FIG. 76

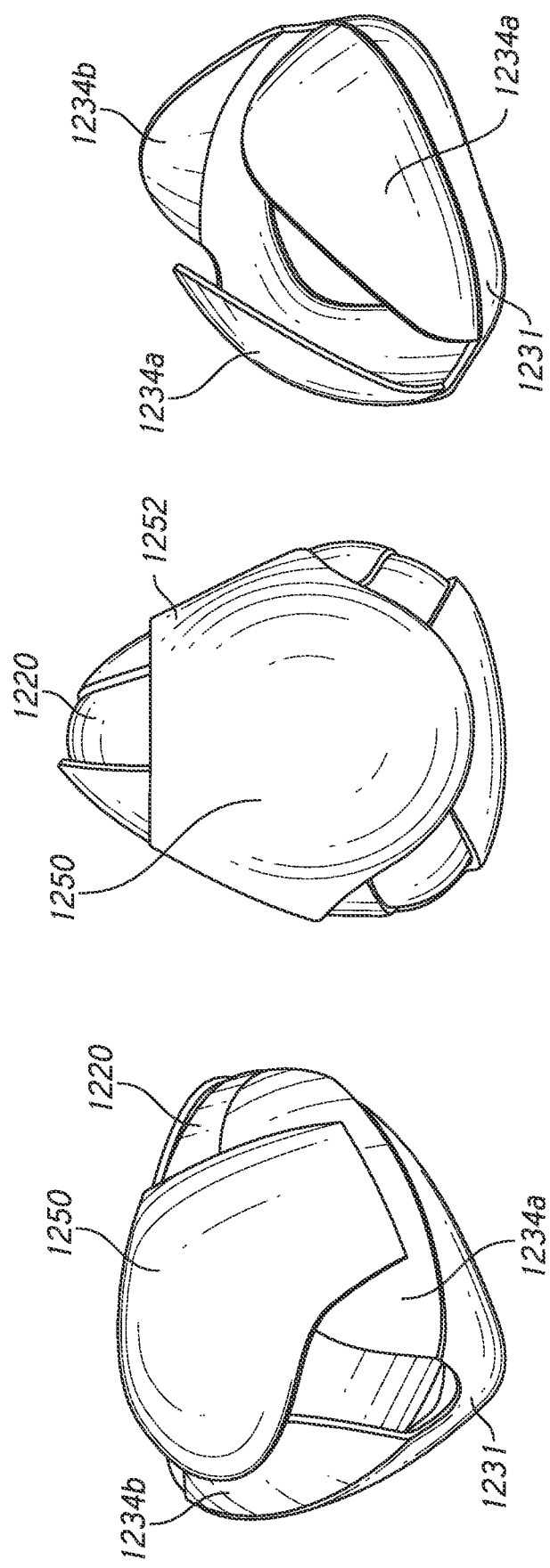

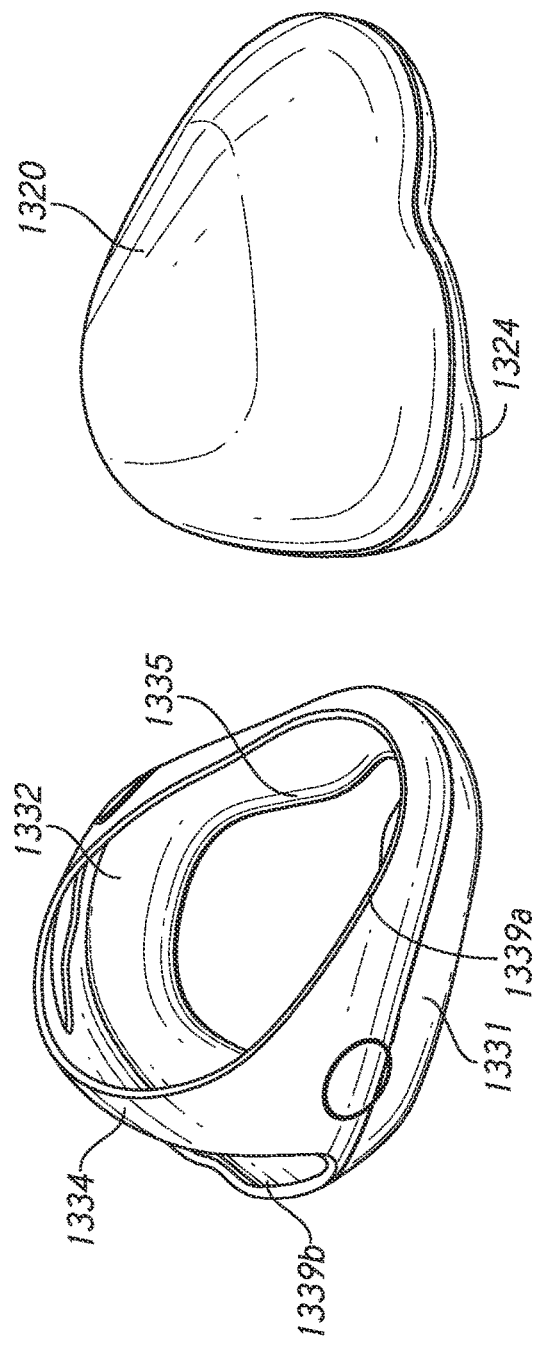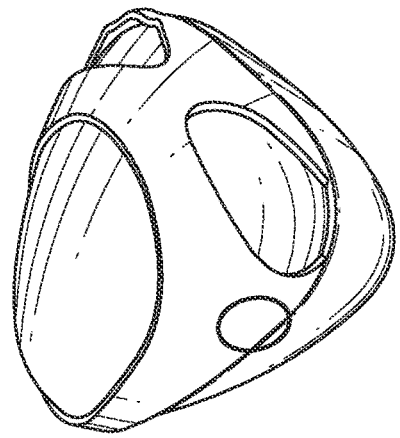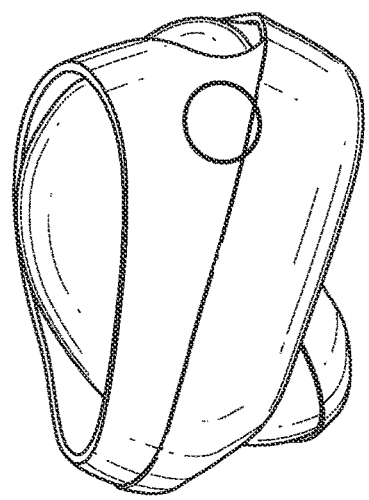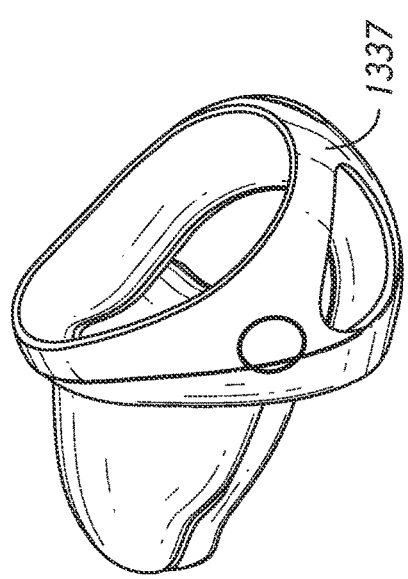
FIG. 94
FIG. 97
FIG. 96
FIG. 95

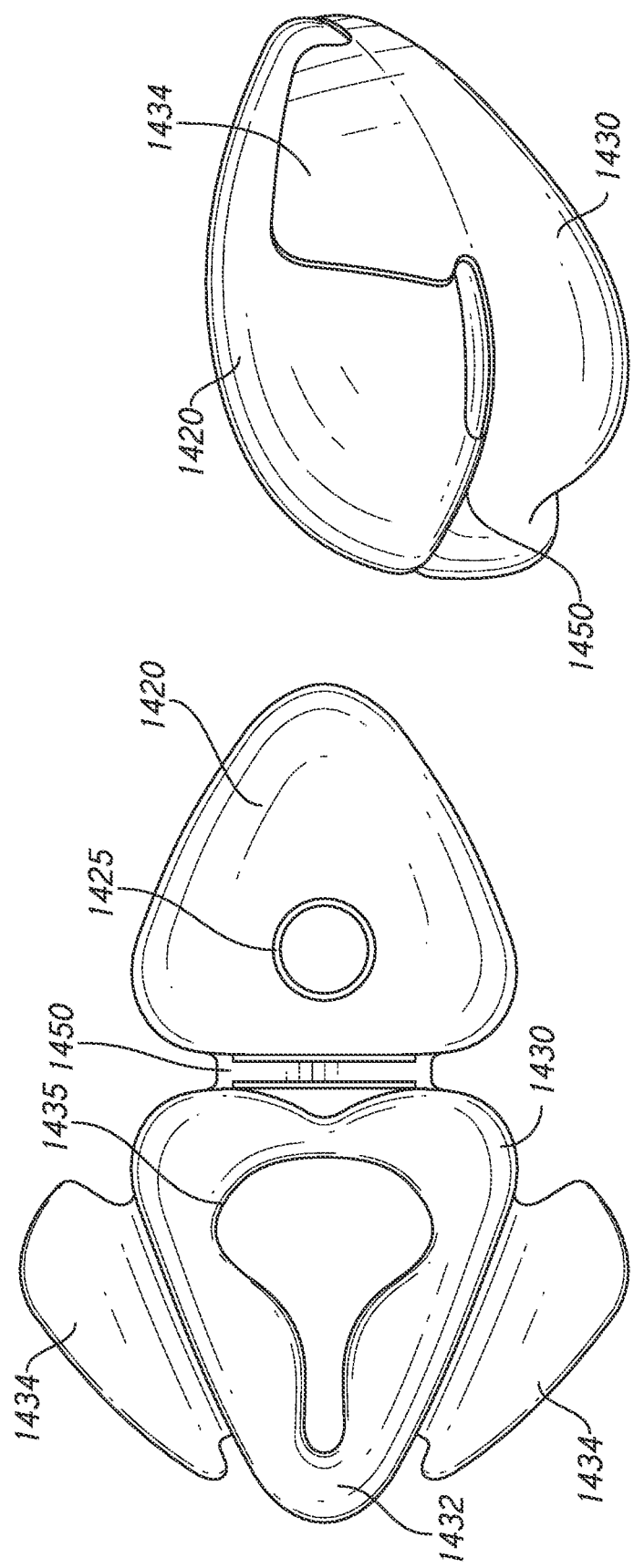

THERMOFORMED MASK

INCORPORATION BY REFERENCE TO PRIORITY APPLICATIONS

The present application claims priority benefit of U.S. Provisional Application No. 62/441,036, filed Dec. 30, 2016, which is hereby incorporated by reference herein.

BACKGROUND

Field

The present disclosure generally relates to a respiratory mask system for the delivery of respiratory therapy to a patient. More particularly, the present disclosure relates to various components of a respiratory mask system.

Description of the Related Art

Respiratory masks are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnea (OSA), a condition in which a patient's airway intermittently collapses, during sleep, preventing the patient from breathing for a period of time. The cessation of breathing, or apnea, results in the patient awakening. Repetitive and frequent apneas may result in the patient rarely achieving a full and restorative night's sleep.

CPAP therapy involves the delivery of a supply of continuous positive air pressure to the airway of the patient via a respiratory mask. The continuous positive pressure acts as a splint within the patient's airway, which supports the airway in an open position such that the patient's breathing and sleep are not interrupted.

Respiratory masks typically comprise a patient interface and a headgear, wherein the patient interface is configured to deliver the supply of continuous positive air pressure to the patient's airway via a seal or cushion that, in some cases, forms an airtight seal in or around the patient's nose and/or mouth. Respiratory masks are available in a range of styles including full-face, nasal, direct nasal and oral masks, which create an airtight seal with the nose and/or mouth. The seal or cushion is held in place on the patient's face by the headgear. In order to maintain an airtight seal the headgear should provide support to the patient interface such that it is held in a stable position relative to the patient's face during use. Such respiratory masks may also be used to deliver NIV and other therapies.

SUMMARY

The systems, methods and devices described herein have innovative aspects, no single one of which is indispensable or solely responsible for their desirable attributes. Without limiting the scope of the claims, some of the advantageous features will now be summarized.

In some embodiments, a respiratory mask assembly includes a cushion module that includes a seal portion, a housing, and an inlet aperture. The seal portion includes a thermoformed foam. The housing in some embodiments includes a thermoformed foam. The seal portion and housing are permanently joined to define a breathing chamber. The inlet aperture has a front portion defined by the housing and a back portion defined by the seal portion.

In some embodiments, a respiratory mask assembly includes a cushion module that includes a seal portion, a housing, and a frame. The seal portion includes a thermoformed foam. The housing includes a thermoformed foam. The seal portion and housing are permanently joined to define a breathing chamber. The frame includes a thermoformed foam. The frame is configured to connect to a headgear assembly and is configured to releasably connect to the housing. In some such embodiments, the frame includes a first component of a hook and loop fastener, the housing comprises a second component of the hook and loop fastener, and the frame is configured to releasably connect to the housing via the first and second components of the hook and loop fastener.

In some embodiments, a respiratory mask assembly includes a cushion module that includes a seal portion and a housing. The seal portion includes a thermoformed foam and has a first joining flange extending radially from a distal perimeter of the seal portion. The housing includes a thermoformed foam and has a second joining flange extending radially from a proximal perimeter of the housing. The first and second joining flanges are permanently joined such that the seal portion and housing define a breathing chamber. At least one of the first and second joining flanges includes an aperture configured to receive a component of a headgear assembly.

In some embodiments, a headgear assembly for a respiratory mask includes two side straps, a top strap, and a telescopic adjustment mechanism. Each of the two side straps is configured to couple to a lateral side of a respiratory mask and configured to extend below a user's ear in use. The top strap extends between the two side straps and is configured to extend over the top of the user's head in a front to back direction in use. The top strap includes an air path configured to deliver a supply of gases to the respiratory mask in use. The telescopic adjustment mechanism is configured to allow for adjustment of a length of the top strap. In some such embodiments, the side straps are rotatably coupled to the respiratory mask.

In some embodiments, a respiratory mask assembly includes a cushion module, a frame, and a headgear assembly. The cushion module includes a seal portion including thermoformed foam and a housing including thermoformed foam. The seal portion and the housing are permanently joined to define a breathing chamber. The frame includes thermoformed foam and is configured to connect to the housing. The headgear assembly is configured to connect to the frame. The headgear assembly includes two side straps and a top strap. Each of the two side straps is configured to pass across one of the user's cheeks and above one of the user's ears in use. The top strap extends between the two side straps and is configured to extend across a top of the user's head in use. An air conduit extends within the top strap and the side straps, and the air conduit is configured to provide a supply of gases to the breathing chamber of the cushion module. In some such embodiments, the air conduit is rotatably coupled to the cushion module. In some embodiments, the frame does not form part of an air path from the headgear assembly to the breathing chamber.

In some embodiments, a respiratory mask assembly includes a cushion module and a frame. The cushion module includes a seal portion including thermoformed foam and a housing including thermoformed foam. The seal portion and the housing are permanently joined to define a breathing chamber. The housing includes a gusset inwardly offset from an outer perimeter of the housing. The frame includes thermoformed foam and is configured to connect to the housing and a headgear assembly.

In some embodiments, a method of forming a component of a respiratory mask includes vacuum thermoforming a sheet of EVA foam over a mold. A thickness of the component depends at least in part on a draw depth of the sheet of EVA foam during vacuum thermoforming.

In some embodiments, a cushion module for a respiratory mask includes a housing and a seal coupled to the housing in use. The housing can include thermoformed foam. The seal can include thermoformed foam. The seal includes a retention portion configured to removably retain the housing in engagement with the seal to form a breathing chamber.

The retention portion can be configured to overlap at least a portion of the housing when the seal and the housing are coupled. The retention portion can be inwardly concave relative to the cushion module.

The retention portion can include a pair of arms, each arm extending forwardly and inwardly from a lateral side of the seal. In some embodiments, the arms overlap each other. The housing can include an inlet aperture. In such embodiments, each arm can include an aperture proximate a free end of the arm, and the apertures of the arms are configured to align with the inlet aperture when the seal and the housing are coupled. A bushing, swivel, elbow, or air supply conduit can extend through the apertures in the arms and the inlet aperture to secure the arms relative to the housing.

In some embodiments, the retention portion includes a belt extending from a first lateral side of the seal to an opposing second lateral side of the seal. The belt can be tethered to a lower portion of the seal.

In some embodiments, the retention portion includes a pair of opposing arms extending from upper lateral sides of the seal. In some such embodiments, the arms can be substantially triangular.

In some embodiments, the cushion module further includes a retention cover coupled to the housing and configured to overlap at least a portion of the retention portion of the seal. The retention cover can include thermoformed foam. The retention cover can be coupled to the housing by a bushing.

In some embodiments, a cushion module for a respiratory mask includes a housing and a seal formed from a single sheet of foam. In some embodiments, the seal and the housing are joined by a living hinge. The seal can include a retention portion configured to retain the housing relative to the seal to form a breathing chamber.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 1 illustrates an example embodiment of a mask having a thermoformed EVA seal portion;

FIG. 9A illustrates a rear view of the air conduit and a housing or shell of the mask of FIG. 4;

FIG. 9B illustrates a side view of the air conduit and shell of FIG. 9A;

FIG. 27 illustrates a bottom view of an alternative embodiment of the mask of FIG. 23;

FIG. 29 illustrates a perspective view of an example embodiment of a mask assembly including thermoformed EVA components coupled to a user's face;

FIG. 30 illustrates a side view of the mask assembly of FIG. 29;

FIG. 31 illustrates a rear view of the mask assembly of FIG. 29;

FIG. 35 illustrates a close up view of an edge of the frame of FIG. 34;

FIG. 36 illustrates a close up view of a headgear connector of the frame of FIG. 34;

FIG. 42A illustrates a schematic of an EVA foam sheet being applied to a mold for vacuum thermoforming;

FIG. 42B-42D illustrate variations in mask component thickness due to variations in draw depths during vacuum thermoforming;

FIG. 43A illustrates a schematic cross-section of a headgear component including an air passageway or conduit;

FIG. 43B illustrates an exploded view of the headgear component of FIG. 43A;

FIG. 73 illustrates a front view of the seal and housing of the cushion module of FIG. 71 decoupled from each other;

FIG. 74 illustrates a top-side perspective view of the decoupled seal and housing of FIG. 73;

FIG. 75 illustrates a bottom view of the decoupled seal and housing of FIG. 73;

FIG. 76 illustrates a schematic cross-section of the cushion module of FIG. 71;

FIG. 83 illustrates a front-side-bottom perspective view of an example embodiment of a cushion module including a seal and housing removably coupled to each other and a retention cover;

FIG. 84 illustrates a front view of the cushion module of FIG. 83;

FIG. 85 illustrates a rear-top-side perspective view of the seal of the cushion module of FIG. 83;

FIG. 94 illustrates a front-top-side perspective view of the seal and housing of the cushion module of FIG. 92 decoupled from each other;

FIGS. 95-97 illustrate a method of coupling the seal and housing of the cushion module of FIG. 92;

FIG. 98 illustrates an example embodiment of a cushion module including an integrally formed seal and housing in an expanded configuration;

FIG. 99 illustrates the cushion module of FIG. 98 in a folded or coupled configuration;

DETAILED DESCRIPTION

Figure 2:
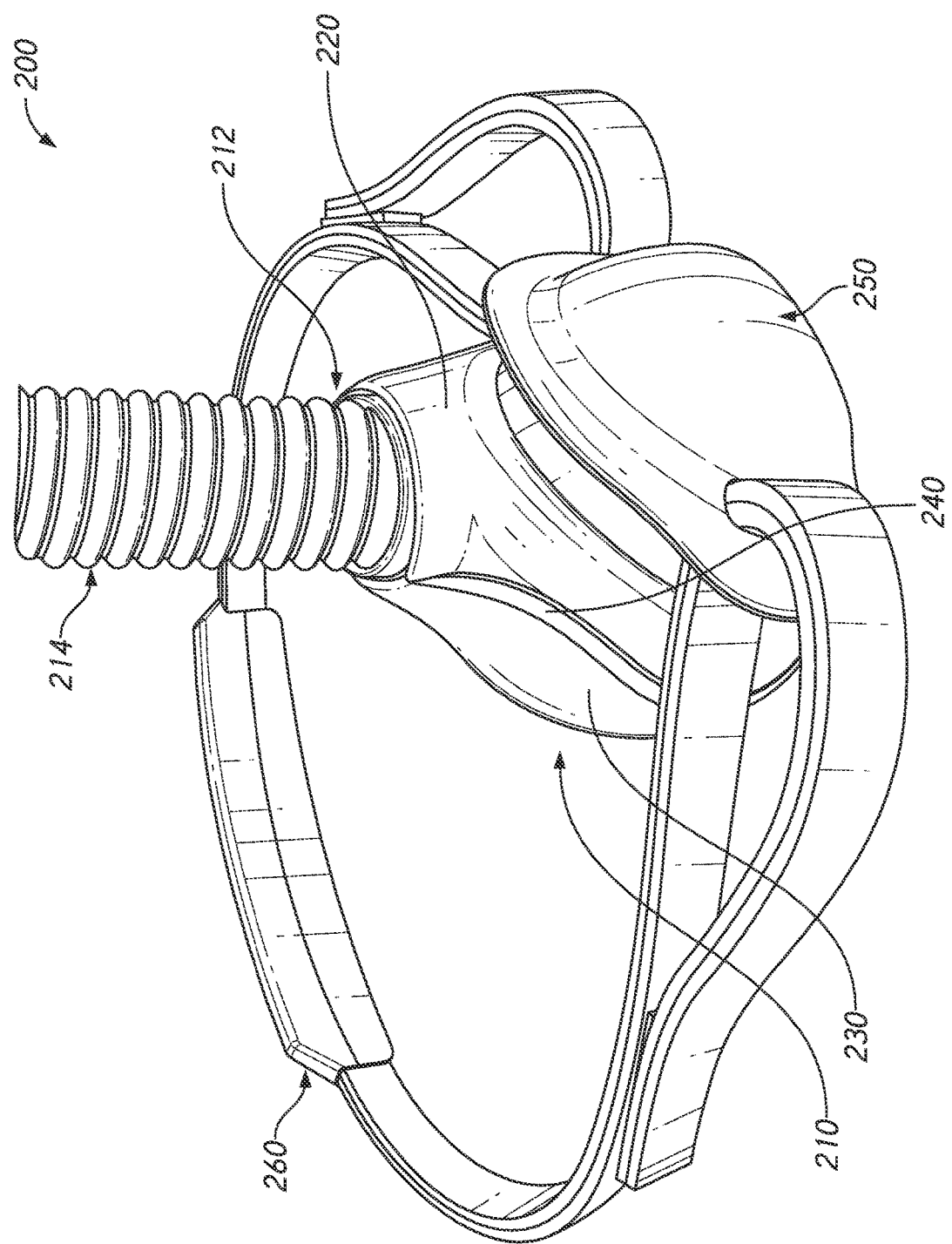
FIG. 2 illustrates a perspective view of an example embodiment of a mask assembly including thermoformed EVA components.
Figure 3:
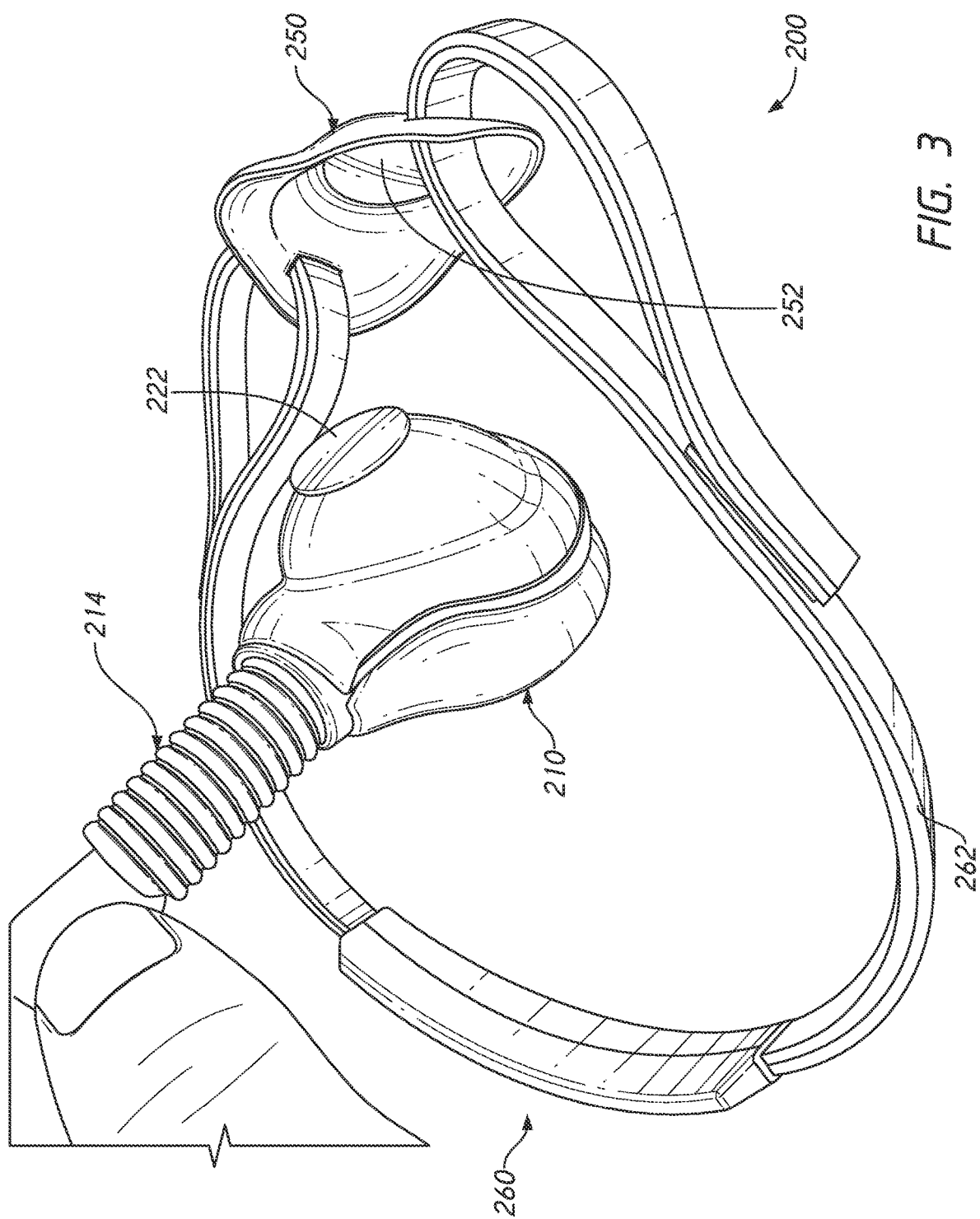
FIG. 3 illustrates a partially exploded view of the mask assembly of FIG. 2.
Figure 4:
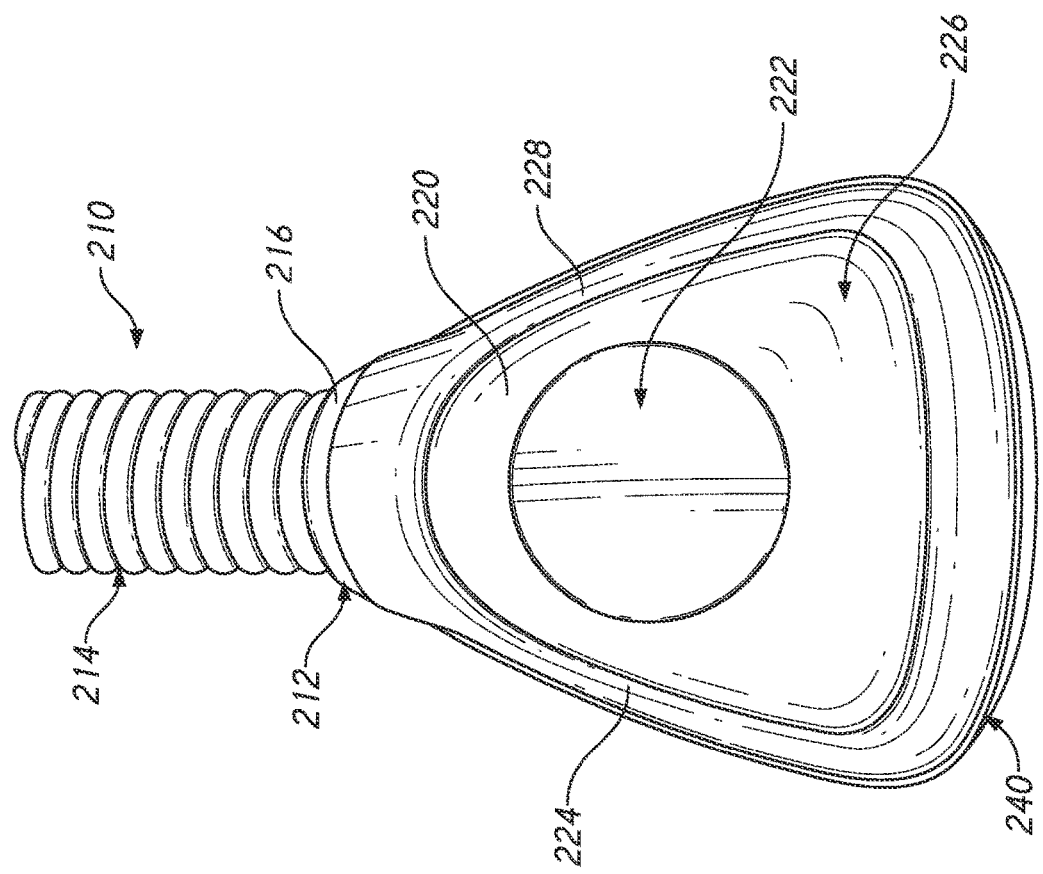
FIG. 4 illustrates a front view of a mask and air conduit of the mask assembly of FIG. 2.

Embodiments of systems, components, and/or methods of assembly, manufacture, and/or use will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Mask systems currently available typically include a shell or housing made of hard plastic(s) such as polycarbonate and a seal or cushion made of silicone, elastomer(s), and/or gel based material(s). In some cases, these materials can look and/or feel sterile or medical, which may reduce patient acceptance and compliance. Such mask systems can be relatively heavy and rigid, and therefore require relatively high forces applied by headgear to create a seal with a user's face in use. These high forces can cause pressure points that can cause discomfort and sometimes damage to the user's skin. A mask system according to the present disclosure can include one or more components made of foam, for example, thermoformed EVA (ethylene-vinyl acetate) foam, closed cell foam sheet materials, polyethylene, or other foam materials. Where EVA foam may be specifically referenced herein, other foam materials may be substituted for EVA, and the embodiments described herein should not be considered to be limited to only EVA foam. Various foam components, e.g., a shell or housing and a seal, can be directly joined to each other, either permanently or removably, or joined to each other via a joining component, such as a rigid frame, as described herein. In some embodiments, one or more of the foam components can be at least partially covered with a textile covering, such as an elastic fabric layer.

The EVA foam and/or elastic fabric can advantageously provide masks having improved aesthetics, comfort, and/or performance compared to masks made of conventional materials. The thermoformed EVA foam and/or fabric can allow the mask to look more at home and less medical, sterile, or intimidating in the bedroom environment in which it is used. The thermoformed EVA foam and/or fabric can provide a softer, warmer, and/or more comfortable mask for the user. In some cases, silicone masks are irritating, prone to sticking to the user's skin, and/or sweat inducing. In some cases, silicone masks cause chaffing and/or pressure spots/sores on the user's skin. In some embodiments, the thermoformed EVA foam and/or fabric masks of the present disclosure are non-sticking, non-irritating, and/or non-sweat inducing. The EVA foam can advantageously provide a light weight construction and reduce the overall weight of the mask system. The reduced weight advantageously reduces the forces, e.g., tensile force, required to seal the mask to the patient and therefore reduces tension in the headgear straps, which can increase patient comfort, provide for improved freedom of movement, and/or reduce pressure points. In some cases, material costs of the EVA foam are relatively low, which can help reduce the manufacturing costs for the mask system. In some embodiment, masks according to the present disclosure allow for the use of open/shut tooling, which can allow for mass manufacturing and/or reduced manufacturing costs. In embodiments including a textile covering, the textile covering can provide an aesthetic appearance and/or comfort for the user. For example, foam (with or without a textile cover) can be warmer to touch than the silicone seals of conventional masks. The textile covering can advantageously hide or lessen the appearance of bumps and/or marks created in the EVA foam during vacuum forming. The textile covering can provide improved wear resistance for the EVA foam.

FIG. 1 illustrates an example embodiment of a mask 100 including a shell 110 and a seal or cushion 120. In the illustrated embodiment, the shell 110 is made of or includes polycarbonate. The shell 110 can be made of or include any other suitable, conventional, relatively rigid material. The seal 120 is made of thermoformed EVA foam. The seal 120 can be coupled to the shell 110 via any appropriate binding method. Seals 120 made of thermoformed EVA foam can be made to correspond to and be used with various shells 110, including pre-existing shells 110 currently available. In some embodiments, a mask according to the present disclosure includes a shell made of a thermoformed EVA foam and a seal or cushion made of silicone or any other suitable, conventional material.

Figure 7:
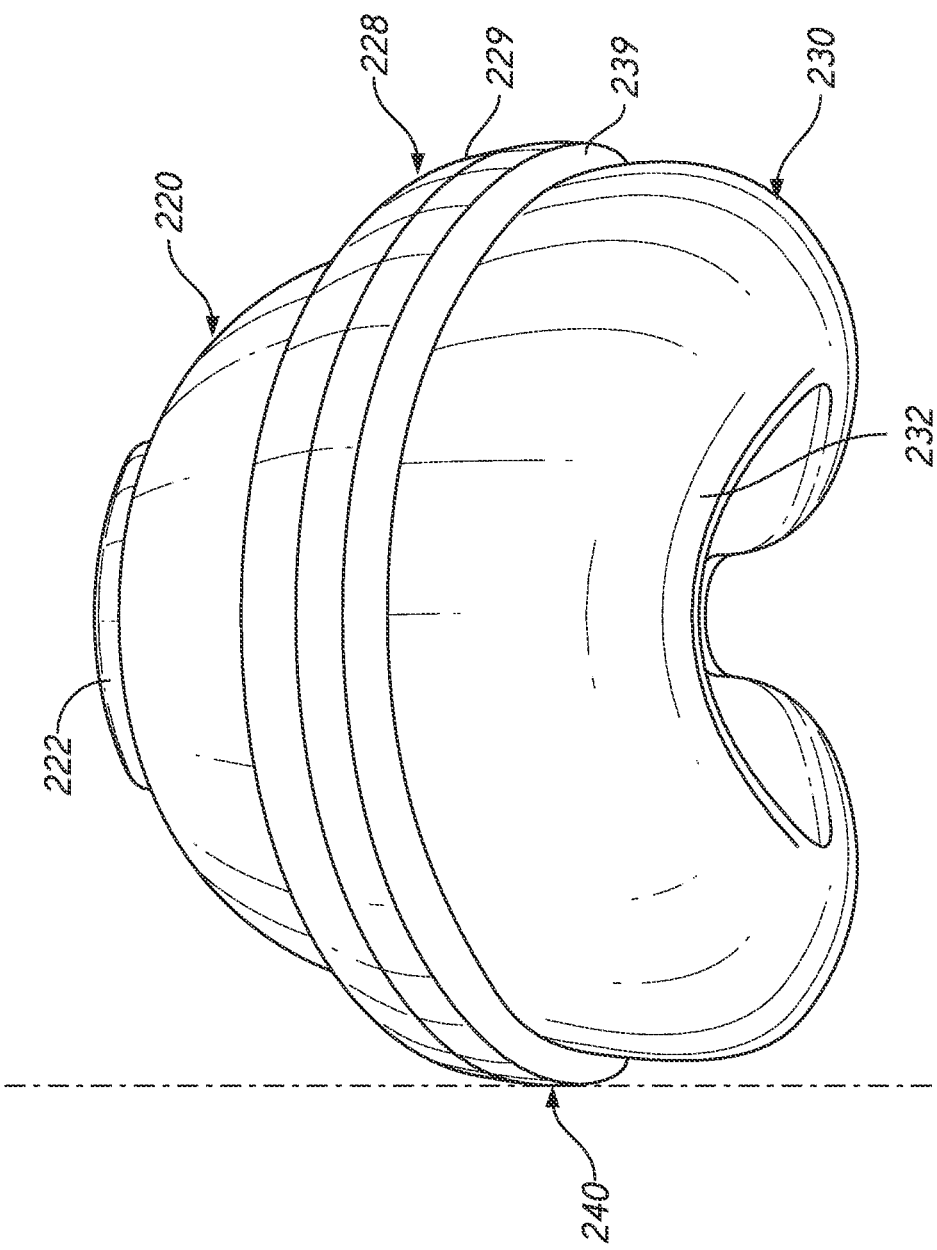
FIG. 7 illustrates a bottom view of the mask of FIG. 4.
Figure 8B:
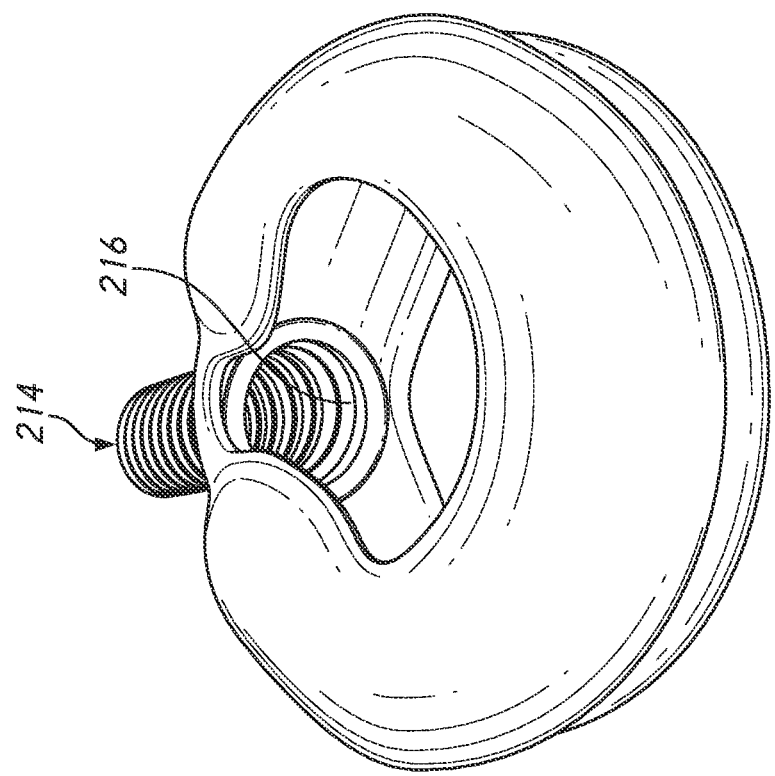
FIG. 8B illustrates a bottom rear perspective view of the mask and air conduit of FIG. 4.
Figure 8A:
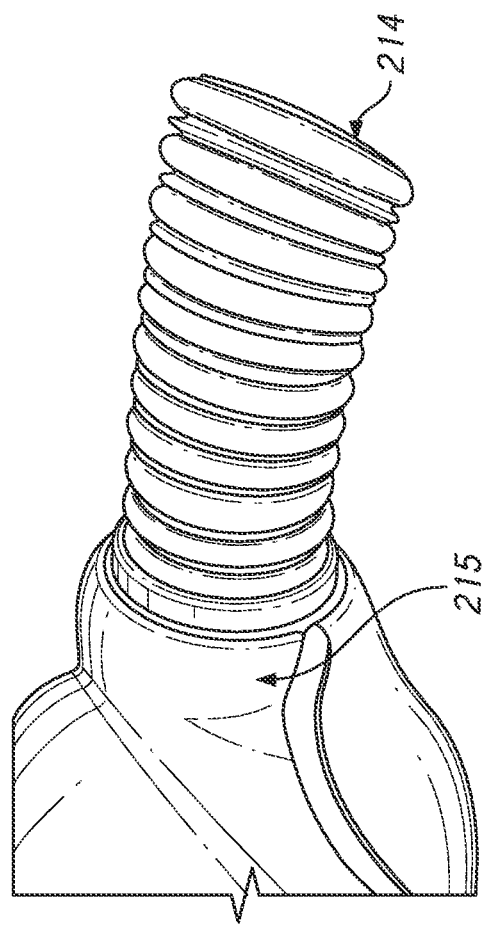
FIG. 8A illustrates a close-up view of a junction between the mask and air conduit of FIG. 4.
Figure 10:
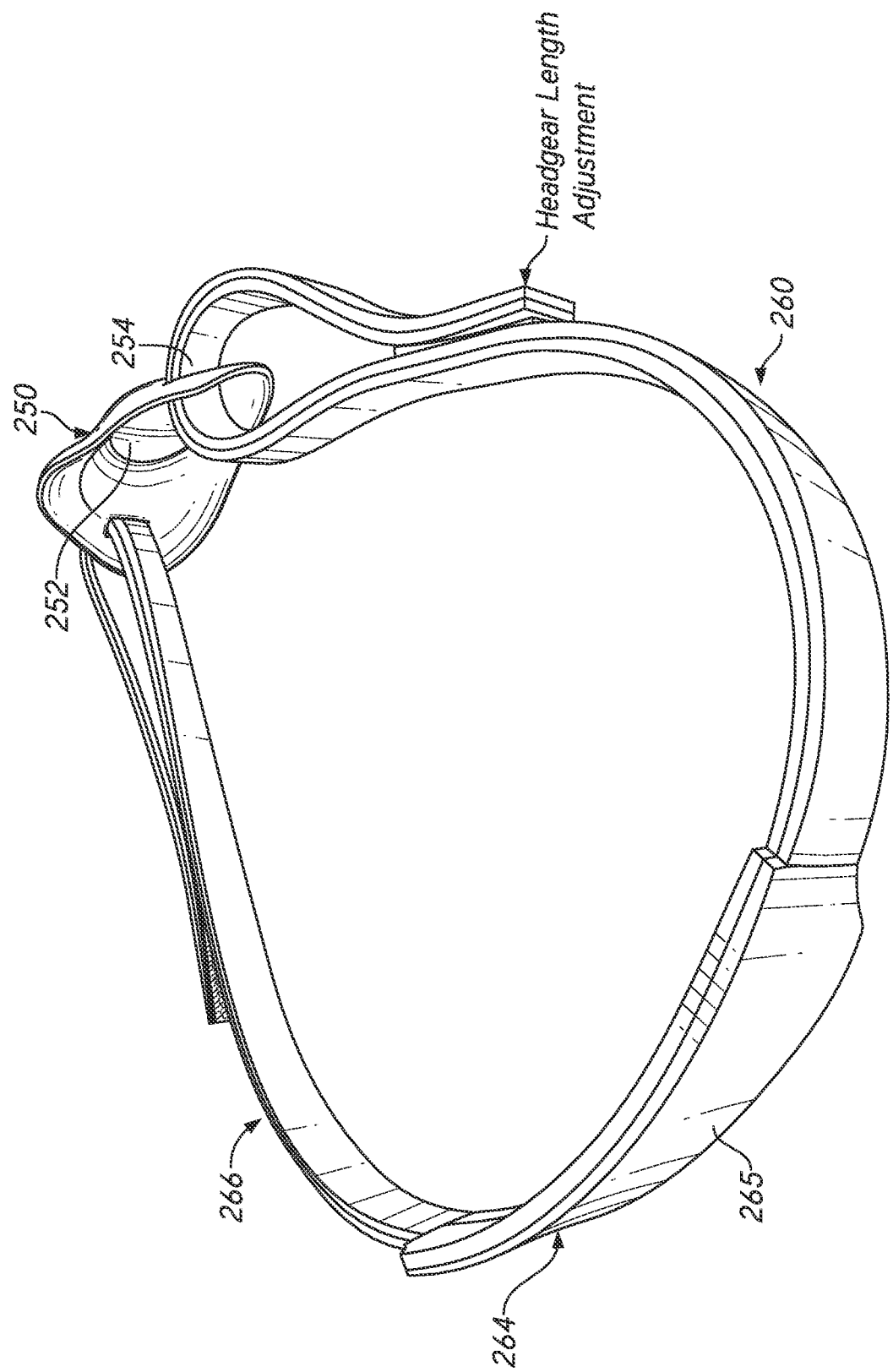
FIG. 10 illustrates a rear perspective view of a frame and headgear of the mask assembly of FIG. 2.
Figure 11:
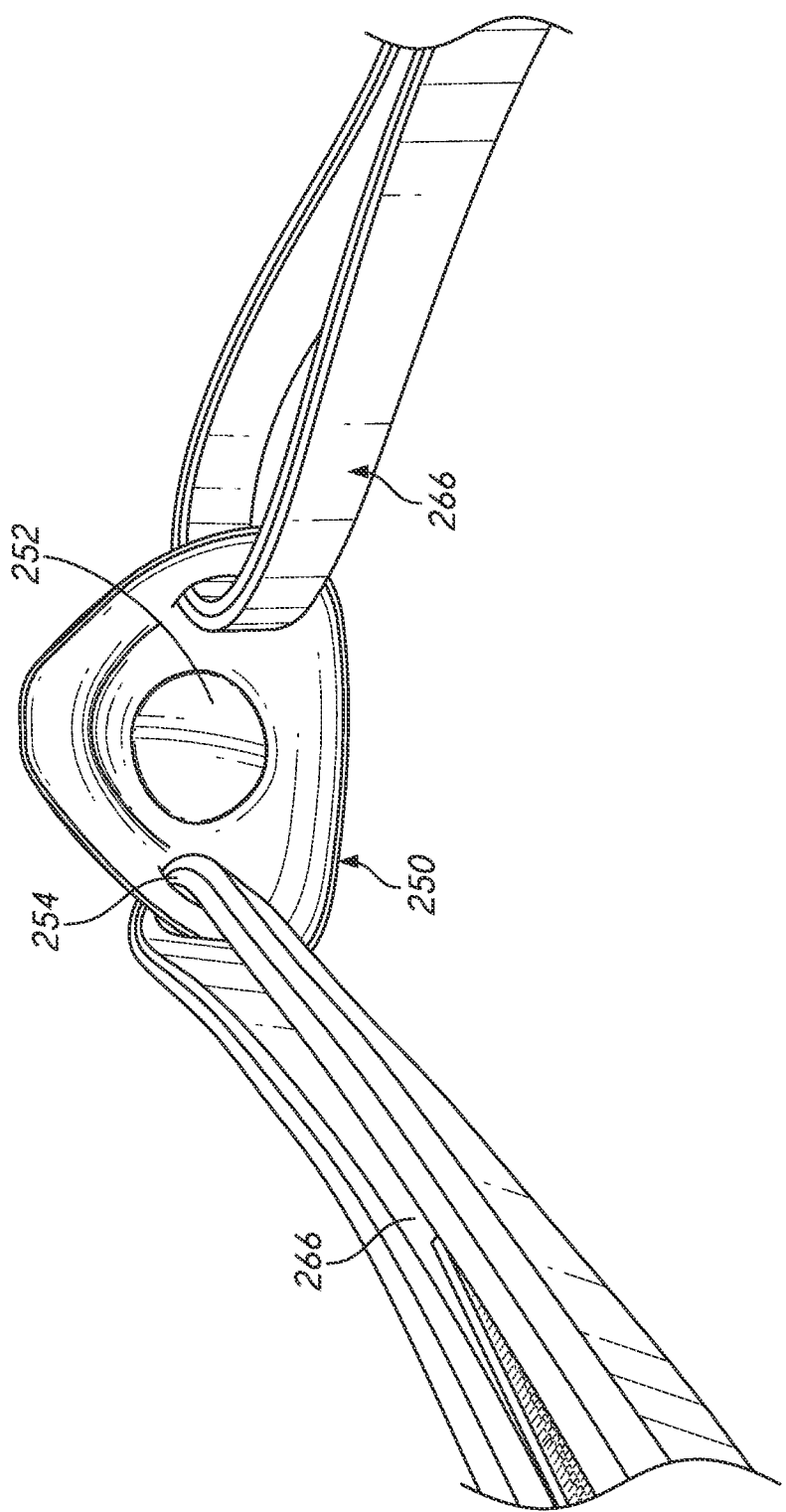
FIG. 11 illustrates a rear view of the frame and a portion of the headgear of FIG. 10.
Figure 12:
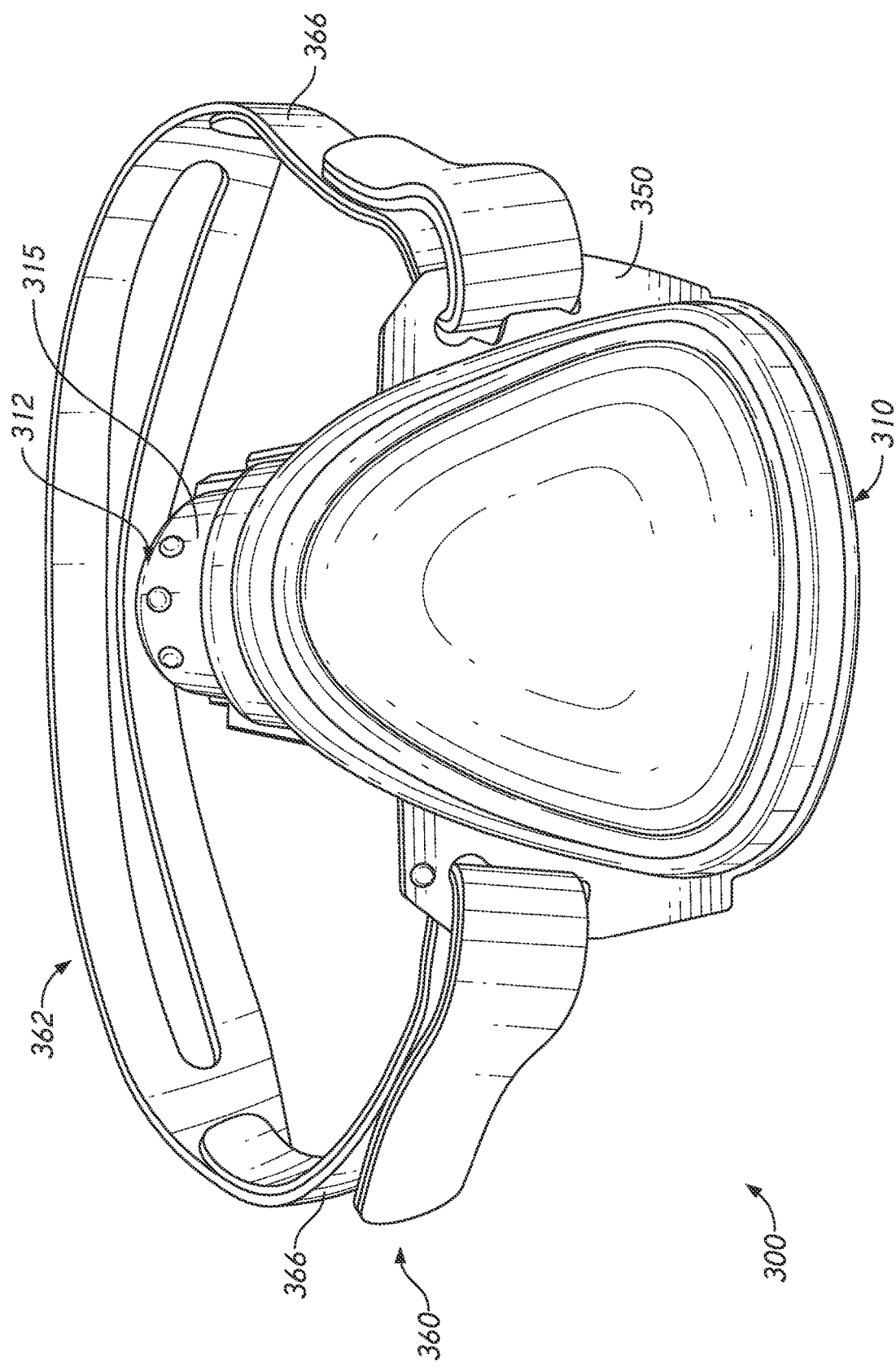
FIG. 12 illustrates a front view of an example embodiment of a mask assembly including thermoformed EVA components.
Figure 13:
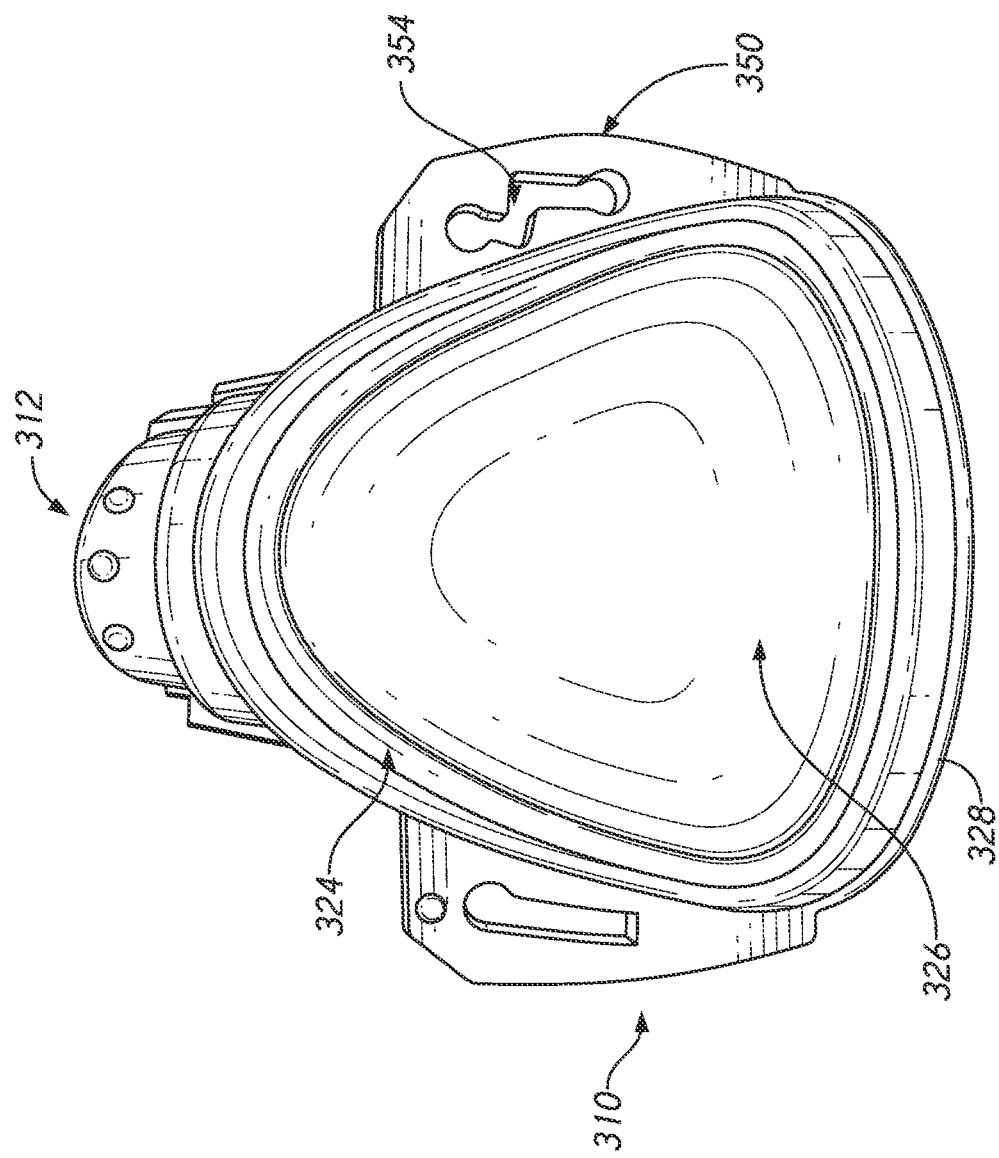
FIG. 13 illustrates a front view of a mask of the mask assembly of FIG. 12.

FIGS. 2-11 illustrate an example embodiment of a mask system 200 including a mask 210 having a shell or housing 220 and a seal 230. In the illustrated embodiment, both the shell 220 and seal 230 are made of thermoformed EVA foam. In some embodiments, the shell 220 and seal 230 are made of EVA foam having different densities. In some embodiments, the shell 220 and seal 230 are formed separately, e.g., via vacuum thermoforming as described herein, and then joined together at a seam or joint 240 to form a breathing chamber. A breathing chamber according to the present disclosure can be an enclosed space that surrounds at least one entrance to a user's airways (i.e., the user's nose and/or mouth) and through which a supply of pressurized gases can be delivered to the user's airways. As shown, the seam 240 extends around a patient-proximal edge of the shell 220 (i.e., the edge of the shell that is proximal to the patient, in use) and a patient-distal edge of the seal 230 (i.e., the edge of the shell that is distal from the patient, in use). In some embodiments, for example as shown in FIG. 7, the seam 240 protrudes or extends from an outer surface or side wall of the seal 230 and shell 220 and is the widest part of the mask 210. As shown, the proximal edge of the shell 220 can include a lip or flange 229 and the distal edge of the seal 230 can include a lip or flange 239, and the seam 240 can be formed by or between the lips 229, 239. The lips 229, 239 can provide an increased surface area for the seam 240 to provide a stronger joint. As shown in FIG. 7, when the mask 210 is viewed from the bottom, the seam 240 is proximal facing concave. The seam 240 can have a contour that corresponds to the shape of the seal 230. The shell 220 and seal 230, e.g., the lips 229, 230, can be joined together via any suitable means, for example, gluing, sewing, or welding. In the illustrated embodiment, the shell 220 and seal 230 are permanently joined.

Figure 61:
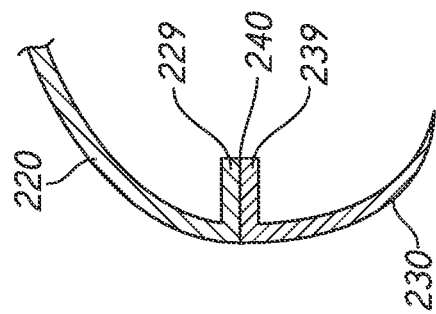
FIGS. 59-64 illustrate various configurations for a seam or joint between a shell and seal of the mask of the mask assembly of FIG. 48.
Figure 60:
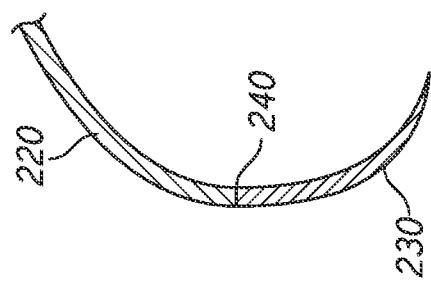
Figure 59:
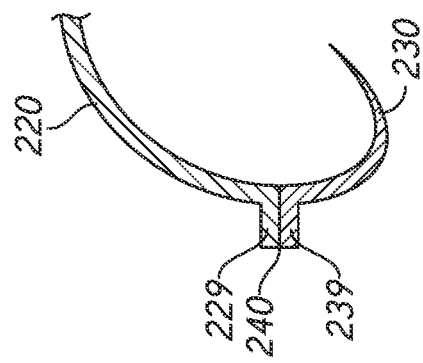

FIGS. 59-64 schematically illustrate various configurations for the seam or joint 240. FIG. 59 shows the arrangement of FIGS. 2-11, in which the seam 240 is formed between the lip 229 of the shell 220 and the lip 239 of the seal 230 and protrudes outwardly from or relative to an outer surface of the mask 210. FIG. 60 shows a variation in which the patient-proximal edge of the shell 220 abuts the patient-distal edge of the seal 230 to form the joint 240. The edges can be joined together via any suitable means, for example, adhesive(s), sewing, or welding. The inner and outer surfaces of the joint 240 are flush with the inner and outer surfaces, respectively, of the shell 220 and seal 230. FIG. 61 shows an embodiment in which the shell 220 includes a lip 229 and the seal 230 includes a lip 239, similar to the embodiment of FIG. 59. However, in the embodiment of FIG. 61, the lips 229, 239 and seam 240 protrude inwardly from or relative to an inner surface of the mask 210. The inwardly protruding seam 240 provides a flush joint on the outer surface of the mask.

Figure 64:
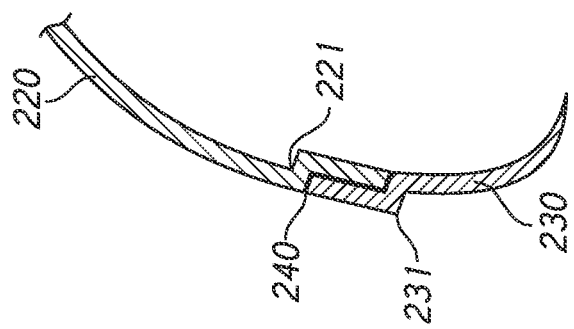
Figure 63:
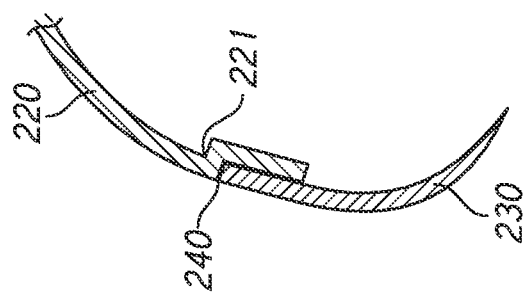
Figure 62:
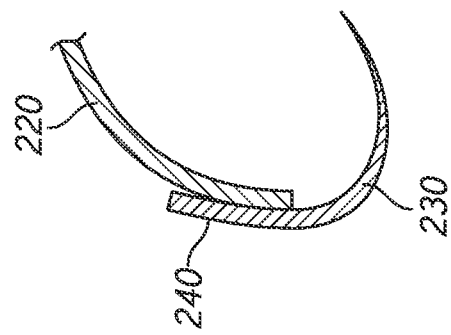

The seam 240 can be formed by a portion of the seal 230 adjacent the patient-distal edge of the seal 230 overlapping a portion of the shell 220 adjacent the patient-proximal edge of the shell 220, as shown in FIG. 62. Alternatively, a portion of the shell 220 adjacent the patient-proximal edge of the shell 220 can overlap a portion of the seal 230 adjacent the patient-distal edge of the seal 230. The seam 240 can be held together and/or reinforced via, for example, gluing, sewing, or welding. In some embodiments, for example as shown in FIG. 63, the shell 220 can have an inward step 221 proximate the patient-proximal edge of the shell 220 such that a portion of the shell 220 proximate the patient-proximal edge of the shell 220 is inwardly offset from a remainder of the shell 220 as shown. A portion of the seal 230 adjacent the patient-distal edge of the seal 230 overlaps the inwardly offset portion of the shell 220, and the patient-distal edge of the seal 230 can abut the step 221. The step 221 can help align the seal 230 with the shell 220. Such a configuration can allow the outer surfaces of the shell 220 and seal 230 to be flush or substantially flush with each other. Alternatively, the seal 230 can have an inward step and a portion of the shell 220 can overlap the inwardly offset portion of the seal 230. In some embodiments, the shell 220 includes an inward step 221 forming an inwardly offset portion and the seal 230 includes an outward step 231 forming an outwardly offset portion, as shown in FIG. 64. The outwardly offset portion of the seal 230 overlaps the inwardly offset portion of the shell 220. The patient-distal edge of the seal 230 can abut the step 221 of the shell 220 and/or the patient-proximal edge of the shell 220 can abut the step 231 of the seal 230. The steps 221, 231 can help align the seal 230 and shell 220 for connection and/or can help reinforce the joint 240.

Figure 65:
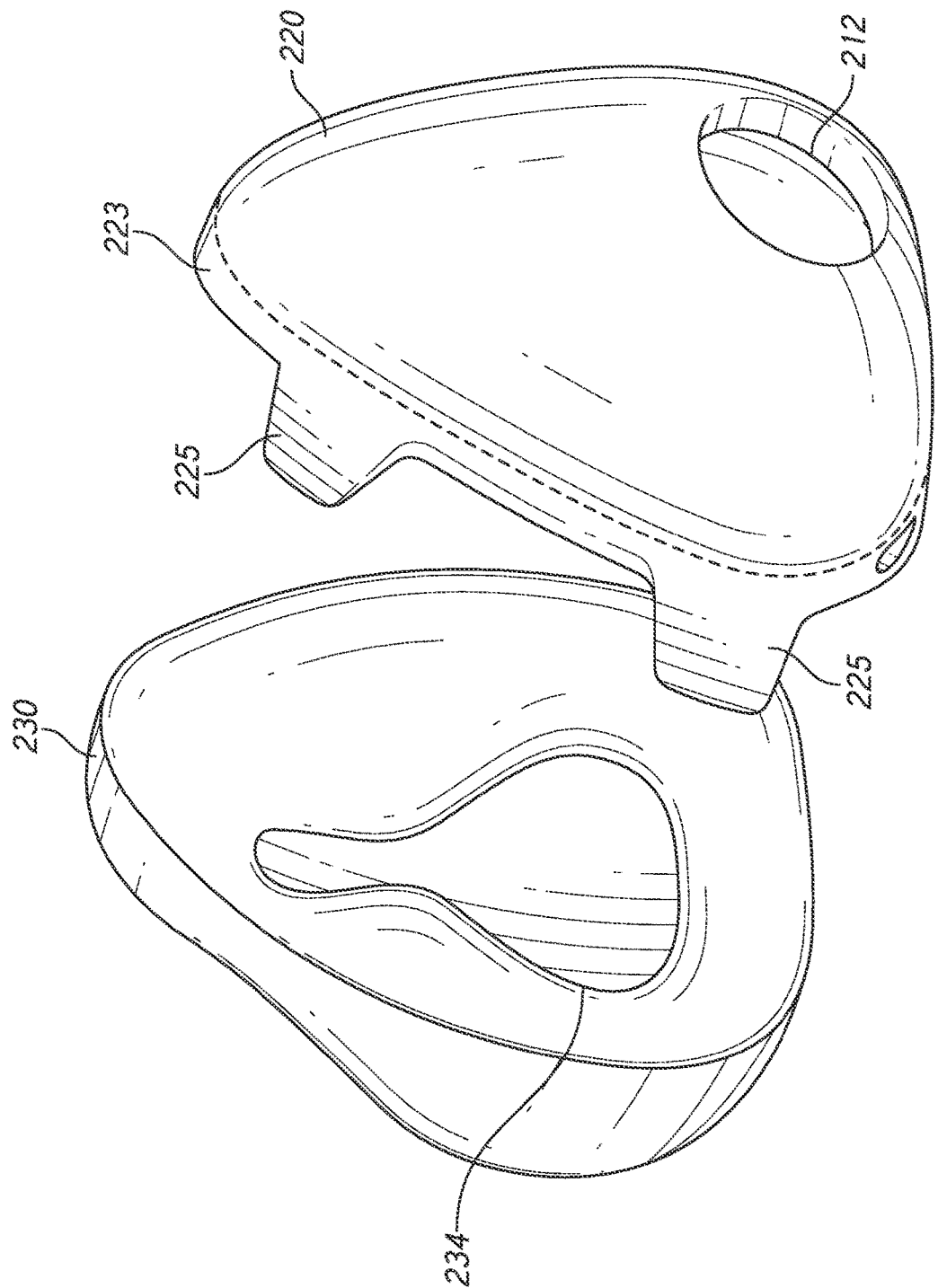
FIG. 65 illustrates an example embodiment of a seam or joint between a shell and seal of a mask.
Figure 68:
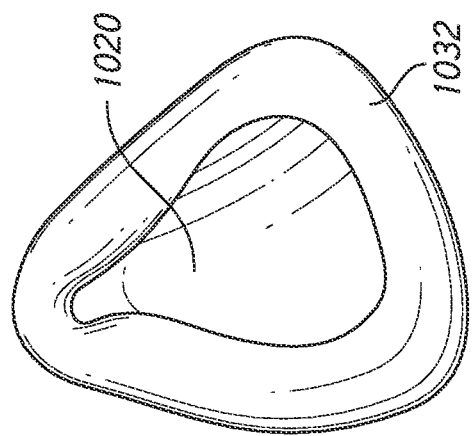
FIG. 68 illustrates a rear view of the cushion module of FIG. 66.

In some embodiments, the seam 240 can be formed by an overlapping region including protruding tabs, for example as shown in FIG. 65. As shown, the shell 220 includes an overlap region 223 adjacent the patient-proximal edge or perimeter of the shell 220. When the shell 220 and seal 230 are coupled, the overlap region 223 overlaps with an internal or external surface of a portion of the seal 230 adjacent the patient-distal edge of the seal 230, for example, as shown in or similar to the embodiment of FIG. 62. The overlap region 223 can be permanently joined to the seal 230 via, for example, sewing, adhesive(s), welding, and/or any other suitable means. In the illustrated embodiment, the inlet aperture 212 is formed in a front or patient-distal portion of the shell 220. Alternatively, the inlet aperture 212 can be formed in or at a top of the mask, similar to the embodiment of, for example, FIGS. 2-11.

The overlap region 223 includes one or more protruding tabs 225. The tabs 225 have an increased depth in a patient proximal-distal direction and/or form areas in which a greater surface area of the overlap region 223 overlaps with the seal 230 compared to a remainder of the overlap region 223. In the illustrated embodiment, the overlap region 223 includes two tabs 225, e.g., an upper tab 225 and a lower tab 225, on each lateral side of the shell 220. The tabs 225 can provide increased support and/or rigidity to selected regions of the seal 230. The tabs 225 can provide locations for connection of headgear straps to the mask. For example, in some embodiments, the overlap region 223 overlaps the external surface of the seal 230, and headgear components are attached to the tabs 225. The tabs 225 may or may not be fixed to or relative to the external surface of the seal 230. The overlap region 223 can include four tabs 225 as shown, e.g., upper and lower tabs 225 on each lateral side of the shell 220, to provide connection points for upper and lower straps of a four point headgear.

In some embodiments, the shell 220 includes a front or patient-distal wall 226 and a seal portion 228. In the embodiment illustrated in FIGS. 2-11, the front wall 226 of the shell 220 is convex distally. In some embodiments, a ledge 224, e.g., a flat ledge, extends around a base or proximal end of the front wall 226. In other words, the ledge 224 can form a transition between, or delimit the functionality and geometry of, the front wall 226 and seal portion 228 of the shell 220.

Figure 5:
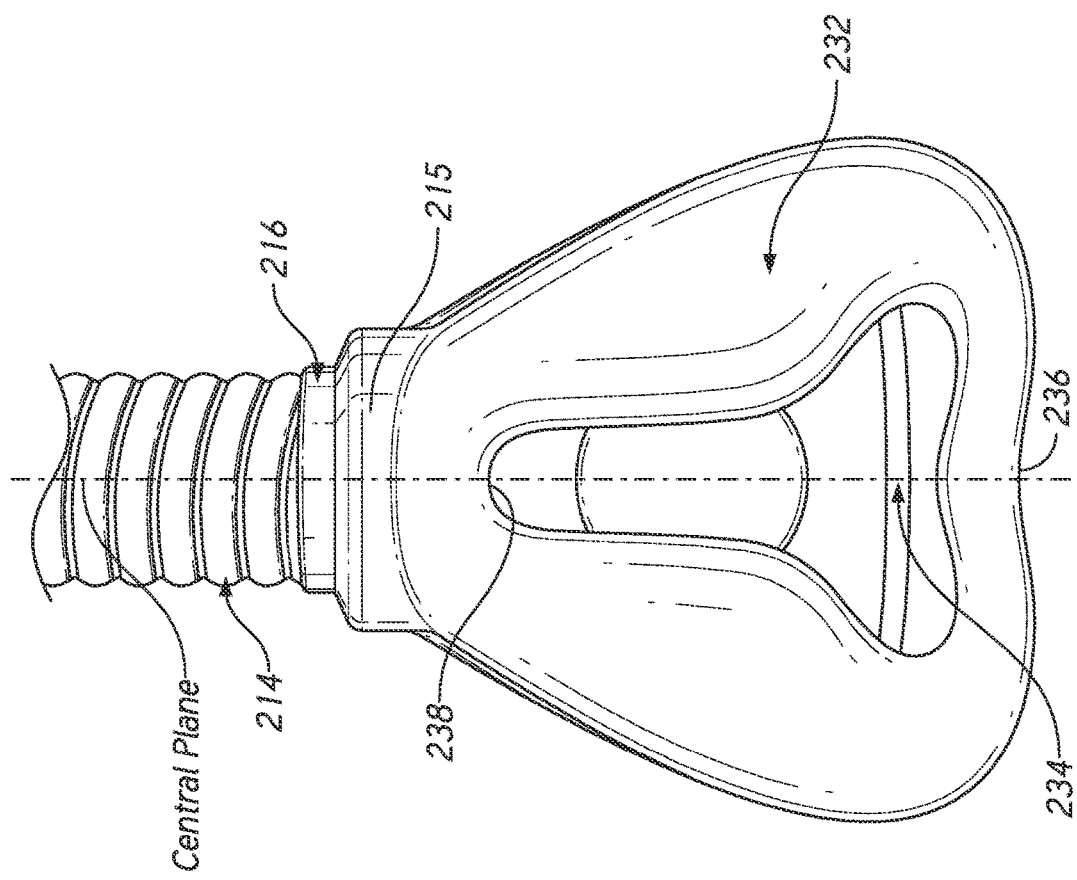
FIG. 5 illustrates a rear view of the mask and air conduit of FIG. 4.
Figure 6:
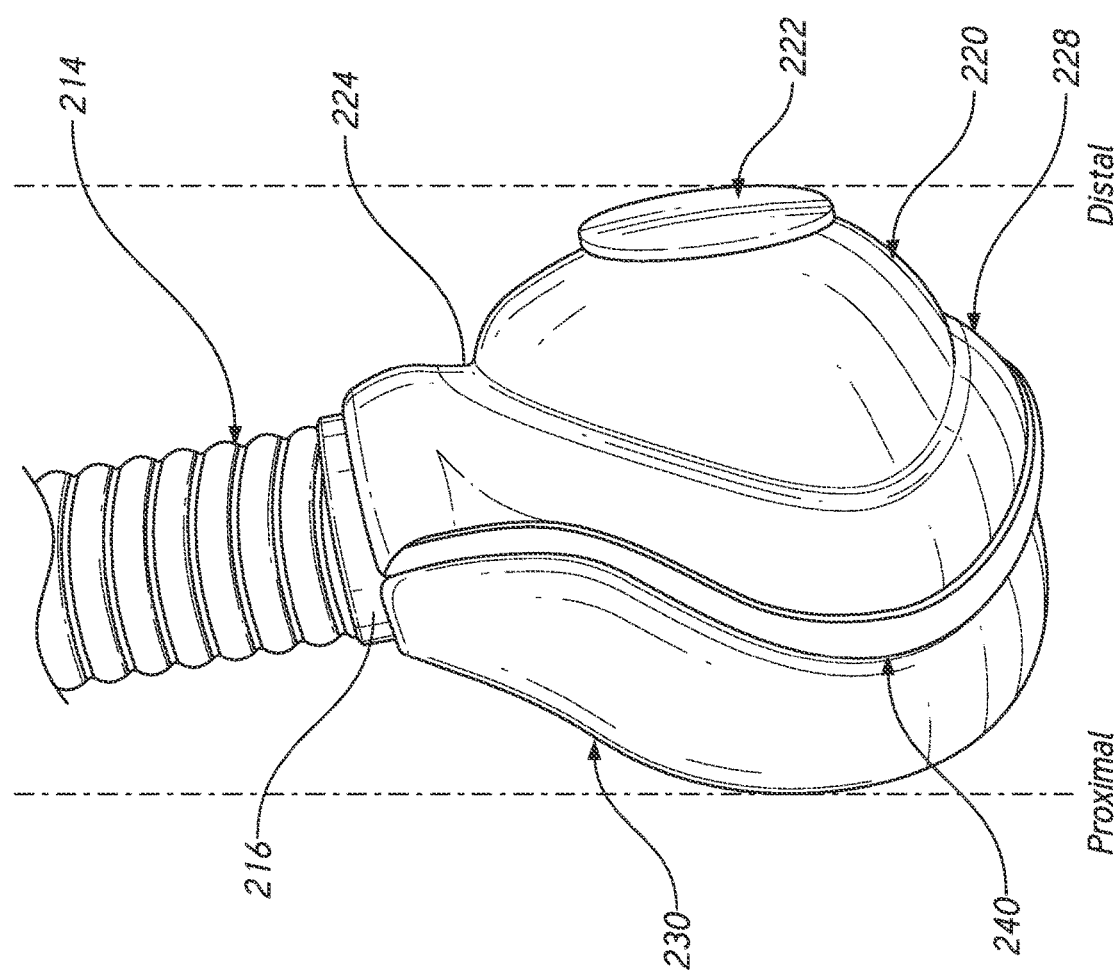
FIG. 6 illustrates a side view of the mask and air conduit of FIG. 4.

The seal 230 includes a rear or patient-proximal wall or surface 232. The rear surface 232 contacts and seals against the user's face in use. As shown in FIG. 7, when viewed from the bottom, the rear surface 232 can be proximal facing concave to correspond to the contours of the user's face. In the illustrated embodiment, the seal 230 also includes an aperture 234, e.g., a nasal aperture 234 that receives the user's nose in use. In some embodiments, the aperture 234 can receive the user's nose and mouth in use. In the illustrated embodiment, the seal 230 and aperture 234 are symmetrical about a central plane of the mask 210 as shown in FIG. 5. In some embodiments, a bottom surface or edge 236 of the seal 230 is concave downward as shown to correspond to the geometry of the user's upper lip. An apex 238 of the aperture 234 can receive and correspond to the bridge of the user's nose.

The mask 210 includes an inlet aperture 212 that receives a gas supply conduit 214 that delivers gases to the mask 210 in use. The inlet aperture 212 can be formed in or at a top end or surface of the mask 210. In the illustrated embodiment, the mask 210 includes a projection or extension 215 that includes the aperture 212. As shown, the projection 215 can be cylindrical or generally cylindrical. In some embodiments, the aperture 212 is formed or defined by both the shell 220 and seal 230. As shown, a front portion of the aperture 212 is formed or defined by the shell 220 and a back portion of the aperture 212 is formed or defined by the seal 230. In embodiments including a projection 215, a front portion of the projection 215 can be formed by or extend from the shell 220 and a back portion of the aperture 212 can be formed by or extend from the seal 230. In some embodiments, the seam 240 intersects the conduit 214 at or approximately at a midpoint of the aperture 212 and/or conduit 214. In other words, equal or approximately equal amounts of the aperture 212 can be formed by each of the shell 220 and seal 230 and a contact area between the shell 220 and conduit 214 is the same or about the same as a contact area between the seal 230 and conduit 214. In some embodiments, a conduit connector or conduit base 216 is coupled to the mask 210 within or proximate to the aperture 212, e.g., to an inner surface of the extension 215. In some embodiments, the conduit connector 216 is permanently coupled to the mask 210, e.g., to the extension 215. The conduit connector 216 can be a relatively rigid ring. The conduit connector 216 can be made of plastic. The conduit 214 can be coupled, either permanently or removably, to or integrally formed with the conduit connector 216. The conduit 214 can be permanently coupled to the conduit connector 216 and/or the mask 210, e.g., the extension 215, by any suitable means, e.g., with adhesive(s), by over-moulding, friction fit or welding. The conduit connector 216 can include internal retention features, and the conduit 214 can be coupled to the conduit connector 216 via the retention features. The conduit 214 can be coupled to the connector 216 via a snap-fit, a threaded connection (e.g., a helical bead of the conduit engages with a thread formed in the connector), a friction-fit, or other suitable mechanisms. In some embodiments, the conduit connector 216 includes two components configured to be coupled, permanently or detachably or removably, to each other. One of the components of the conduit connector 216 can be coupled to the mask 210, e.g., the extension 215, and the other can be coupled to the conduit 214.

In some embodiments, the mask system 200 includes headgear 260 for securing the mask system 200 to the user's face in use. The headgear 260 can operably couple to the mask 220 and the user's head and provide the force needed to obtain an adequate seal between the seal 230 and the user's face in use. In the illustrated embodiment, the headgear 260 includes a single strap 262. In some embodiments, the strap 262 includes a rear portion 264 and two side portions 266, with one of the side portion 266 extending from each end (e.g., lateral end) of the rear portion 264. The rear portion 264 rests along the back of the patient's head in use. The rear portion 264 can be inextensible or relatively inextensible. The side portions 266 can be extensible and/or elastic or somewhat elastic. The rear portion 264 can be made of foam, EVA foam. In some embodiments, the rear portion 264 includes a textile 265 covering at least partially surrounding the rear portion 264. In some embodiments, the side portions 266 are made of or include breathoprene. In the illustrated embodiment, the rear portion 264 is wider (e.g., in a vertical direction) than the side portions 266. Any suitable headgear can be used with the mask 210 and/or frame 250.

In some embodiments, the mask system 200 includes a yoke or frame 250. In the illustrated embodiment, the yoke 250 is made of thermoformed EVA foam and has a textile, e.g., elastic fabric, covering. The yoke 250 can receive or be coupled to the headgear 260. As shown, the yoke 250 includes an aperture 254 proximate each lateral end or side of the yoke 250. Each of the apertures 254 adjustably receives one end of the headgear strap 262 as shown. In the illustrated embodiment, to couple the headgear strap 262 to the frame 250, a free or distal end of the strap 262 is threaded through one of the apertures 254 from a rear, inner, or proximal side of the frame 250 to a front, outer, or distal side of the frame 250 and then looped back on itself so that the free or distal end or a portion of the strap 262 proximate the free or distal end can couple to a more central or proximal portion of the strap 262. The distal end or distal portion of the strap 262 can be releasably coupled or secured to the more proximal portion of the strap 262. For example, in some embodiments, the distal end or distal portion includes the hook or loop part of a hook and loop connector and the more proximal portion includes the other of the hook or loop parts of the hook and loop connector. The straps 262, e.g., the side portions 266, can be adjusted to adjust the size of the headgear 260 and/or the strap tension on the patient's face. The lightweight construction of the EVA foam components of the mask system 200 (e.g., the mask 210 and frame 250) can advantageously reduce or lower the tensile forces needed to seal the mask 210 to the patient's face in use, which can increase or improve patient comfort.

The frame 250 can be removably coupled to the mask 210, for example, the shell 220. A connector 222 can be coupled to an outer or distal side, e.g., to the front wall 226 of the shell 220, and a corresponding connector 252 can be coupled to an inner or proximal side of the yoke 250. In the illustrated embodiment, the connector 222 is coupled to a distal most point or area of the shell 220. The connectors 222, 252 can be light weight to help reduce the overall weight of the mask system 200. In some embodiments, the shell 220 connector 222 is the hook or loop part of a hook and loop connector, and the yoke 250 connector 252 is the other of the hook or loop parts of the hook and loop connector. Other connectors are also possible, for example, a snap fit button or clips. In some embodiments, a shape, e.g., a curvature, of the frame 250 corresponds to the shape, e.g., curvature of the front wall 226 of the shell 220.

FIGS. 12-17B illustrate an example embodiment of a mask system 300 including a mask 310 having a shell or housing 320 and a seal 330. The geometry of the mask 310 can be the same as or similar to the geometry of the mask 210 of FIGS. 2-11. In the illustrated embodiment, both the shell 320 and seal 330 are made of thermoformed EVA foam. In some embodiments, the shell 320 and seal 330 are made of EVA foam having different densities. In some embodiments, the shell 320 and seal 330 are formed separately, e.g., via vacuum thermoforming as described herein, and then joined together at a seam 340. As shown, the seam 340 extends around a proximal edge of the shell 320 and a distal edge of the seal 330. As shown, the patient-proximal edge of the shell 320 can include a lip or flange 329 extending radially outwardly from an outer surface of the shell 320 and the patient-distal edge of the seal 330 can include a lip or flange 339 extending radially outwardly from an outer surface of the seal 330, and the seam 340 can be formed by or between the lips 329, 339. The lips 329, 339 can provide an increased surface area for the seam 340 to provide a stronger joint. In some embodiments, the lips 329, 339 can be compressed or welded together to create a rigid or relatively more rigid component of the mask. The seam 340 can be configured similar to seam 240, for example, according to any of the embodiments shown in and described with respect to FIGS. 59-65.

In some embodiments, the shell 320 includes a front wall 326 and a seal portion 328. In the illustrated embodiment, the front wall 326 of the shell 320 is convex distally. In some embodiments, a ledge 324, e.g., a flat ledge, extends around a base or proximal end of the front wall 326. In other words, the ledge 324 can form a step transition between the front wall 326 and seal portion 328 of the shell 320.

Figure 14:
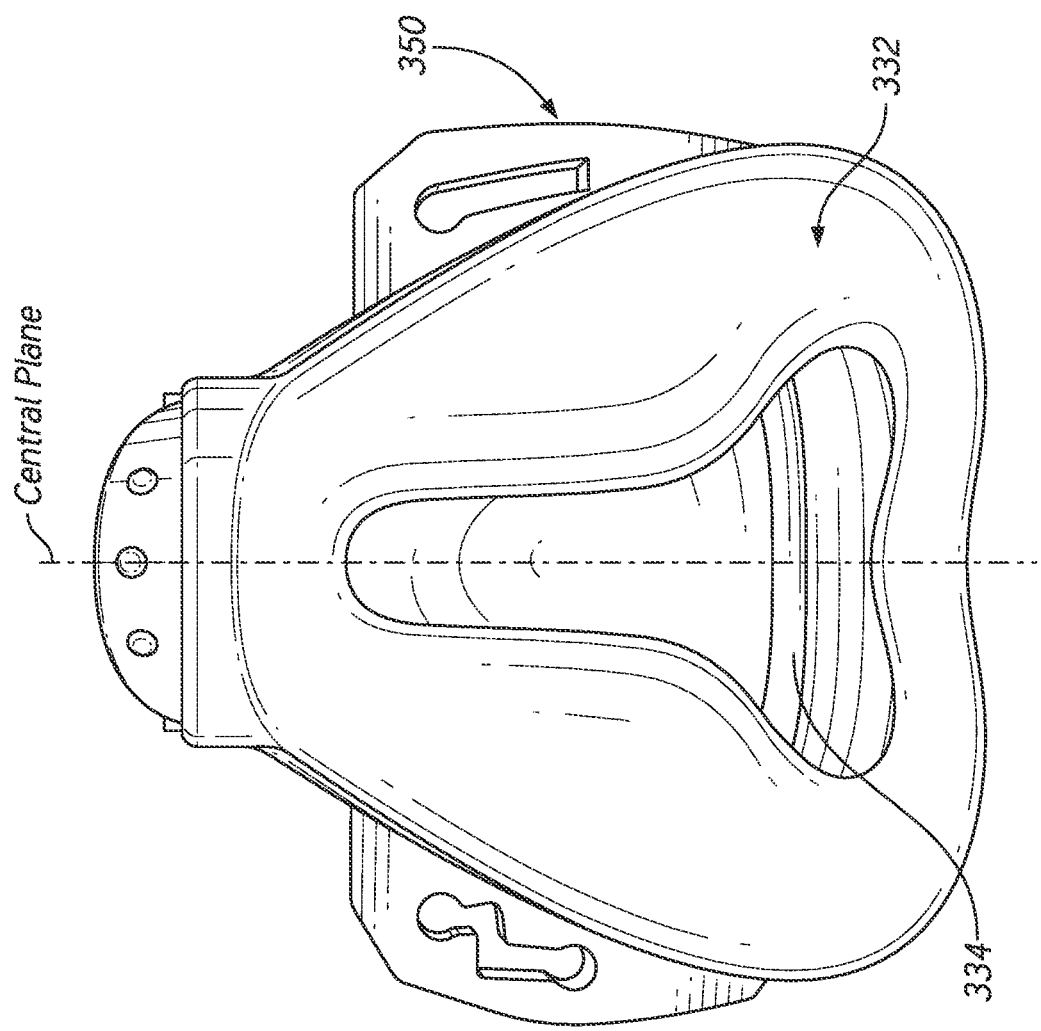
FIG. 14 illustrates a rear view of the mask of FIG. 13.
Figure 15:
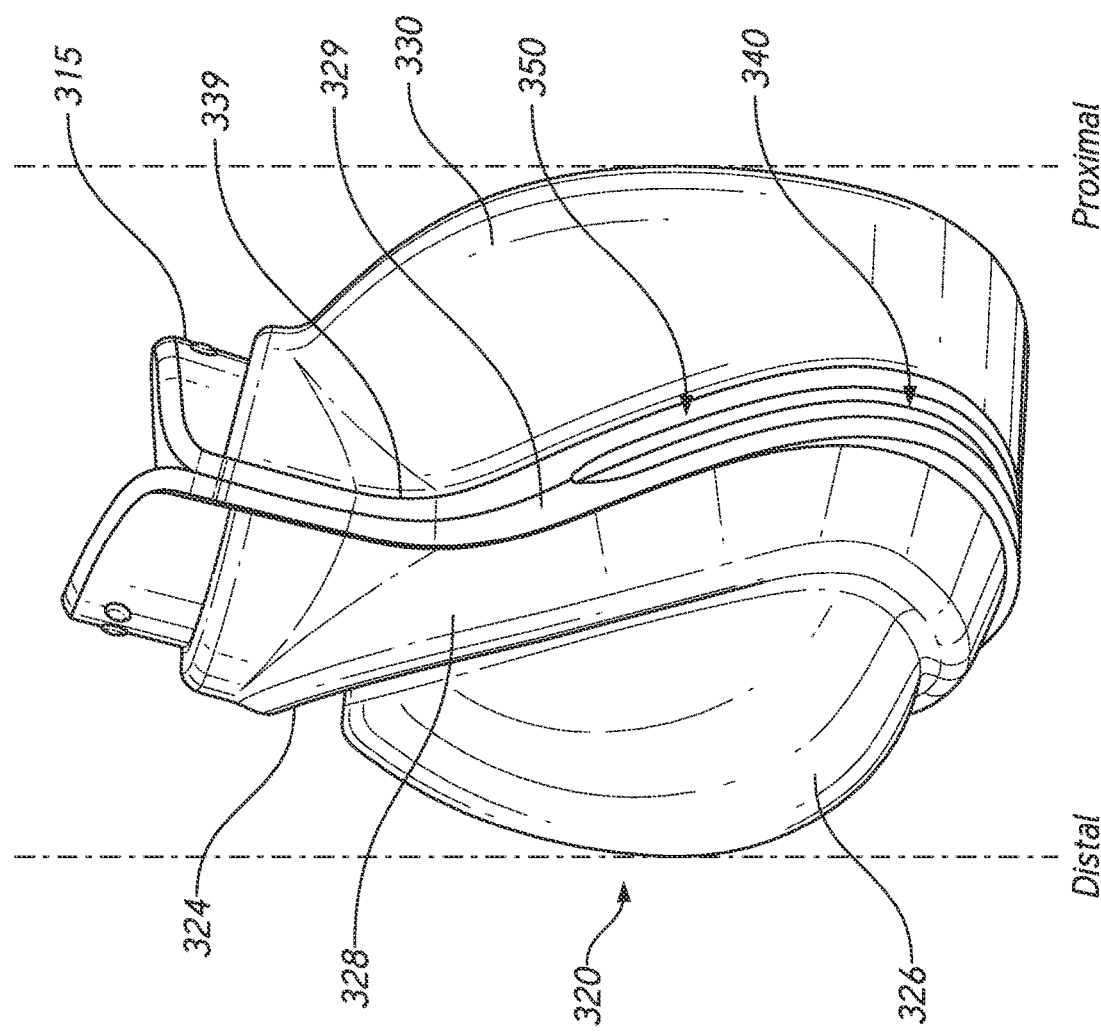
FIG. 15 illustrates a side view of the mask of FIG. 13.
Figure 16:
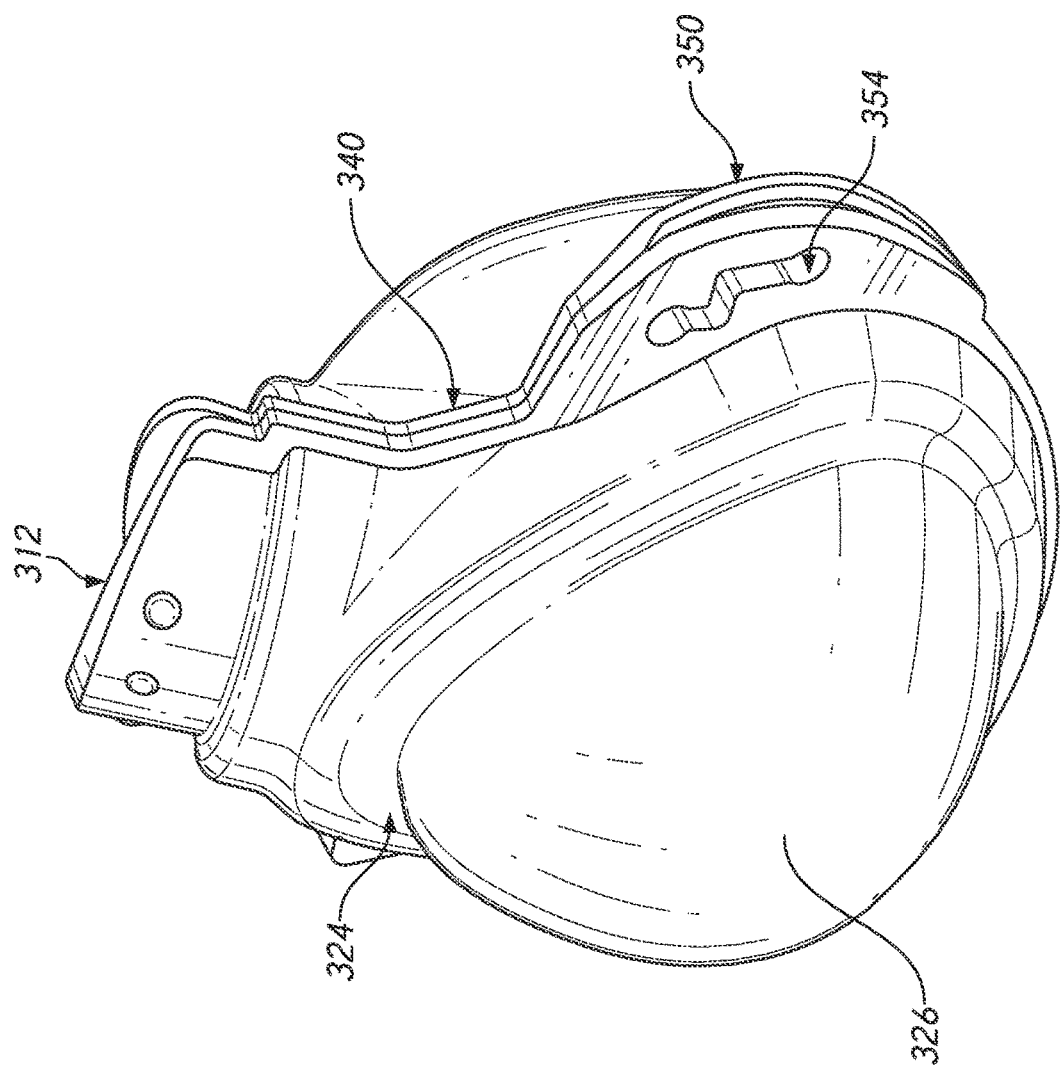
FIG. 16 illustrates a front side perspective view of the mask of FIG. 13.
Figure 17B:
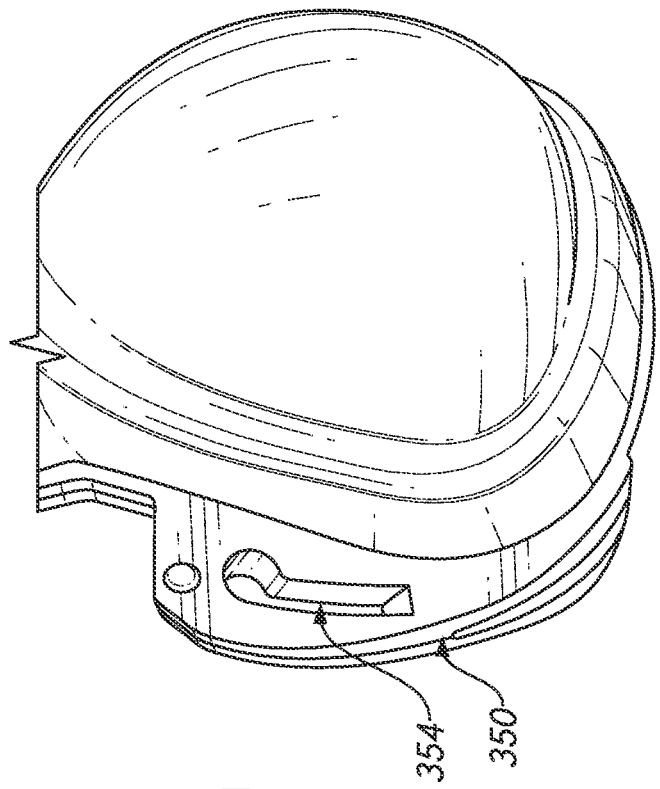
FIG. 17B illustrates a close up view of a headgear connector of the mask of FIG. 12.
Figure 17A:
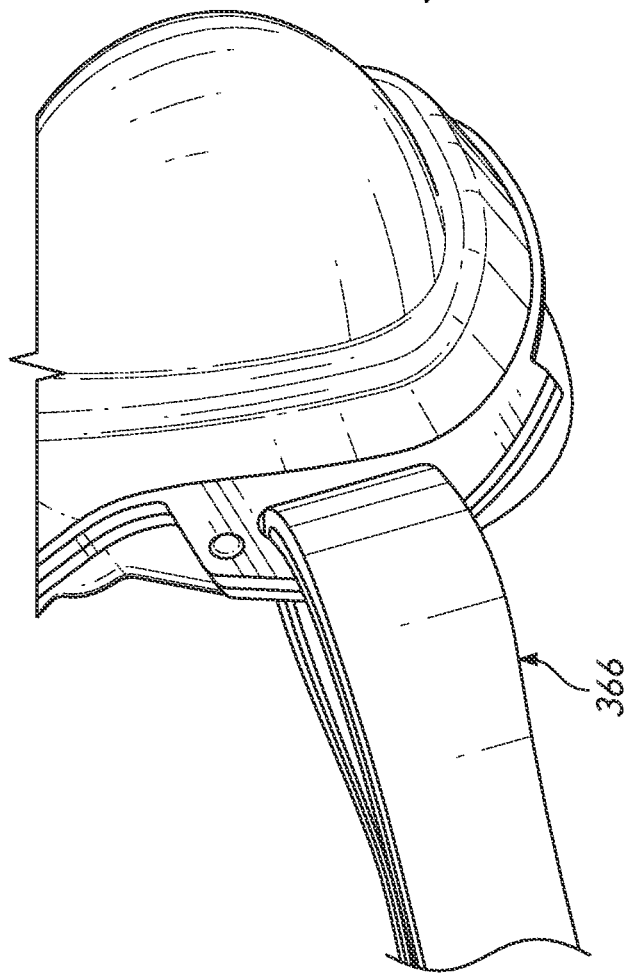
FIG. 17A illustrates a close up of a connection between the mask and headgear of the mask assembly of FIG. 12.
Figure 18C:
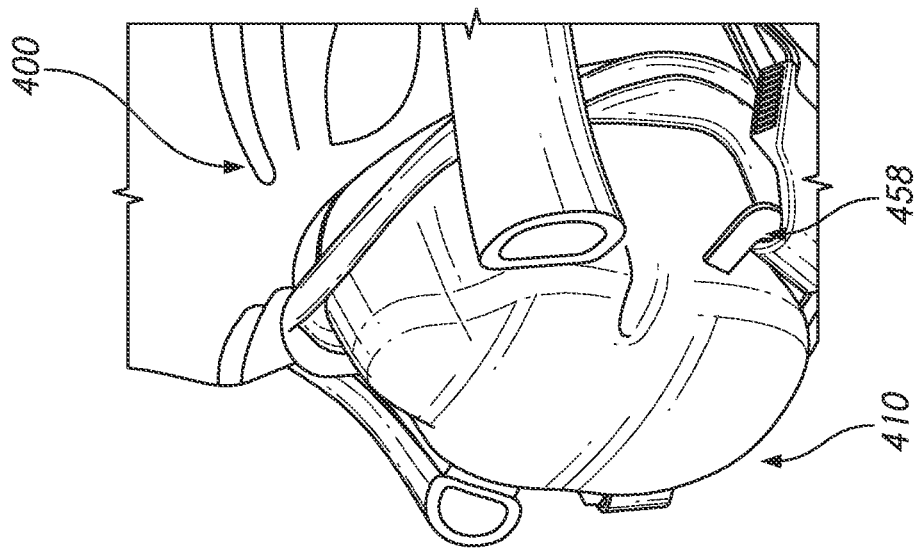
FIG. 18C illustrates a close up front perspective view of the mask assembly of FIG. 18A.
Figure 18B:
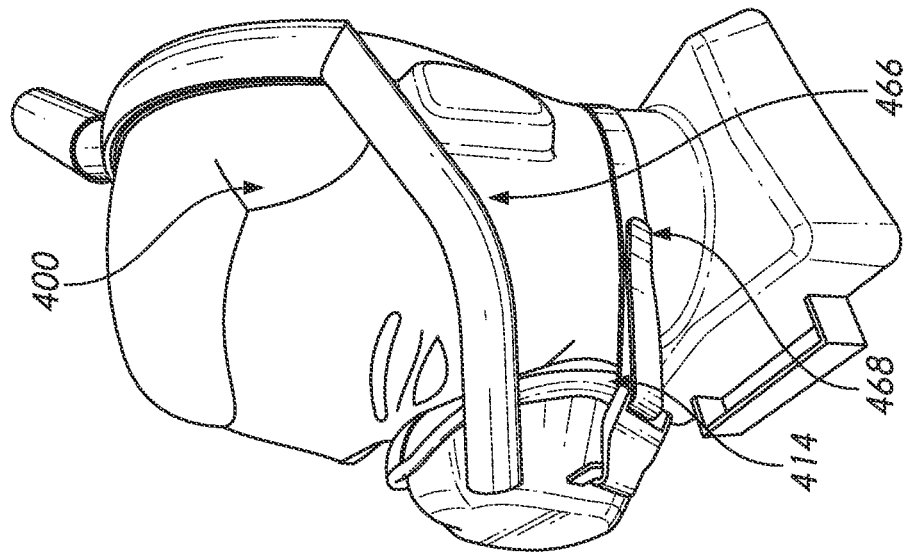
FIG. 18B illustrates a side perspective view of the mask assembly of FIG. 18A.
Figure 18A:
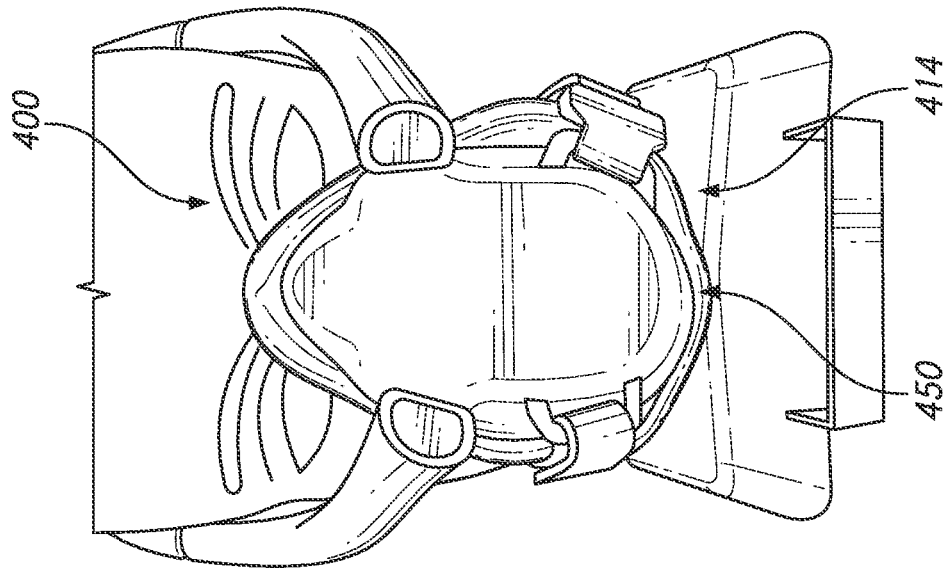
FIG. 18A illustrates a front view of an example embodiment of a mask assembly including thermoformed EVA components coupled to a user's face.
Figure 19:
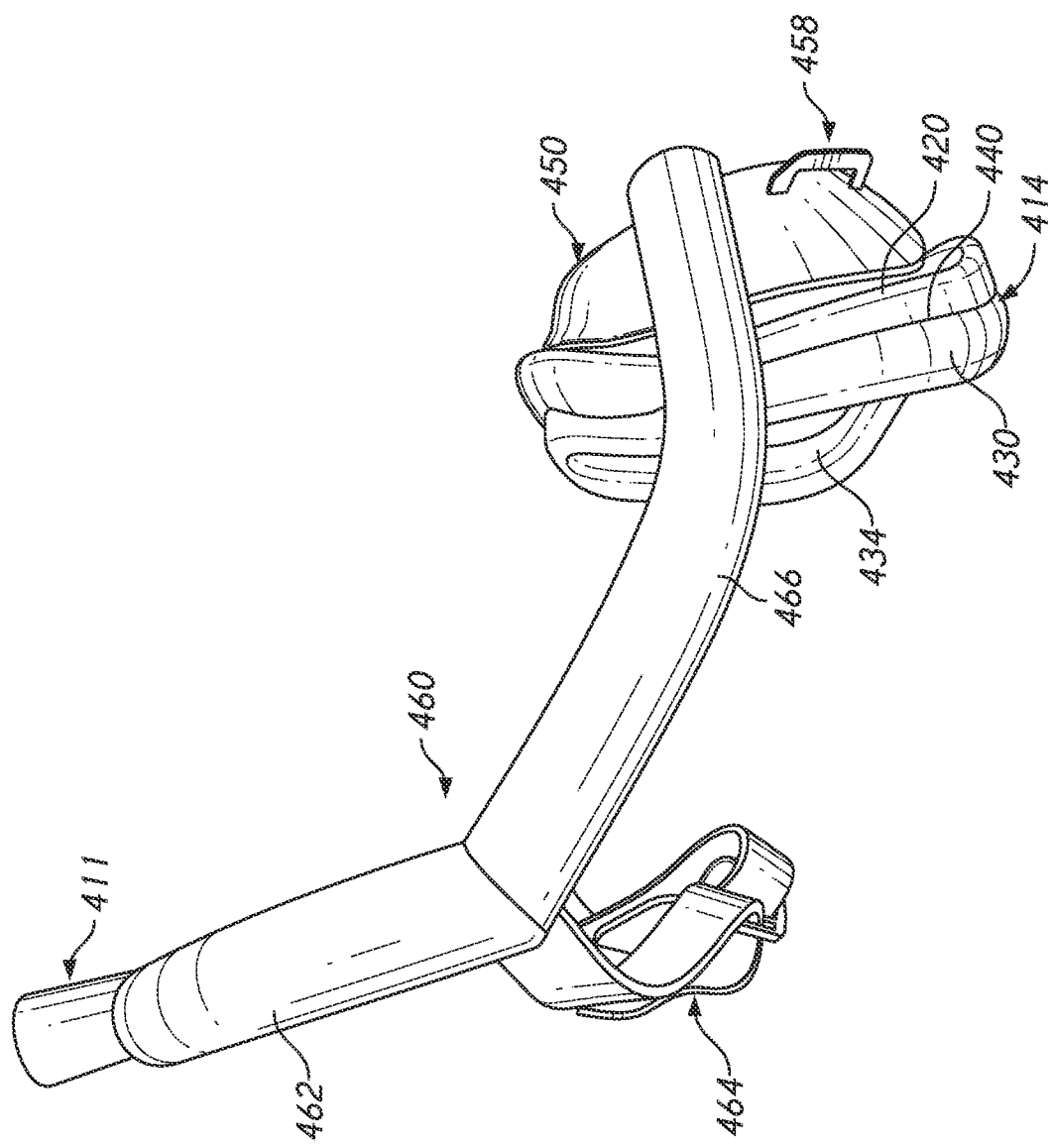
FIG. 19 illustrates a side view of the mask assembly of FIG. 18A.

The seal 330 includes a rear or proximal wall or surface 332. The rear surface 332 contacts and seals against the user's face in use. In the illustrated embodiment, the seal 330 also includes a nasal aperture 334 that receives the user's nose in use. In some embodiments, the seal 330 can include an aperture that receives the user's nose and mouth in use. In the illustrated embodiment, the seal 330 and aperture 334 are symmetrical about a central plane of the mask 310 as shown in FIG. 14.

The mask 310 includes an inlet aperture 312 that receives a gas supply conduit that delivers gases to the mask 310 in use. The inlet aperture 312 can be formed in or at a top end or surface of the mask 310. In the illustrated embodiment, the mask 310 includes a projection or extension 315 that includes the aperture 312. As shown, the projection 315 can be cylindrical or generally cylindrical. In some embodiments, the aperture 312 is formed or defined by both the shell 320 and seal 330. As shown, a front portion of the aperture 312 is formed or defined by the shell 320 and a back portion of the aperture 312 is formed or defined by the seal 330. In embodiments including a projection 315, a front portion of the projection 315 can be formed by or extend from the shell 320 and a back portion of the aperture 312 can be formed by or extend from the seal 330. In some embodiments, the seam 340 intersects the conduit at or approximately at a midpoint of the aperture 312 and/or conduit. In some embodiments, a conduit connector or conduit base is coupled to the mask 310 within or proximate to the aperture 312, e.g., to an inner surface of the extension 315. The conduit connector can be similar to and include some or all of the features described with respect to the conduit connector 216 of the embodiment of FIGS. 2-11. The conduit can be coupled to or integrally formed with the conduit connector 316. The conduit can be permanently coupled to the conduit connector 316 and/or the mask 310, e.g., the extension 315 by any suitable means, e.g., with adhesive(s).

In some embodiments, the mask system 300 includes headgear 360 for securing the mask system 300 to the user's face in use. The headgear 360 can operably couple to the mask 310 and the user's head and provide the force needed to obtain an adequate seal between the seal 330 and the user's face in use. Any suitable headgear can be used with the mask 310. In the illustrated embodiment, the headgear 360 includes a strap 362 having two side portions 366.

In the embodiment of FIGS. 12-17B, the mask 310 includes a headgear connector 350 extending from each lateral side of the mask 310. In some embodiments, the headgear connectors 350 are positioned at or approximately at a vertical midpoint of the mask 310 or of the rear surface 332 of the seal 330. The headgear connectors 350 can be made of thermoformed EVA foam. In the illustrated embodiment, the headgear connectors 350 extend from the seam 340. In some embodiments, the headgear connectors 350 can extend from one or both of the flanges 329, 339. The headgear connectors 350 can be coupled to or integrally formed with the flange 329 and/or flange 339. Each of the headgear connectors 350 includes an aperture 354 that removably and/or adjustably receives the side portions 366 of the headgear 360. The mask system 300 therefore does not require a separate component, such as a frame 250 as shown in the embodiment of FIGS. 2-11, to secure the headgear 360 to the mask 310 due to the integrated headgear connectors 350. This can allow the overall design of the mask 310 and/or mask system 300 to be simplified. For example, the mask system 300 need only include a mask 310 and a headgear 360. The simplified design can allow for easier assembly of the mask system 300 and/or a lighter weight construction. A mask system 300 including fewer components can reduce manufacturing costs. The light weight construction can advantageously allow for lower tensile forces to be required to achieve an adequate seal with the patient's face, which can increase or improve patient comfort.

Each of the apertures 354 adjustably receives one end of the headgear strap 362 as shown. In the illustrated embodiment, to couple the headgear strap 362 to the mask 310, a free or distal end of the strap 362, e.g., of the side portion 366, is threaded through one of the apertures 354 from a rear, inner, or proximal side of the headgear connector 350 to a front, outer, or distal side of the headgear connector 350 and then looped back on itself so that the free or distal end or a portion of the strap 362 proximate the free or distal end can couple to a more central or proximal portion of the strap 362. The free or distal end or distal portion of the strap 362 can be releasably coupled or secured to the more central or proximal portion of the strap 362. For example, in some embodiments, the distal end or distal portion includes the hook or loop part of a hook and loop connector and the more central or proximal portion includes the other of the hook or loop parts of the hook and loop connector. The strap 362, e.g., the side portions 366, can be adjusted, e.g., by adjusting the amount of overlap of the distal portion with the central or proximal portion, to adjust the size of the headgear 360 and/or the strap tension on the patient's face. The lightweight construction of the EVA foam components of the mask system 300 (e.g., the mask 310 and headgear connectors 350) can advantageously reduce or lower the tensile forces needed to seal the mask 310 to the patient's face in use, which can increase or improve patient comfort.

Figure 20:
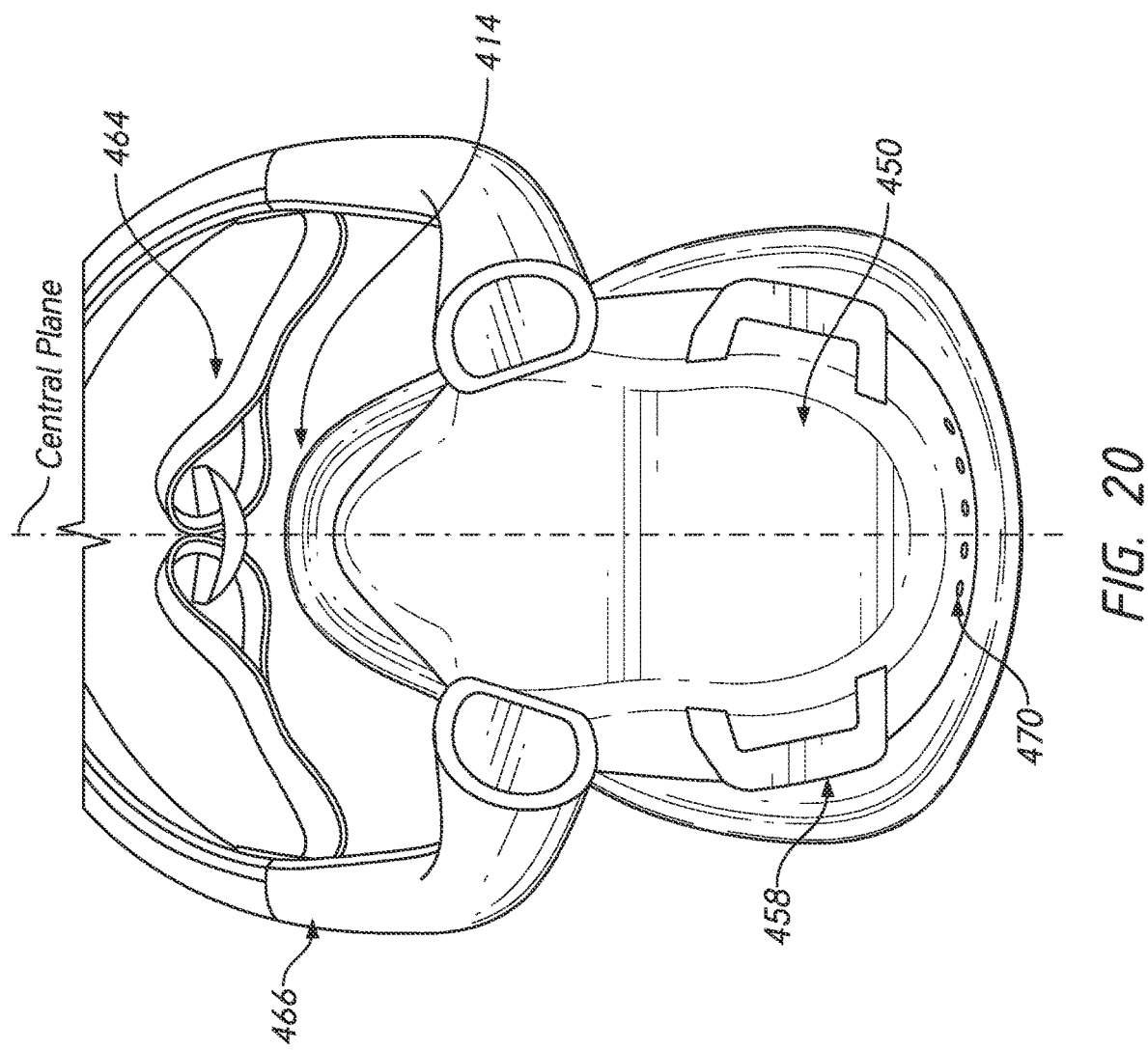
FIG. 20 illustrates a front view of the mask assembly of FIG. 18A.

FIGS. 18A-26B illustrate an example embodiment of a mask system 400 including a mask 410 having a shell or housing 420, a seal 430, and a frame 450. In the illustrated embodiment, the mask 410 is symmetrical about a central plane of the mask 410 as shown in FIG. 20. In the illustrated embodiment, both the shell 420 and seal 430 are made of thermoformed EVA foam. In some embodiments, the shell 420 and seal 430 are made of EVA foam having different densities. The shell 420 and seal 430 can be soft or relatively soft and/or flexible. The flexibility of the shell 420 and/or seal 430 can advantageously allow the mask 410 to adapt or conform to the user's face to form an adequate seal. In some embodiments, the shell 420 and seal 430 are formed separately, e.g., via vacuum thermoforming as described herein, and then joined together at a seam 440. The seam 440 can be similar to the seam or joint 240 of the embodiment of FIG. 60. The shell 420 and seal 430 together form a cushion module 414.

The frame 450 is coupled to the cushion module 414. In the illustrated embodiment, the frame 450 is coupled to the shell 420 portion of the cushion module 414. The frame 450 can be permanently coupled to the cushion module 414 with any suitable means, for example, using adhesive(s) or various connectors. In some embodiments, the frame 450 is rigid (or relatively rigid compared to the cushion module 414). The frame 450 can be made of a rigid EVA foam or another light-weight and relatively rigid material. The rigidity of the frame 450 advantageously provides support to couple, e.g., rigidly couple, various forms and/or components of headgear to the mask 410. Despite the rigidity provided by the frame 450, the EVA foam can still provide a relatively light weight construction and/or some flexibility for the frame 450. The light weight construction of the mask 410 due to the EVA foam construction of the cushion module 414 and/or frame 450 can advantageously reduce the tensile forces needed for headgear (for example, as described herein) to seal the cushion module 414 with the user's face, which can improve patient comfort. In the illustrated embodiment, the frame 450 includes a textile covering. The textile covering can be permanently connected, e.g., laminated, to the underlying foam. The textile covering can help improve the aesthetic appearance of the mask 410, cover or hide small defects or detriments in the EVA foam, and/or increase wear resistance.

The cushion module 414, e.g., the seal 430, includes a rear or proximal wall or surface 432. The rear surface 432 contacts and seals against the user's face in use. In the illustrated embodiment, the cushion module 414 also includes a nasal and oral aperture 434 that receives the user's nose and mouth in use. In some embodiments, the cushion module 414 can include a nasal aperture that receives only the user's nose in use.

In some embodiments, the mask system 400 includes headgear 460 for securing the mask system 400 to the user's face in use. The headgear 460 can operably couple to the mask 410 and the user's head and provide the force needed to obtain an adequate seal between the seal 430 and the user's face in use. Any suitable headgear can be used with the mask 410. In the illustrated embodiment, the headgear 460 includes a top strap 462, side straps 466, and a rear strap 464. The headgear 460 or mask system 400 can also include a neck strap 468.

Figure 23:
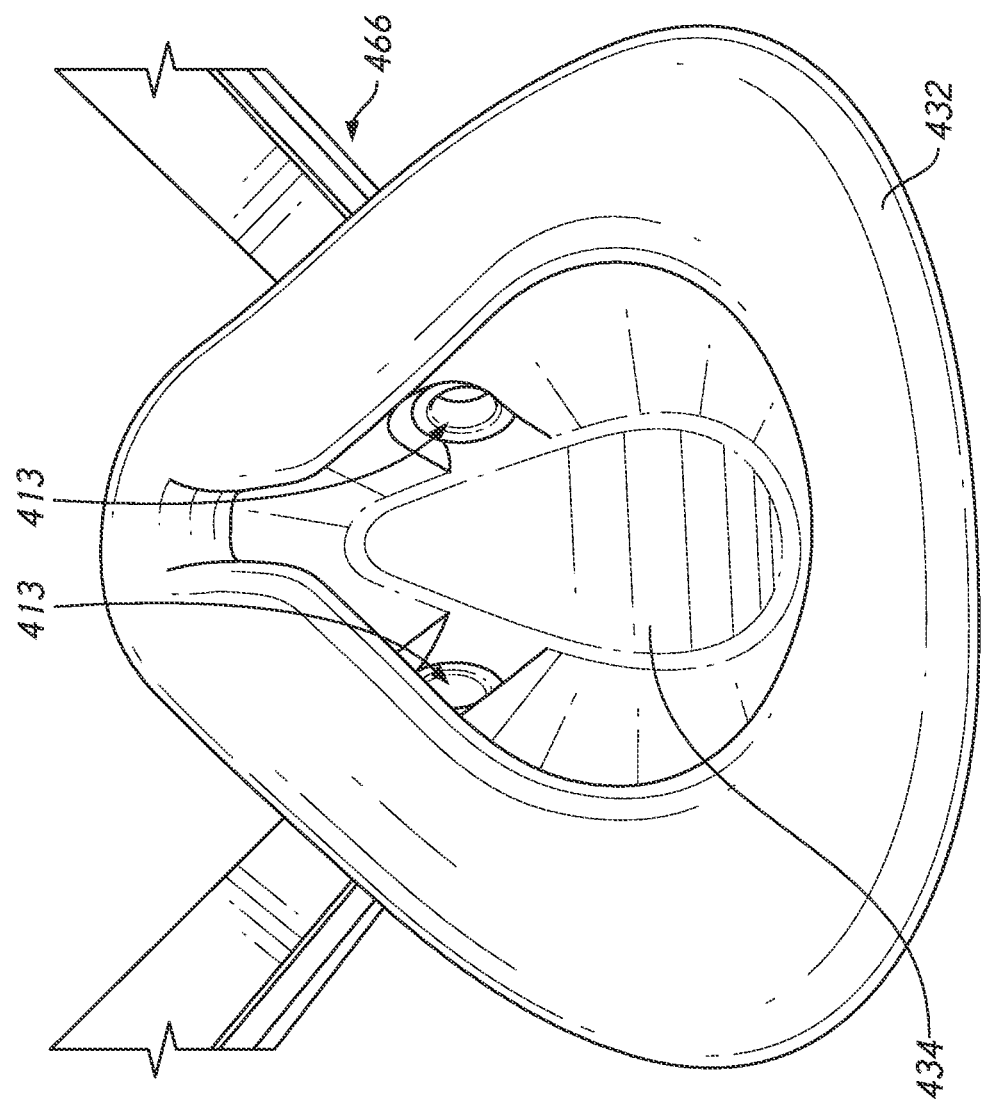
FIG. 23 illustrates a rear view of a mask of the mask assembly of FIG. 18A.

The top strap 462 extends across the top of the user's head in use. The side straps 466 extend from above the ears along or across the user's cheeks towards the user's nose in use as shown. Distal ends of the side straps 466 are coupled to the frame 450. The top strap 462 and side straps 466 can be rigid or relatively rigid. In some embodiments, the top strap 462 and/or side straps 466 can be relatively rigid but capable of a small degree of flexing in a direction perpendicular to the user's head in use. The side straps 466 can be integrally formed with or coupled to ends of the top strap 462. In the illustrated embodiment, an air conduit extends through the top strap 462 and side straps 466. The top strap 462 is coupled to a gas supply conduit in use. In some embodiments, a conduit connector 411 couples the top strap 462 to the gas supply conduit. In some embodiments, the gas supply conduit is coupled to the top strap 462 at or near a central point or portion of the top strap 462 as shown. The side straps 466 include air outlets at or proximate ends of the distal ends of the side straps 466 in portions of the side straps 466 coupled to the frame 450. The mask 410 includes air inlets 413 as shown in FIG. 23. In the illustrated embodiment, the mask 410 includes one air inlet 413 located on each side of the patient's nose in use. In the illustrated embodiment, the air inlets 413 are symmetric about the central plane of the mask 410 (shown in FIG. 20). When the side straps 466 are coupled to the frame 450, the air outlets of the side straps 466 are in fluid communication with the air inlets 413 of the mask 410 such that gases can be delivered from the gas supply conduit, through the air conduit in the top strap 462 and side straps 466, and through the air outlets and air inlets 413 into the mask 410. The air inlets 413 can be positioned such that air flow enters the mask 410 on or near the sides of the patient's nose, which can help direct airflow more directly into the patient's nose and/or mouth rather than into or onto the patient's face, which can help increase or improve patient comfort. The air inlets 413 and therefore location of the connection between the side straps 466 and mask 410 can be positioned such that forces applied by the headgear 460 to the mask 410 cause compression of a deformation region, e.g., a bellows feature 480 (described in greater detail herein) when needed.

Figure 21:
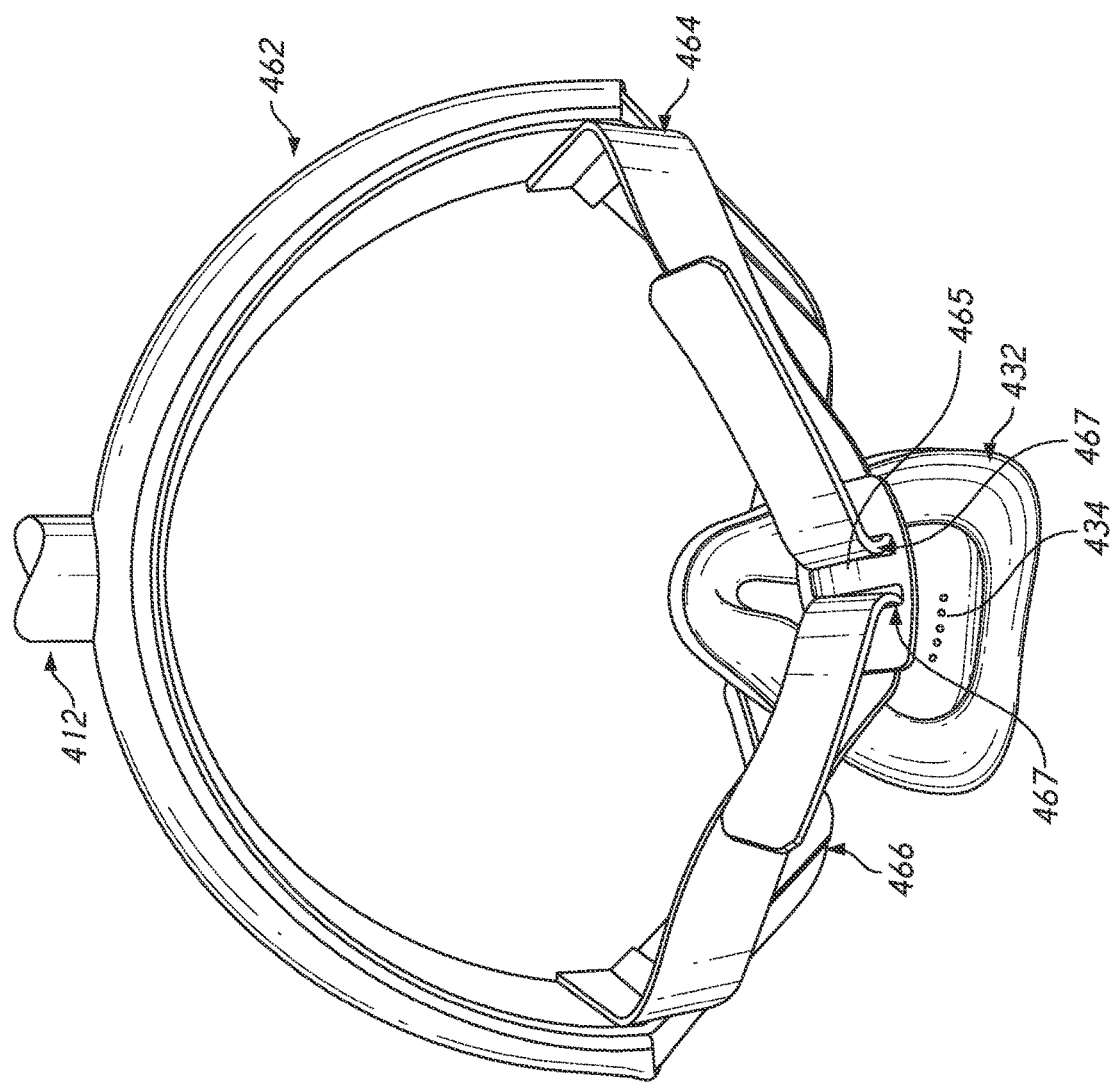
FIG. 21 illustrates a rear view of the mask assembly of FIG. 18A.
Figure 22:
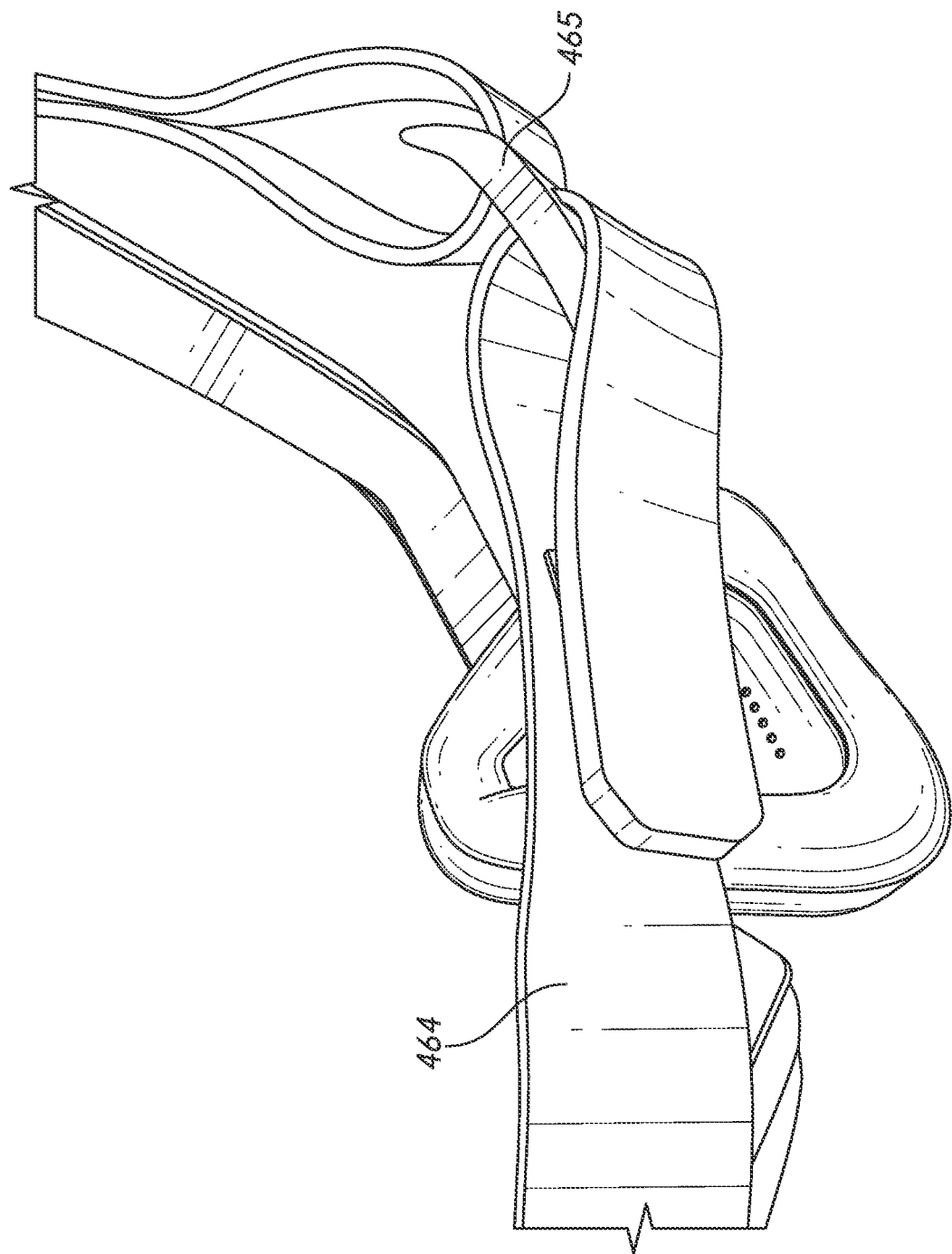
FIG. 22 illustrates a rear strap of a headgear assembly of the mask assembly of FIG. 18A.

The rear strap 464 extends along the back of the user's head in use. In some embodiments, the rear strap 464 is elastic. The rear strap 464 is coupled to the top strap 462 and/or side straps 466. In the illustrated embodiment, the rear strap 464 couples to the top strap 462 and/or side straps 466 at or near junctions between the top strap 426 and side straps 466. As shown in FIG. 21, in the illustrated embodiment, the rear strap 464 includes two portions with one attached to each end of the top strap 462 and/or to one of the side straps 466. The two portions of the rear strap 464 are coupled to each other, for example, via a buckle 465. In the illustrated embodiment, the buckle 465 includes two apertures 467.

To couple the rear strap 464 to the buckle 465, a free or distal end of each of the portions of the rear strap 464 is threaded through one of the apertures 467 (e.g., from a front side of the buckle 465, or a side of the buckle configured to be facing and/or in contact with the patient's head in use, to an opposite back side of the buckle 465) and then looped back on itself so that the distal end or a portion of the strap 464 proximate the distal end can couple to a more proximal portion of the strap 464. The distal end or distal portion of the strap 464 can be releasably coupled or secured to the more proximal portion of the strap 464. For example, in some embodiments, the distal end or distal portion includes the hook or loop part of a hook and loop connector and the more proximal portion includes the other of the hook or loop parts of the hook and loop connector. The straps 464 can be adjusted to adjust the size of the headgear 460 and/or the strap tension on the patient's face.

Figure 25B:
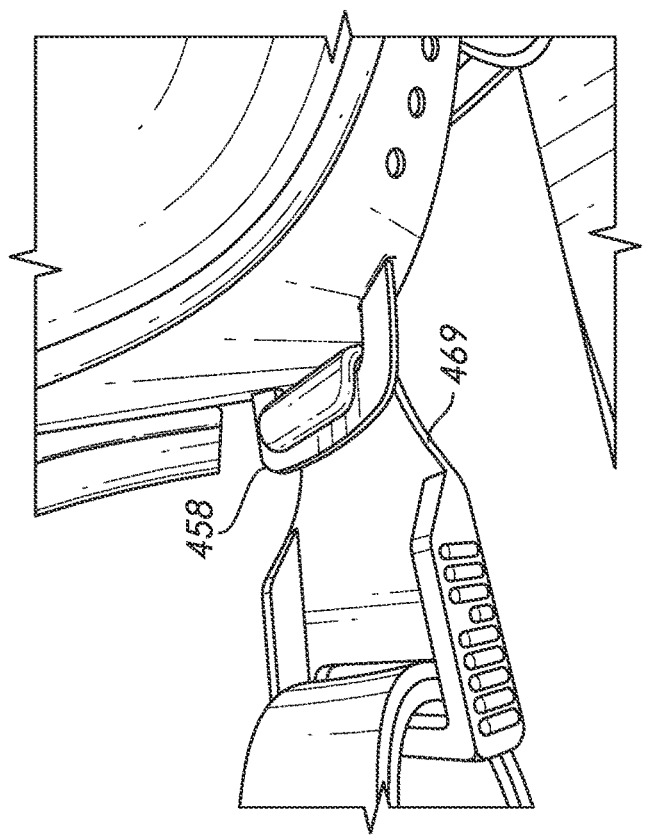
FIG. 25B illustrates a headgear component coupled to the headgear connector of FIG. 25A.
Figure 25A:
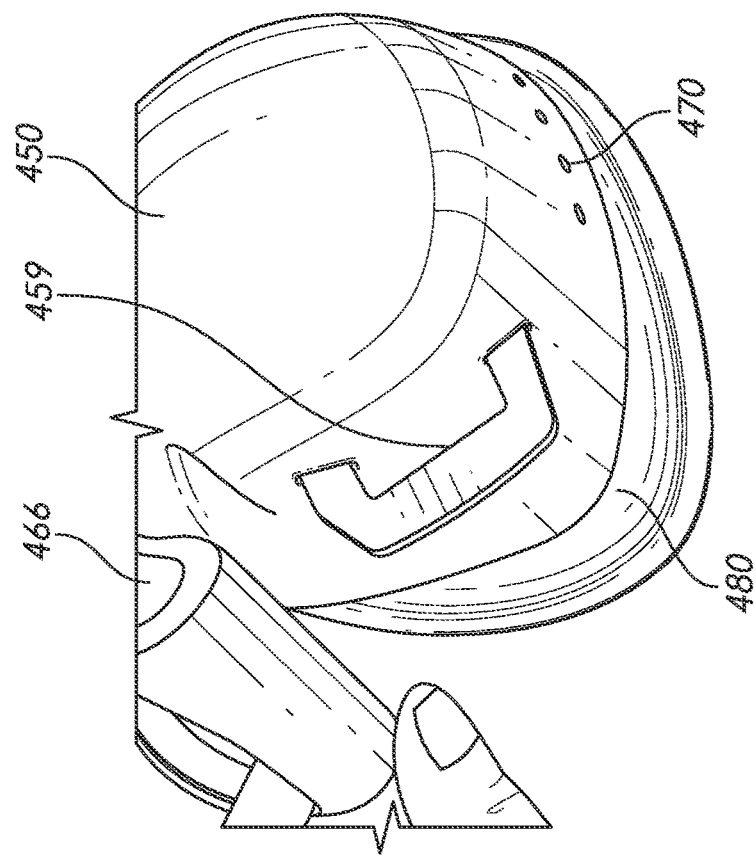
FIG. 25A illustrates a close up of a portion of the mask of FIG. 23 including a headgear connector.

The neck strap 468 can be elastic and/or adjustable. In some embodiments, the neck strap 468 can help support the weight of the mask system 400. The neck strap 468 can help prevent or reduce the likelihood of the bottom of the mask 410 lifting away from the user's face in use, for example, as a result of internal pressure within the mask which produces blow-off forces. In the illustrated embodiment, the frame 450 includes two neck strap connectors 458. The connectors 458 can be permanently attached to the frame 450. Each of the neck strap connectors 458 extends laterally from one side of the frame 450. In other words, the neck strap connectors 458 extend laterally from the sides of the frame 450 in opposing directions. In the illustrated embodiment, the connectors 458 are symmetrical about the central plane as shown in FIG. 20. As shown, the neck strap connectors 458 can be positioned below the connection between the side straps 466 and frame 450. The neck strap 468 can be removably coupled to the connectors 458. In the illustrated embodiment, the connectors 458 form loops or include apertures 459, and ends of the neck strap 468 include or are coupled to hooks 469 that can be removably received in the apertures 459 to removably couple the neck strap 468 to the mask 410 as shown in FIGS. 25A-25B.

Figure 24B:
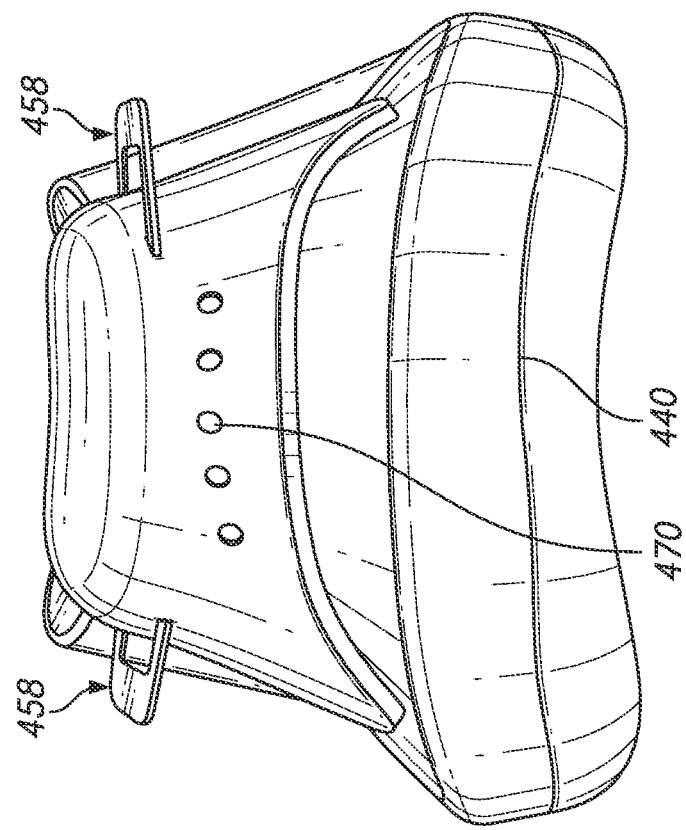
FIG. 24B illustrates a bottom external view of the mask of FIG. 23 showing the bias vent holes.
Figure 24A:
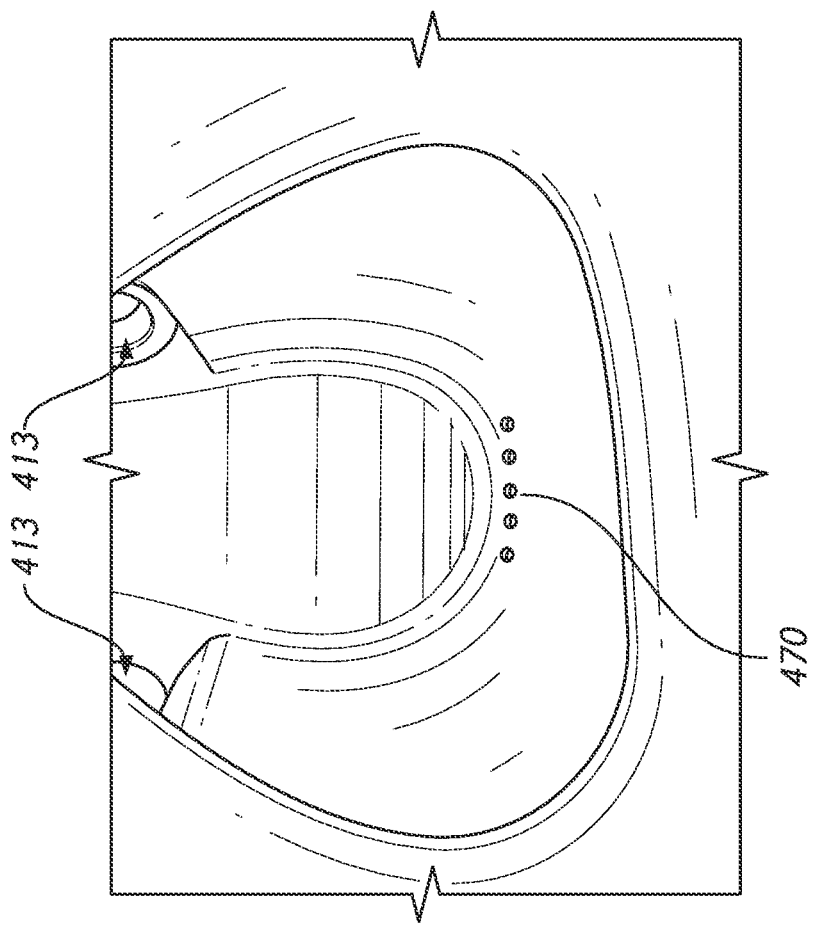
FIG. 24A illustrates an internal view of the mask of FIG. 23 showing bias vent holes.

As shown in FIGS. 20 and 24A-24B, the mask 410 includes bias vent holes 470 to allow for $CO_2$ washout in use. In the illustrated embodiment, the bias vent holes 470 are located along a bottom surface or side of the mask 410. The bias vent holes 470 are apertures that extend through the frame 450 and cushion module 414 and therefore place the inside of the mask 410 in fluid communication with atmosphere outside of the mask 410.

Figure 26B:
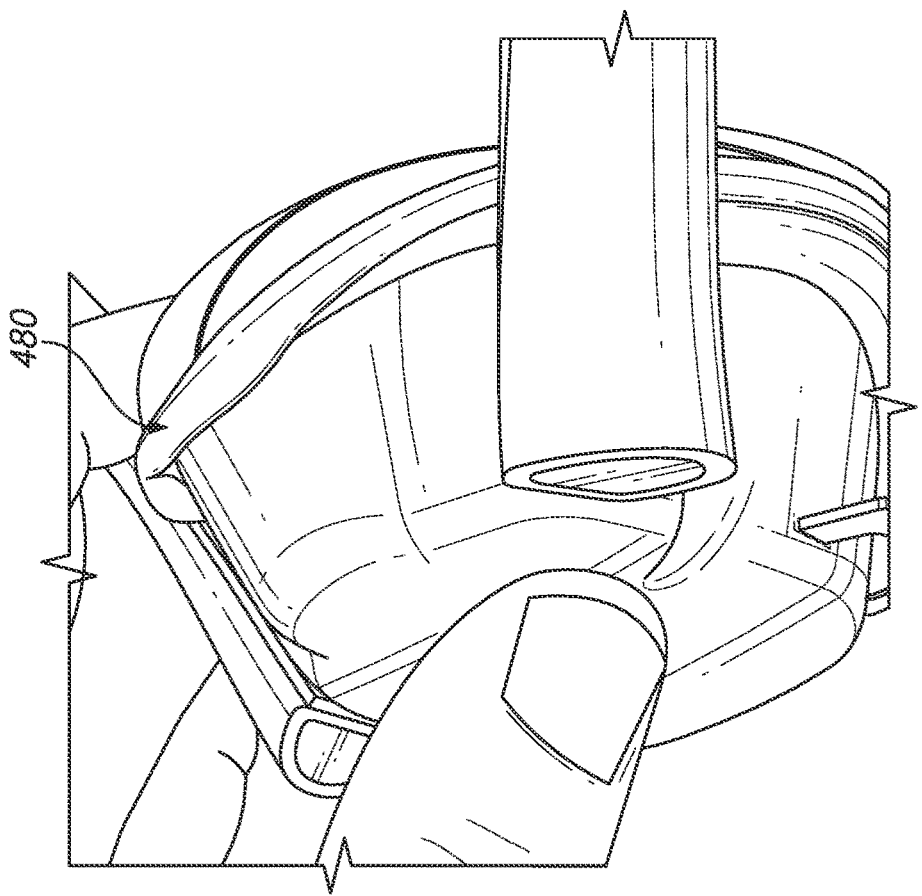
FIG. 26B illustrates the bellows feature of FIG. 26A in a compressed state.
Figure 26A:
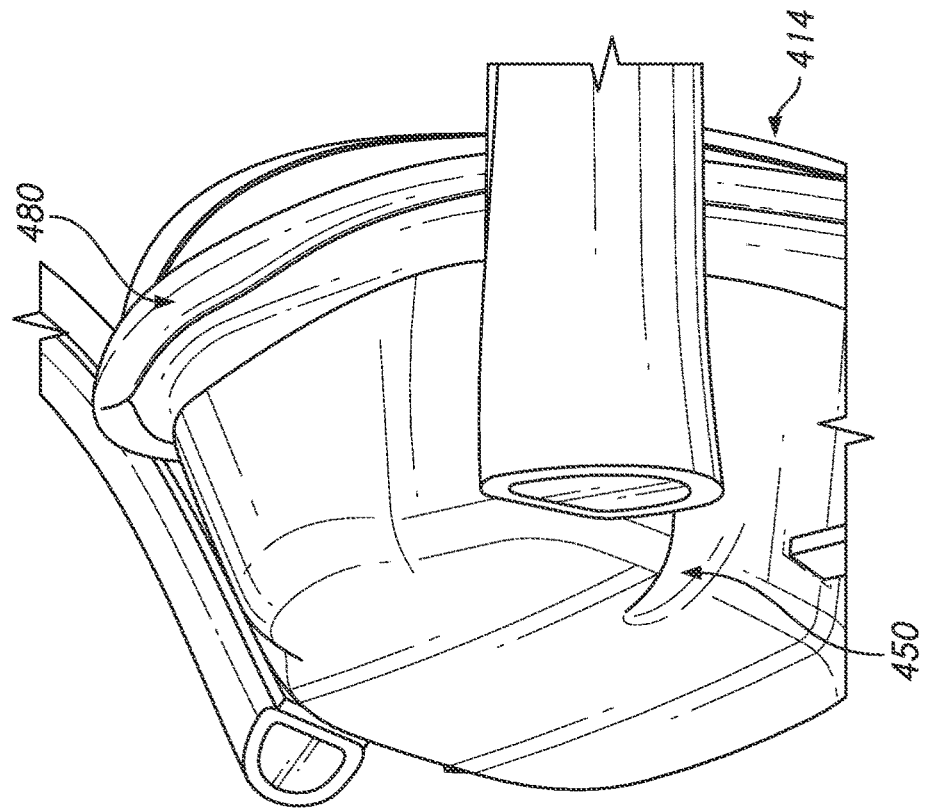
FIG. 26A illustrates a bellows feature of the mask of FIG. 23 in an uncompressed state.

In some embodiments, the mask 410 includes a deformation region, such as a bellows structure 480 or gusset extending around a perimeter of the cushion module 414 as shown in FIGS. 26A-26B. In some embodiments, the bellows structure 480 is inwardly offset from an outer perimeter of the cushion module 414. The bellows structure 480 allows for enhanced compression, relative to a cushion module without a deformation region or bellows structure, of the cushion module 414 and therefore advantageously allows the cushion module 414 to travel, move, or deform relative to the frame 450 to a greater extent than a cushion module without a deformation region or bellows structure in use, for example, to conform to the patient's face and adapt to variations in patient facial geometry. The travel allowed by the bellows structure 480 can advantageously help isolate the cushion module 414 from forces applied to the headgear 460 and/or frame 450 so that forces applied to the headgear 460 and/or frame 450 are less likely to disturb the seal between the cushion module 414 and the user's face. The relatively more rigid frame 450 can advantageously limit the travel of the cushion module 414 and provide support and stability to the mask 410.

Figures 28A, 28B:
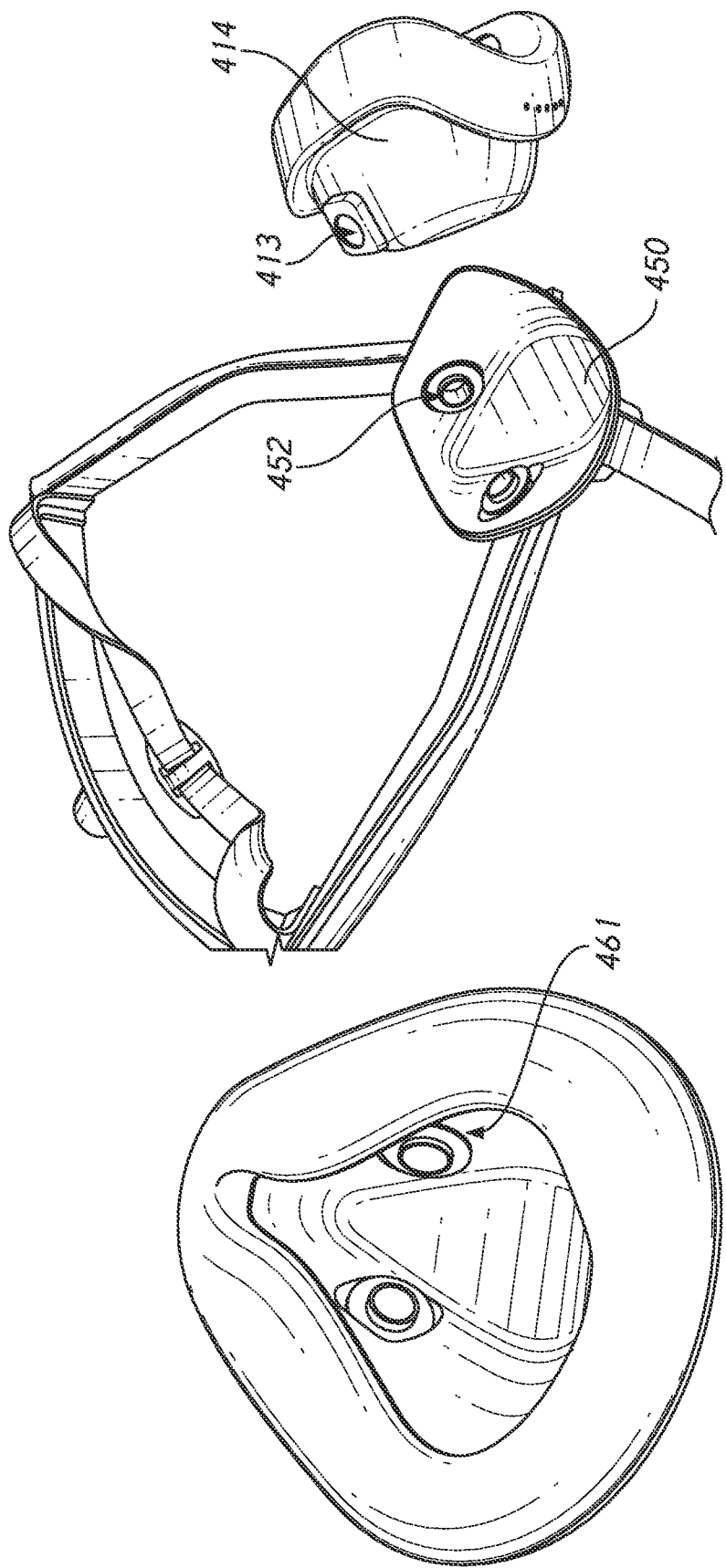
FIG. 28A illustrates a rear view of a mask of an alternative embodiment of the mask assembly of FIG. 18A.
FIG. 28B illustrates a semi exploded view of the mask assembly of FIG. 28A.

FIGS. 27-28B illustrate a variation of the mask system 400. In the illustrated embodiment, the bias vent holes 470 are positioned in and extend through only the cushion module 414. The bias vent holes 470 are positioned closer to the user's face in use compared to the embodiment of FIGS. 18A-26B. Positioning the bias vent holes 470 only in the cushion module 414 can simplify the manufacturing process as it is no necessary to align apertures in the cushion module 414 and frame 450.

In some embodiments, the cushion module 414 is drawn deeper during the manufacturing process (described in greater detail herein), which reduces the thickness of the cushion module 414 and can help the cushion module 414 feel softer and/or more comfortable against the user's face.

In the embodiment of FIGS. 27-28B, the cushion module 414 and frame 450 are removably coupled. This modular construction can allow the cushion module 414 to be disposable and/or replaceable while the headgear 460 and/or frame 450, which may be more wear resistant, can be reused. The modular construction can allow for the creation of different sized and/or customized cushion modules 414 that can be used with the same frame 450 and/or headgear 460.

In use, gases flow through the air conduit 461 in the headgear 460 and inlet apertures 413 into the mask 410, passing through the frame 450 without the gases contacting the frame 450 and/or without the gases entering any space between the frame 450 and cushion module 414.

In some embodiments, the connection between the headgear 460 and frame 450 can include a bearing 452 that allows the frame 450 and cushion module 414 to pivot relative to the headgear 460. This pivoting can allow the cushion module 414 to better conform to the user's face, which can advantageously allow for improved sealing between the cushion module 414 and user's face and/or improved comfort.

Figure 45C:
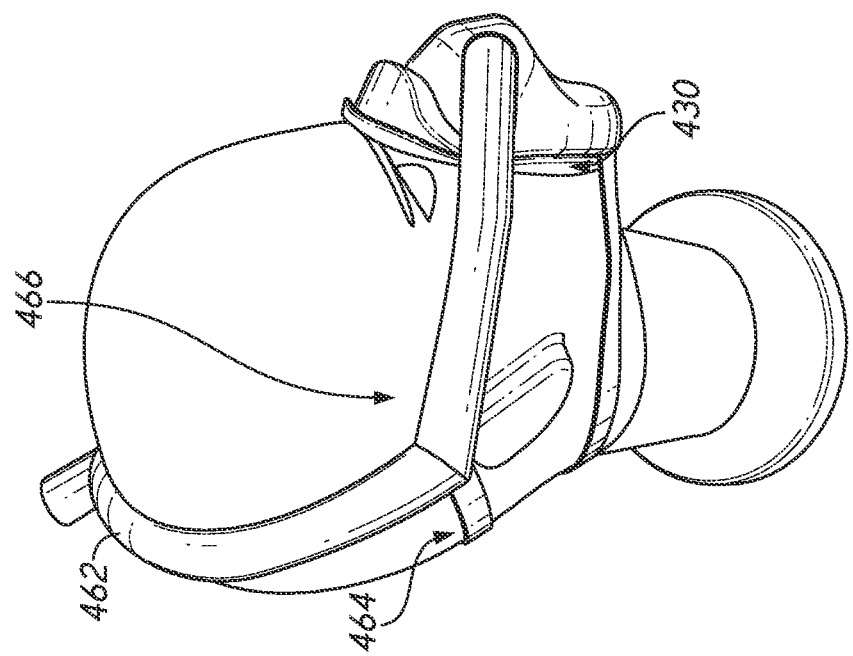
FIG. 45C illustrates a side view of the mask assembly of FIG. 45A.
Figure 45B:
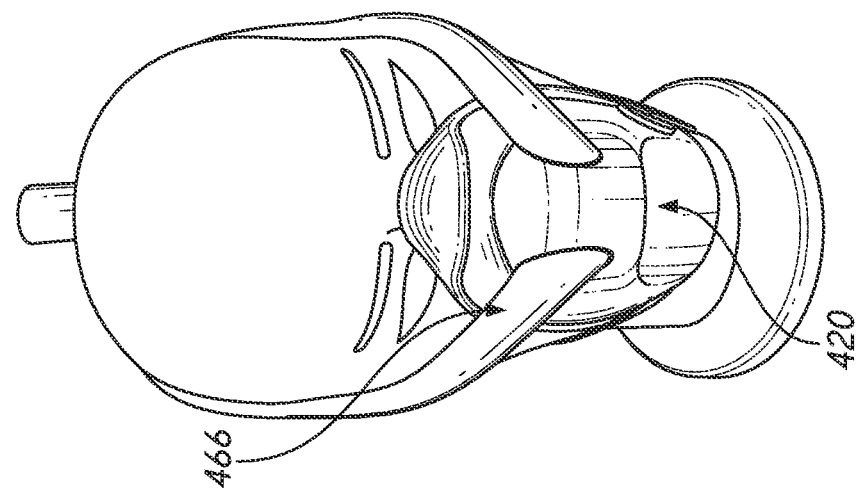
FIG. 45B illustrates a front view of the mask assembly of FIG. 45A.
Figure 45A:
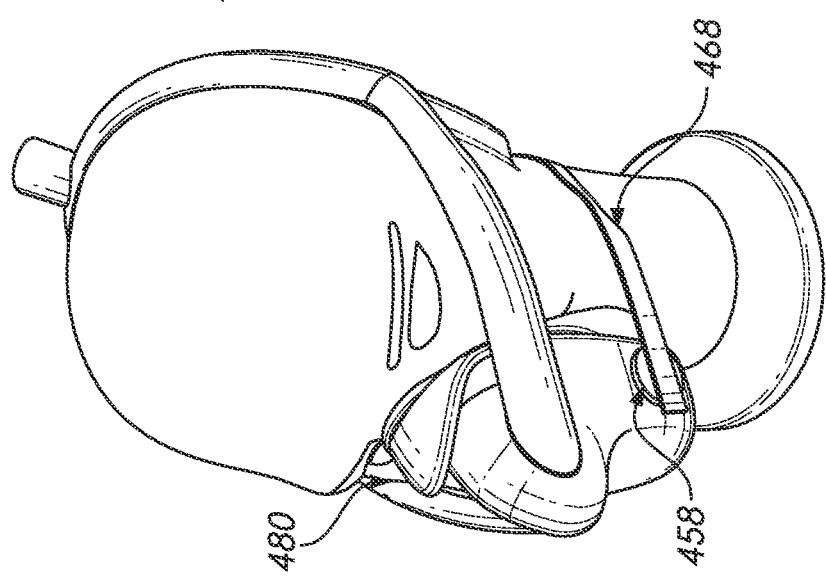
FIG. 45A illustrates a front perspective view of an example embodiment of a mask assembly including thermoformed EVA foam components coupled to a user's face.

FIGS. 45A-45C illustrate another variation of the mask system 400. The mask system 400 of FIGS. 45A-45C may not include a frame. In this embodiment, the shell 420 and seal 430 are made of EVA foam having different densities. In the illustrated embodiment, the shell 420 is made of high density EVA foam. In some embodiments, the shell 420 is made of 3 mm high density EVA foam. Other components of the mask system, such as the headgear, can be made of high density EVA foam. The seal 430 is made of low density EVA foam. In some embodiments, the seal 430 is made of 3 mm low density EVA foam. The seam between the shell 420 and seal 430 can be shifted toward an area of the mask 410 distal to the patient's face, which can advantageously provide for a larger range of seal compression during use to allow for compensation for a variety of different patient face shapes.

In the variation of FIGS. 45A-45C, a deformation region, e.g., a rolling bridge 480, is located along a top portion of a periphery of the mask 410, e.g., on a top and front surface of the mask 410. In this configuration, the rolling bridge 480 can act as or form a hinge that allows a nasal bridge region of the seal 430 to flex, travel, deform or move, e.g., relative to a lower portion of the seal 430, to accommodate varying nasal geometries and/or sizes. In other words, the nasal bridge region of the seal 430 can be designed to roll toward a front or patient-distal side or surface of the mask 410 over and/or onto the front surface of the mask 410, which allows the nasal bridge region of the seal 430 to move in a forward direction relative to the lower portion of the seal 430. In other embodiments, the deformation region can include a bellows feature, which can take the form of a crease extending from one lateral side of the mask 410 to the other. In the illustrated embodiment, the neck strap 468 is removably coupled to the shell 420 via hook and loop connectors. Other connections arrangements, for example as described herein, are also possible. In the illustrated embodiment, a profile of the shell 420, when viewed from the side, includes a protrusion in the upper or nasal region configured to receive the user's nose in use. A lower or chin region of the shell 420 is reduced or stepped back towards the user's face in use compared to the nasal protrusion. The stepped back chin region can help reduce or minimize the size of the mask.

In the embodiment illustrated in FIGS. 45A-45C, the top strap 462 and side straps 466 of the headgear can be made of EVA foam and have a D-shaped cross-section. The top strap 462 and side straps 466 can be hollow and/or include an air conduit to deliver gases from a gas supply conduit to the mask 410 in use. The straight portion of the D-shaped straps can be placed against the patient's face in use. In some embodiments, the straight portion can be made of or include a polyurethane backed fabric. The polyurethane backed fabric can require a decreased thickness compared to the EVA foam and can therefore increase the cross-sectional area of the air flow path within the straps. In some embodiments, the straight portion can include a rigid substrate. For example, the straight portion can be made of or include a polyurethane backed fabric attached to a rigid substrate. In some embodiments, the top 462 and/or side 466 straps can be made of a U-shaped extrusion (e.g., of polyurethane, EVA foam, or another material) with the ends of the "U" attached to a rigid strap or backing to form an air conduit or hollow lumen for an air conduit. In some embodiments, the straight portion can be made of or include foam, such as EVA foam. A rigid substrate or backing and/or foam can help provide the headgear 460 with structure and/or strength, which can help prevent or inhibit the air conduit within the top strap 462 and side straps 466 from collapsing. In the illustrated embodiment, the side straps 466 connect to the nasal protrusion of the shell 420.

Figure 33:
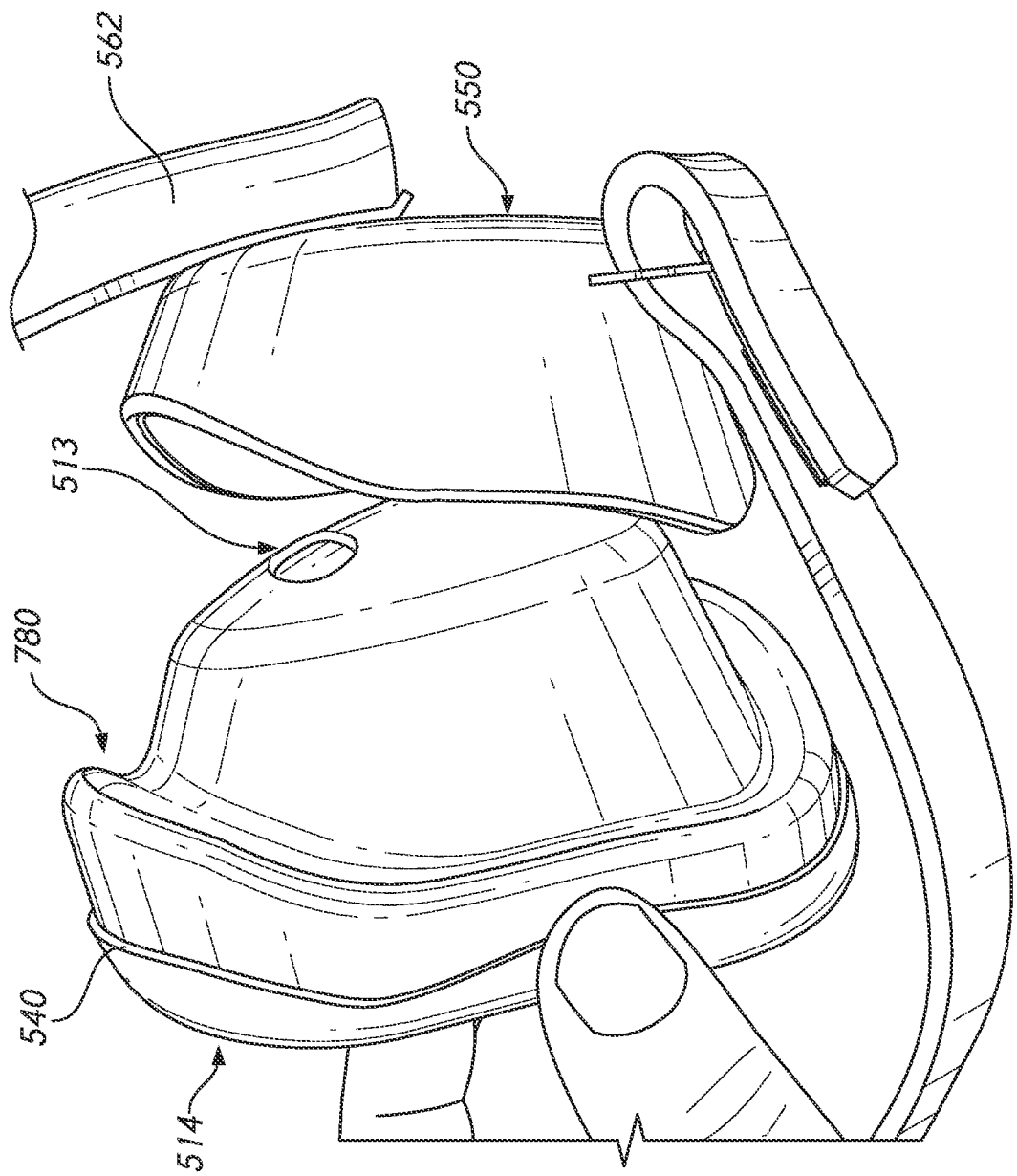
FIG. 33 illustrates an exploded view of the mask assembly of FIG. 29.
Figure 46B:
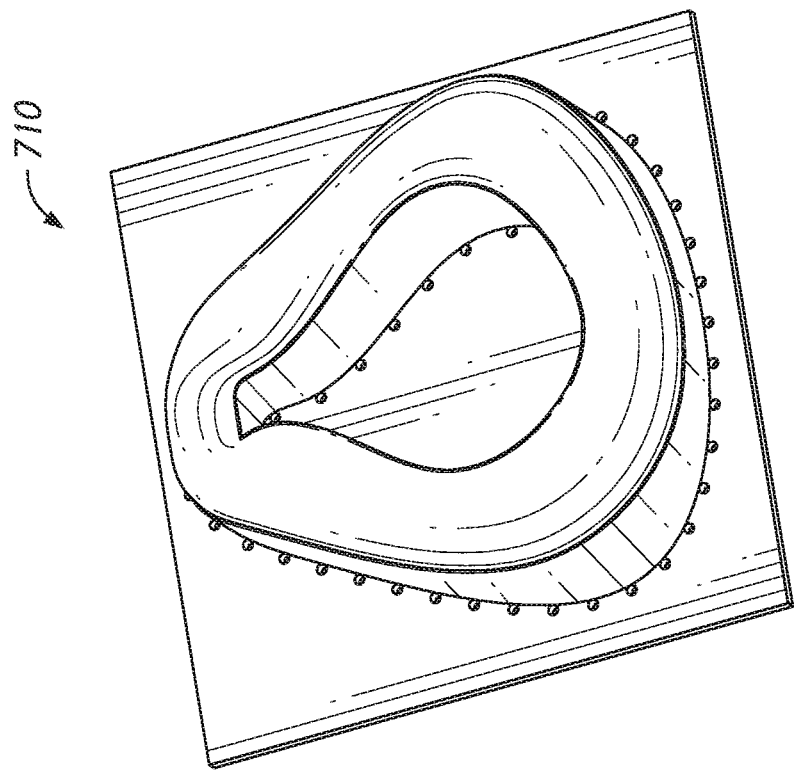
FIG. 46B illustrates a rear view of an example embodiment of a mold tool.
Figure 46A:
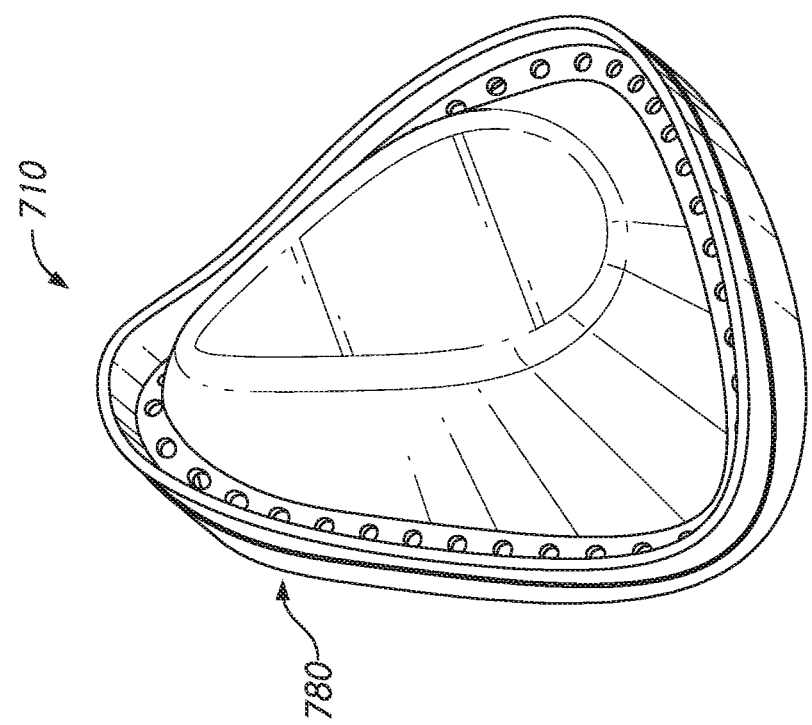
FIG. 46A illustrates a front view of an example embodiment of a mold tool for forming a mask.

FIGS. 46A-46B illustrate an example embodiment of molds 710 for forming a cushion module including a bellows feature that extends around an entire perimeter of the mask, for example, cushion module 514 shown in FIG. 33, which includes a bellows feature 780. The molds 710 can be used to form the seal and shell components of the mask, and the seal and shell components can then be joined together. Both the seal and shell components of a mask formed using molds 710 can be made of soft or low density thermoformed EVA, e.g., 3 mm soft or low density thermoformed EVA. In some embodiments, the mask includes a shell stiffener, for example, an added layer of foam or plastic or a plastic insert, on or in a most forward or distal protrusion or portion of the shell. This construction can advantageously allow for a relatively greater degree of flex in the seal and proximal portion or perimeter of the shell while the remainder of the shell or distal portion of the shell is relatively more rigid. The relatively more flexible portions can act as suspension for the mask and help isolate or decouple movement of the shell from the sealing portion and patient's face. For example, if the shell is pushed upwards, for example, due to upward movement of a gas supply conduit coupled to the mask 710, the bellows feature, e.g., bellows feature 780, can crumple or compress in the top portion of the mask. Similarly, if the shell is pushed downwards or moved side to side, the bellows feature, e.g., bellows feature 780, can crumple or compress in the bottom portion or side portion of the mask, respectively. The bellows feature, e.g., bellows feature 780, can therefore help reduce or eliminate the impact of hose drag and/or allow the patient greater freedom of movement and in sleeping position.

FIGS. 29-37B illustrate an example embodiment of a mask system 500 including a mask 510 having a shell or housing 520, a seal 530, and a frame 550. In the illustrated embodiment, both the shell 520 and seal 530 are made of thermoformed EVA foam. In some embodiments, the shell 520 and seal 530 are made of EVA foam having different densities. The shell 520 and seal 530 can be soft or relatively soft and/or flexible. The flexibility of the shell 520 and/or seal 530 can advantageously allow the mask 510 to adapt or conform to the user's face to form an adequate seal and improve comfort. In some embodiments, the shell 520 and seal 530 are formed separately, e.g., via vacuum thermoforming as described herein, and then joined together at a seam 540. The seam 540 can be similar to seam 240, for example, as shown in and described with respect to any of FIGS. 59-65. The shell 520 and seal 530 together form a cushion module 514.

The frame 550 is coupled to the cushion module 514. In the illustrated embodiment, the frame 550 is coupled to the shell 520 portion of the cushion module 514. The frame 550 can be permanently coupled to the cushion module 514 with any suitable means, for example, using adhesive(s). Alternatively, the frame 550 can be removably coupled to the cushion module 514. In some embodiments, the frame 550 is rigid (or relatively rigid compared to the cushion module 514). The frame 550 can be made of a rigid EVA foam. The rigidity of the frame 550 advantageously provides support to couple, e.g., rigidly couple, various forms and/or components of headgear to the mask 510. Despite the rigidity provided by the frame 550, the EVA foam can still provide a relatively light weight construction and/or some flexibility for the frame 550. The light weight construction of the mask 510 due to the EVA foam construction of the cushion module 514 and/or frame 550 an advantageously reduce the tensile forces needed for headgear (for example, as described herein) to seal the cushion module 514 with the user's face, which can improve patient comfort. In the illustrated embodiment, the frame 550 includes a textile covering. The textile covering can help improve the aesthetic appearance of the mask 510, cover or hide small defects or detriments in the EVA foam, and/or increase wear resistance. In some embodiments, the frame 550 includes or is made of a plurality of layers. The layers can be laminated together to form a composite. One or more of the layers can be made of thermoformed EVA foam as described herein. The layers can be joined together before or after thermoforming. The layers can be laminated together by any suitable means, for example, using adhesive(s) and/or flame lamination. As shown in FIG. 35, the frame 550 can include three layers— an inner first EVA foam layer 554, a middle second EVA foam layer 555, and an outer textile covering layer 556. A multi-layer construction can allow for the construction and manufacturing of frames having more complex geometries and/or different rigidities in different regions of the frame. In other embodiments, the frame 550 can include two, three or more than three layers.

The cushion module 514, e.g., the seal 530, includes a rear or proximal wall or surface that contacts and seals against the user's face in use. In the illustrated embodiment, the cushion module 514 also includes a nasal and oral aperture that receives the user's nose and mouth in use. In some embodiments, the cushion module 514 can include a nasal aperture that receives the user's nose in use.

In some embodiments, the mask system 500 includes headgear 560 for securing the mask system 500 to the user's face in use. The headgear 560 can operably couple to the mask 510 and the user's head and provide the force needed to obtain an adequate seal between the seal 530 and the user's face in use. Any suitable headgear can be used with the mask 510. In the illustrated embodiment, the headgear 560 includes a top strap 562 and a rear strap 564. The headgear 560 or mask system 500 can also include a neck strap 568. The neck strap 568 can be considered to be a pair of side straps. In the illustrated embodiment, the neck strap 568 is a single or unitary strap that extends from one side of the mask 510 around the back of the user's neck in use to the other side of the mask 510 and is removably connected to the mask.

In the illustrated embodiment, an air conduit 561 extends through the top strap 562. In some embodiments, the top strap 562 is made of extruded EVA. In some embodiments, the top strap 562 has a D-shaped cross-section. The top strap 562 can be rigid or relatively rigid compared to other components of the mask system 500. A first end of the top strap 562 is coupled to the frame 550. In use, the top strap 562 extends over the patient's forehead toward or to a top center point of the patient's head. In other words, the top strap 562 extends in line with the patient's nose, between the patient's eyes, and over the forehead and top of the user's head in a front to back direction. This arrangement can allow the top strap 562 to become less noticeable to the patient over time, which can provide a reduced sense of claustrophobia to the patient. This arrangement can allow the gas supply conduit to be hung or draped over the top of the patient's bed (e.g., over the headboard) rather than extending from the side of the bed, which some patients prefer.

The top strap 562 includes or is coupled to a gas supply conduit in use. In some embodiments, a conduit connector 512 couples the top strap 562 to the gas supply conduit. In some embodiments, the gas supply conduit is coupled to the top strap 562 at or near an end of the top strap 562 opposite the end coupled to the frame 550. As shown, the conduit connector 512 and/or connection between the top strap 562 and gas supply conduit can be positioned at or near the top of the patient's head. This placement of the connection to the gas supply conduit can advantageously allow the patient to have an increased range of motion, for example, while sleeping, with a lower risk or likelihood of the gas supply conduit becoming tangled and/or applying displacement or hose drag forces to the mask 510. With existing mask systems, hose pull (the gas supply conduit pulling on the mask) can be a common issue that can cause the seal of the mask 510 to the patient's face to fail.

Figure 34:
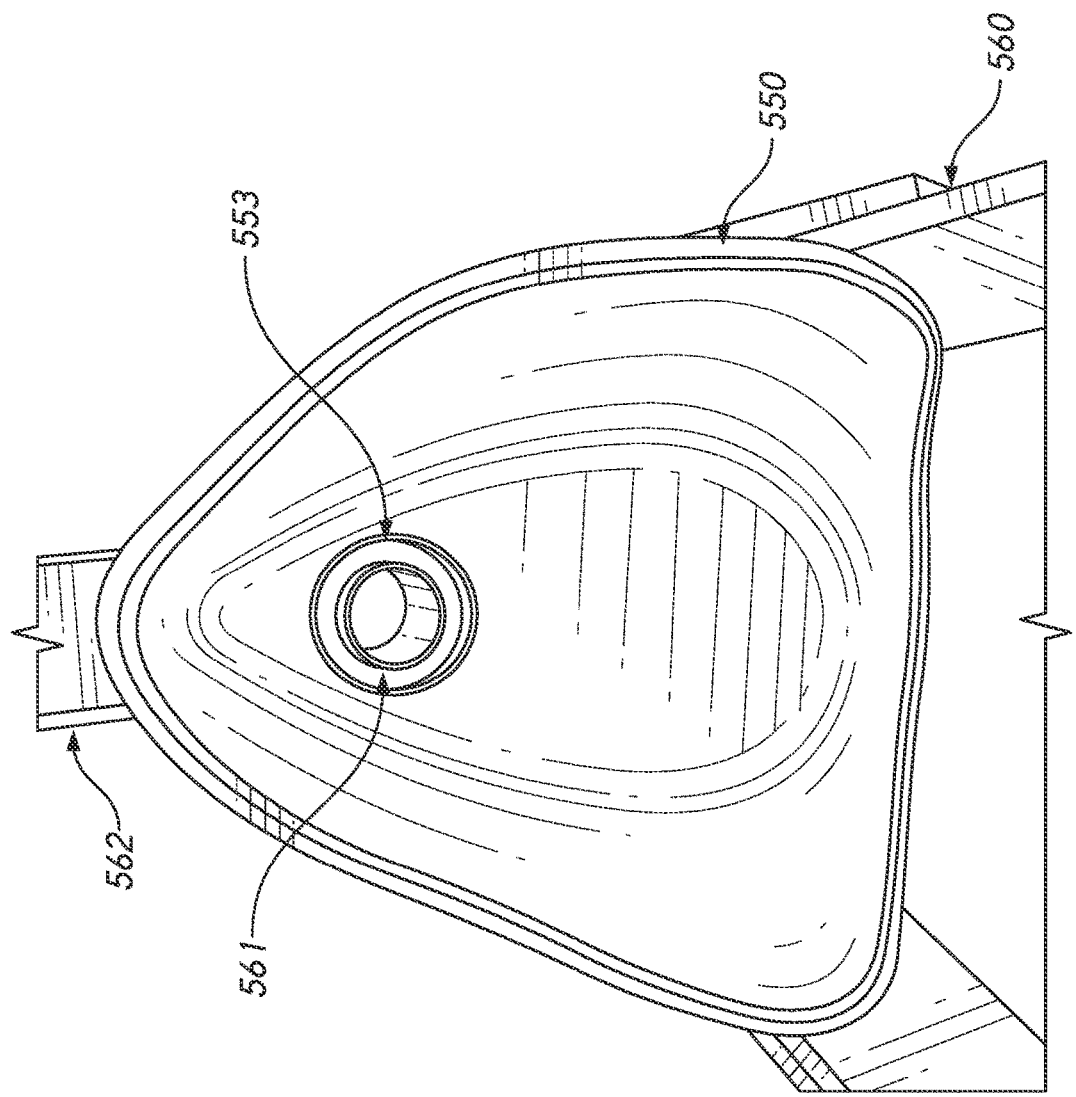
FIG. 34 illustrates a rear view of a frame of the mask assembly of FIG. 29.

The top strap 562 includes an air outlet at or proximate the first end of the top strap 562 in a portion of the top strap 562 coupled to the frame 550. The mask 510 includes an air inlet 513 as shown in FIG. 33. When the top strap 562 is coupled to the frame 550, the air outlet of the top strap 562 is in fluid communication with the air inlet 513 of the mask 510 such that gases can be delivered from the gas supply conduit, through the air conduit 561 in the top strap 562, and through the air outlet and air inlet 513 into the mask 510. In some embodiments, the air conduit 561 passes through the frame 550 (e.g., through an aperture 553 in the frame 550) as shown in FIG. 34 and extends to or into the cushion module 512. In such embodiments, the air conduit 561 does not have to seal with the frame 550. In some embodiments, the mask frame 550 can pivot on, about, and/or with respect to the air conduit 561.

In some embodiments, an extension piece 563 of the top strap 562 extends rearward from the conduit connector 512. The extension piece 563 can be made of extruded EVA. The extension piece 563 can have a D-shaped cross-section. In some embodiments, the extension piece 563 is an extension of the air conduit 561 of the top strap 562. In some embodiments, the air conduit 561 ends or is blocked rearward of the conduit connector 512 such that gases from the gas supply conduit flow into the top strap 562 toward the mask 510 rather than into or toward the extension piece 563.

Figure 37B:
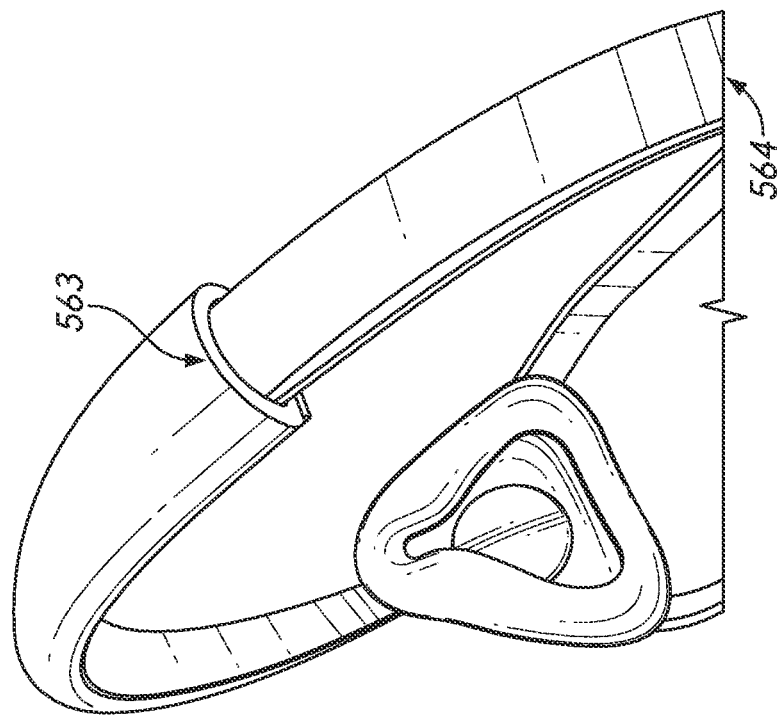
FIG. 37B illustrates an adjustment mechanism of the headgear of the mask assembly of FIG. 29.
Figure 37A:
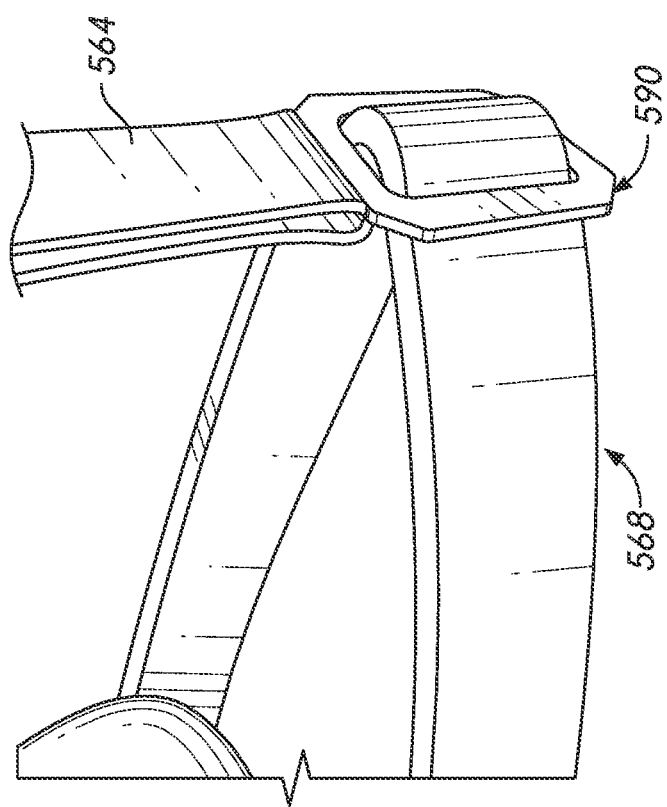
FIG. 37A illustrates a connection between components of a headgear of the mask assembly of FIG. 29.

The rear strap 564 extends vertically or generally vertically along the back of the user's head in use. In some embodiments, the rear strap 564 is rigid and/or non-extensible. A first end of the rear strap 564 is adjustably coupled to the extension piece 563. A second end of the rear strap 564 is coupled to a neck strap 568 at a securing point 569. The rear strap 564 can be removably coupled to the neck strap 568. In some embodiments, the rear strap 564 is semi-permanently coupled to the neck strap 568 via a buckle 590 as shown in FIG. 37A. In the illustrated embodiment, the neck strap 568 is fed through or received in apertures of the buckle 590. The rear strap 564 can telescopingly slide into and out of the extension piece 563 to form a telescopic adjustment mechanism and allow for adjustment of a length of the rear strap 564 and allow for adjustment of the headgear 560 to different sizes and geometries of patients. Once adjusted, the rear strap 564 can be held in place via friction between the rear strap 564 and the internal geometry of the extension piece 563. The user can overcome the friction to adjust the length of the rear strap 564. Alternatively, the rear strap 564 can be adjustable via a variety of mechanisms, for example, a baseball hat style adjustment mechanism, a buckle, or a sliding connection.

In some embodiments, the neck strap 568 is elastic. The neck strap 568 can help support the mask 510 or mask system 500 and/or can help prevent or reduce the likelihood of the mask 510 lifting off the patient's face in use. In some embodiments, the neck strap 568 includes two portions or sides that couple to each other at the securing point 569. In use, the neck strap 568 or two portions of the neck strap 568 extend below the user's ears.

In the illustrated embodiment, the frame 550 includes two neck strap connectors 558. The connectors 558 can be permanently attached to the frame 550. Each of the neck strap connectors 558 extends laterally to a respective side of the frame 550. In some embodiments, the two neck strap connectors 558 are part of a single component that extends across the frame 550. In other embodiments, the two neck strap connectors 558 are individual components, in other words, separate from each other. In the illustrated embodiment, the connectors 558 are symmetrical about the central plane of the mask 510. As shown, the neck strap connectors 558 can be positioned below the connection between the top strap 562 and frame 550. The neck strap 568 can be removably coupled to the connectors 558. In the illustrated embodiment, the connectors 558 form loops or include apertures 559 that are configured to receive the neck strap 568.

In the illustrated embodiment, to couple the neck strap 568 to the frame 550, each of the free or distal ends of the neck strap 568 (or the free ends of the two portions of the neck strap 568) is threaded through one of the apertures 559 from a rear, inner, or proximal side of the connector 558 to a front, outer, or distal side of the connector 558 and then looped back on itself so that the distal end or a portion of the strap 568 proximate the distal end can couple to a more proximal portion of the strap 568. The distal end or distal portion of the strap 568 can be releasably coupled or secured to the more proximal portion of the strap 568. For example, in some embodiments, the distal end or distal portion includes the hook or loop part of a hook and loop connector and the more proximal portion includes the other of the hook or loop parts of the hook and loop connector. The neck strap 568 can be adjustably connected to the frame 550 to adjust a length of the strap 568, size of the headgear 560, and/or tensile force(s) exerted on the patient.

As shown in FIG. 33, the cushion module 514 and frame 550 are removably coupled. For example, as described herein and shown in FIG. 34, in some embodiments, the air conduit 561 passes through the frame 550 (e.g., through an aperture 553 in the frame 550) and extends to or into the cushion module 512. In some such embodiments, the portion of the air conduit 561 that extends through the frame 550 can include one or more retention features that secure the air conduit 561, and therefore the frame 550 through which the air conduit 561 extends, to the cushion module 514. For example, the air conduit 561 can include a lip extending radially outward from the air conduit 561 at or near the outlet or end of the air conduit 561, and the air inlet 513 of the cushion module 514 can be stretched over the lip to assemble the cushion module 514 and frame 550. A modular construction in which the cushion module 514 and frame 550 are removably coupled can allow the cushion module 514 to be disposable and/or replaceable while the headgear 560 and/or frame 550, which may be more wear resistant, can be reused. The modular construction can allow for the creation of different sized and/or customized cushion modules 514 that can be used with the same frame 550 and/or headgear 560.

Figure 32:
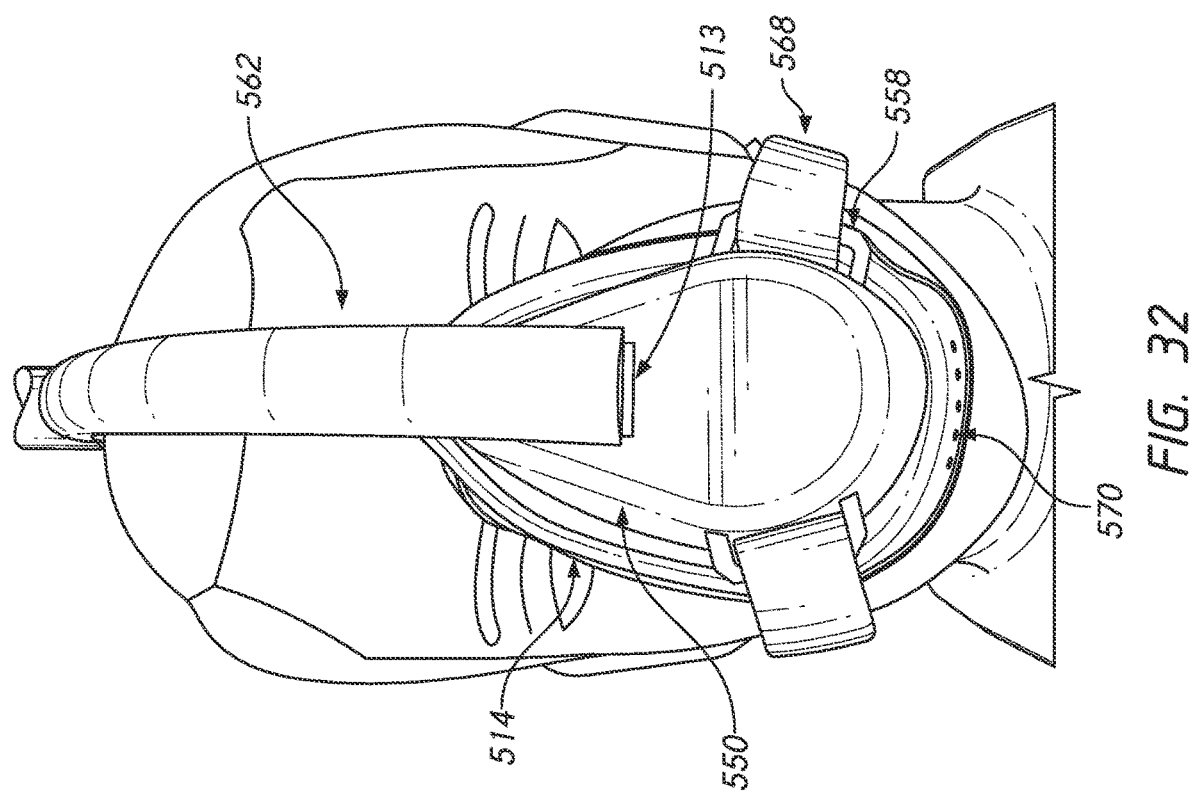
FIG. 32 illustrates a front view of the mask assembly of FIG. 29.

In some embodiments, the frame 550 includes one or more bias vent holes. In some embodiments, the bias vent holes extend through the EVA foam, but do not extend through the textile covering of the frame 550. The textile covering can advantageously hide or obscure the bias vent hole from view, which can improve the aesthetics of the mask 510. The textile covering can help diffuse air flow that passes through the bias vent hole as the air flow exits the mask 510, which may reduce any noise or draft the patient or their bed partner may experience. In some embodiments, the cushion module 514 can include one or more bias vent holes 570, for example as shown in FIG. 32.

FIGS. 48-58 illustrate an example embodiment of a mask system 900 including a mask 910 having a shell or housing 920, a seal 930, and a frame 950. In this embodiment, the frame 950 is positioned or disposed between the housing 920 and the seal 930. In the illustrated embodiment, both the shell 920 and seal 930 are made of foam, e.g., thermoformed EVA foam. In some embodiments, the shell 920 and seal 930 are made of foam, e.g., EVA foam, having portions with different densities. The portions with different densities may be different types of foam or the same type of foam. The shell 920 and/or seal 930 can be soft or relatively soft and/or flexible. The flexibility of the shell 920 and/or seal 930 can advantageously allow the mask 910 to adapt or conform to the user's face to form an adequate seal and improve comfort.

The frame 950 is coupled, e.g., permanently or removably, to the housing 920 and seal 930. The housing 920 is coupled to a front or patient-distal side of the frame 950, and the seal 930 is coupled to a rear or patient-proximal side of the frame 950. In some embodiments, the housing 920 is permanently coupled to the frame 950 and the seal 930 is removably attached to the frame 950, for example, so that the seal 930 can be replaced if needed or desired. The housing 920 can include a scalloped perimeter 922 adjacent to or extending from the frame 950. The scalloped perimeter 922 can help isolate movement of the housing 920 from movement of the seal 930 and/or frame 950. This allows the housing 920 to deform relative to the frame 950, for example, when the housing 920 contacts bedding or the user's sleeping partner, to inhibit or reduce the likelihood of the seal 930 becoming dislodged from the user's face.

Figure 53:
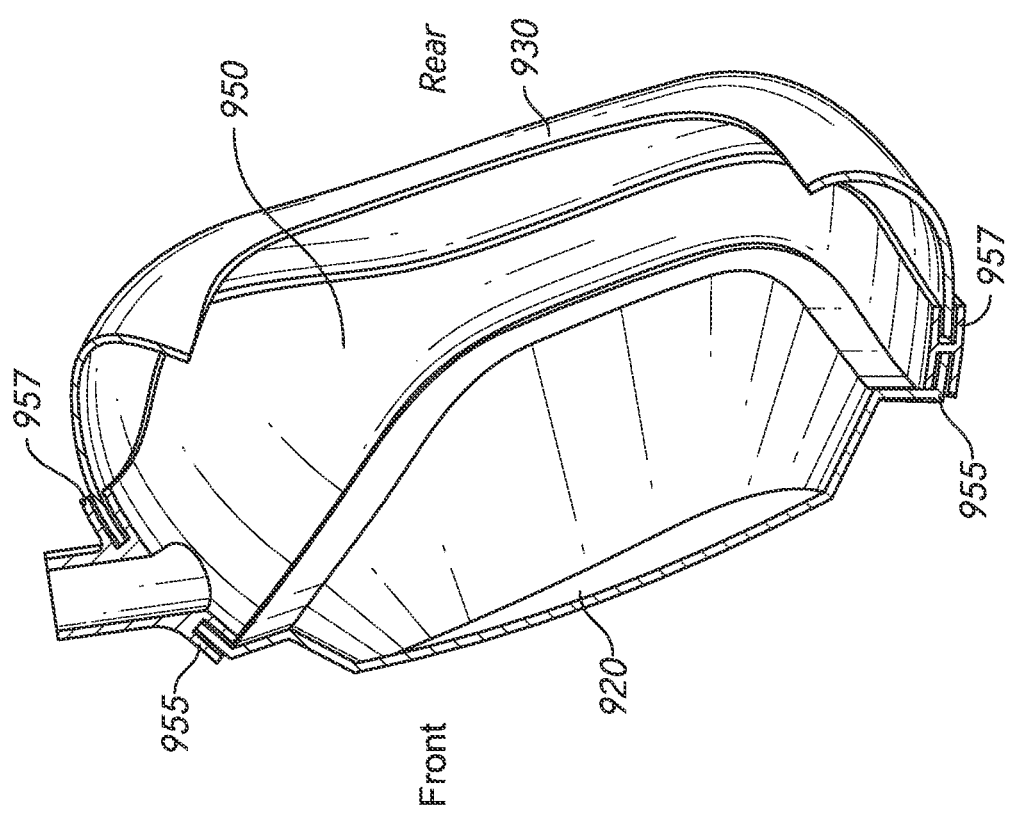
FIG. 53 illustrates a side cross-sectional view of the mask of FIG. 48.

Either or both of the housing 920 and seal 930 can be coupled to the frame 950 via a tongue-and-groove connection. The housing 920 and seal 930 therefore do not extend through the entire thickness of the frame 950. As shown in FIG. 53, the frame 950 can include a front channel 955 that opens forwardly or patient-distally and/or a rear channel 957 that opens rearwardly or patient-proximally. The front 955 and/or rear 957 channel can extend around a portion or an entirety of a perimeter of the frame 950. The front channel 955 receives a rear edge of the housing 920. The rear channel 957 receives a front edge of the seal 930. The housing 920 and/or seal 930 can be retained in the front 955 and/or rear 957 channel, respectively, via a friction fit, adhesive, or other appropriate retention means.

Figure 54C:
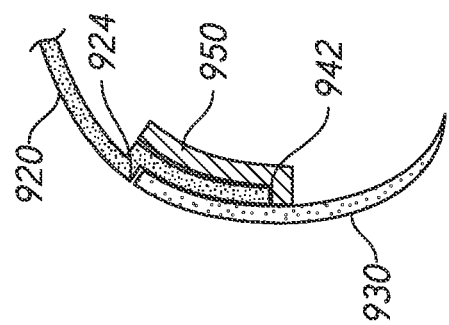
FIGS. 54A, 54B, and 54C illustrate schematic cross-sectional views of alternative couplings of the frame with the housing and seal of the mask of FIG. 49.
Figure 54B:
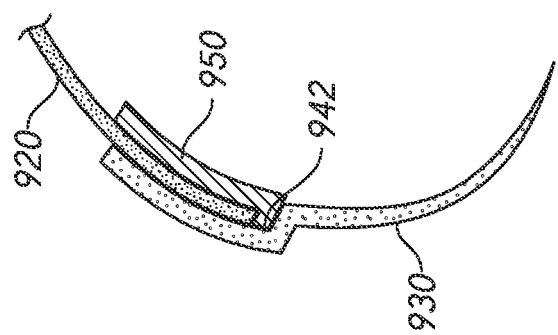
Figure 54A:
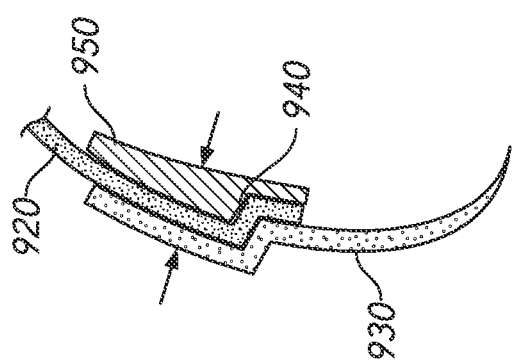

FIGS. 54A-54C show alternative connections among the frame 950, housing 920, and seal 930. In the illustrated embodiments, the seal 930 and housing 920 are stretched over the frame 950. For example, the seal 930 and/or housing 920 can have an inner perimeter (e.g., of the front edge of the seal 930 and/or the rear edge of the housing 920) that is the same or approximately the same size (e.g., diameter or circumference) as or smaller than an outer perimeter of the frame 950. The seal 930 and/or housing 920 are therefore in tension when fitted over the frame 950 and apply an inwardly-directed force to the frame 950. The tension and inwardly-directed force on the frame 950 retain the seal 930 and/or housing 920 on the frame 950. The housing 920 can be sandwiched between the frame 950 and the seal 930 as shown. Alternatively, the seal 930 can be sandwiched between the housing 920 and the frame 950. The seal 930 and/or housing 920 can be permanently coupled to the frame 950, for example, via an adhesive, welding, or other suitable means, instead of or in addition to be stretched over the frame 950. In some embodiments, the housing 920 is permanently coupled to the frame 950 and the seal 930 is removably coupled to the frame 950, for example, to allow for replacement of the seal 930 as needed or desired.

In the embodiment of FIG. 54A, the outer surface of the frame 950 includes an inward step 940 proximate the seal 930 end of the frame 950 such that a portion of the frame 950 adjacent the seal 930 or patient-proximal end of the frame is thinner than a remainder of the frame 950. The step 940 can help align and/or retain the housing 920 and/or seal 930 on the frame 950 when the breathing chamber inside the mask 910 is pressurized in use. The inner perimeter of the seal 930 and/or housing 920 can be approximately the same size as or smaller than the outer perimeter of the thin portion of the frame 950 so that the seal 930 and/or housing 920 engages the thin portion. In some embodiments, the housing 920 and/or seal 930 can have outwardly stepped contours that correspond to the contour of the step 940 of the frame 950 as shown to help retain the seal 930 and/or housing 920 on the frame 950.

In the embodiment of FIG. 54B, the frame 950 includes an outwardly-projecting lip 942 at or near the seal 930 or patient-proximal end of the frame 950. The lip 942 can help align and/or retain the housing 920 and/or seal 930 on the frame 950. The edge of the housing 920 can abut the lip 942 when coupled to the frame 950 as shown. The seal 930 can have an outwardly stepped contour as shown to allow the seal 930 to extend over the lip 942 and housing 920. In other embodiments, the seal 930 can be sandwiched between the frame 950 and the housing 920, the lip 942 can be positioned at or near the housing 920 or patient-distal end of the frame 950, the frame end or patient-distal edge of the seal 930 can abut the lip 942, and the housing 920 can have an outwardly stepped contour to allow the housing 920 to extend over the lip 942 and seal 930.

In the embodiment of FIG. 54C, the frame 950 includes a lip 942 similar to the embodiment of FIG. 54B. The housing 920 includes an inward step 924 such that a portion of the housing 920 adjacent the frame 950 or patient-proximal end of the housing 920 has a reduced perimeter or diameter. The housing 920 is sized such that the reduced perimeter portion engages the outer surface of the frame 950 and the frame 950 or patient-proximal edge of the housing 920 abuts the lip 942 of the frame 950. The seal 930 extends over the housing 920, and the frame or patient-distal edge of the seal 930 abuts the step 924 of the housing 920. Such a configuration allows the housing 920 and seal 930 to form an outer surface of the mask 910 having an overall continuous contour as shown. In other embodiments, the housing 920 and seal 930 can be reversed such that the seal 930 is sandwiched between the frame 950 and the housing 920, the lip 942 of the frame 950 is at or near the housing 920 or patient-distal end of the frame 950, the seal 930 includes an inward step, the frame or patient-distal edge of the seal 930 abuts the lip 942 of the frame 950, the housing 920 extends over the seal 930, and the frame or patient-proximal edge of the housing 920 abuts the step of the seal 930.

Figure 50:
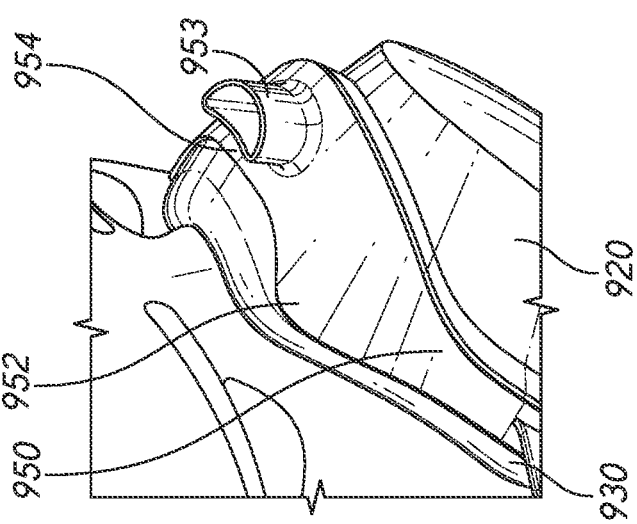
FIG. 50 illustrates a partial top perspective view of the mask of FIG. 49.
Figure 49:
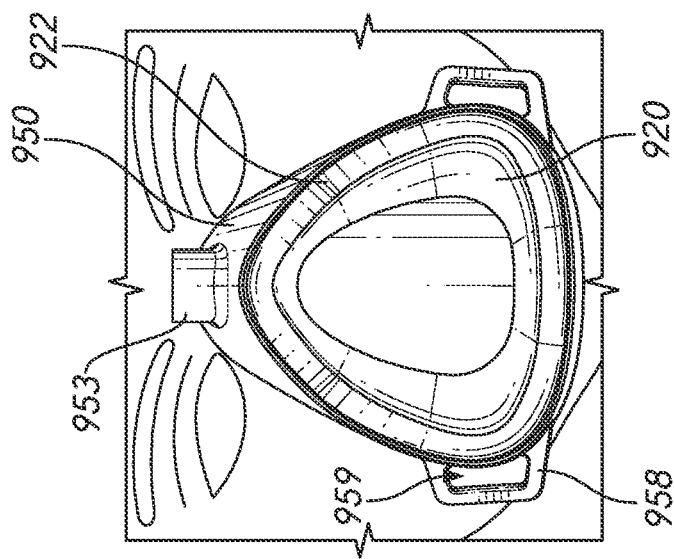
FIG. 49 illustrates a front view of a mask of the mask assembly of FIG. 48.
Figure 52:
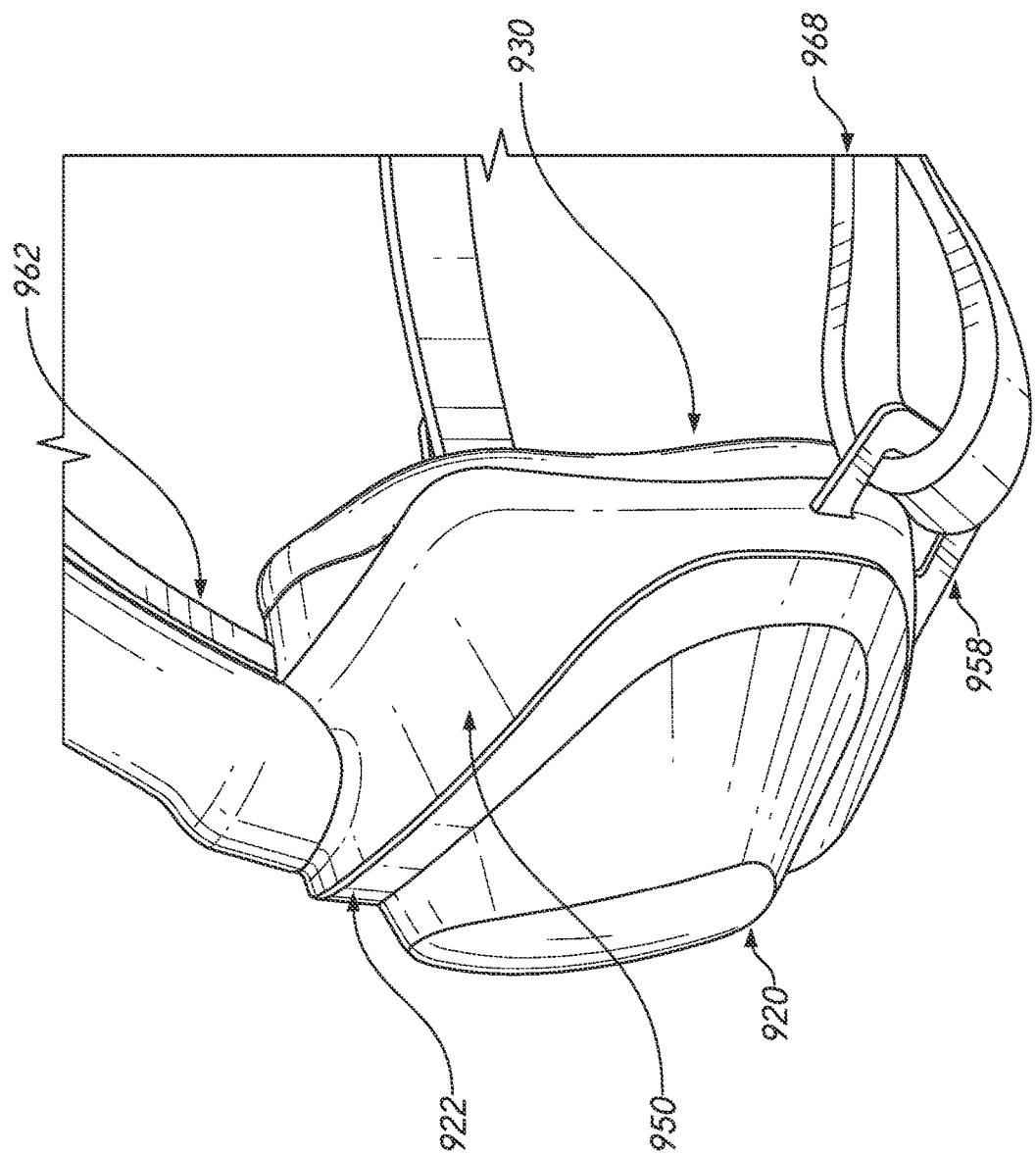
FIG. 52 illustrates a side perspective view of the mask assembly of FIG. 48.

In some embodiments, the frame 950 is rigid (or relatively rigid compared to the housing 920 and/or seal 930). The frame 950 can be made of a rigid EVA foam. The frame 950 can be made of or include polycarbonate. The frame 950 can be transparent or opaque. The frame 950 can advantageously act as a joiner between the housing 920 and seal 930 and/or provide support to the mask 910. The frame can be shaped to provide structure or support to the upper cheek areas of the seal 930 by following the contour of the sealing surface and extending toward the user's face in use on either side of the nasal bridge to form a cheek support 952, as shown in FIG. 50. This structure or support can help reduce the likelihood of leaks into the user's eyes, for example, by providing an increased seal and/or conformity to the user's face in use. The frame 950 can include a relieved or cutaway region in the nasal bridge area (a nasal bridge relief 954) and/or the chin area (a chin relief 956) so that the seal 930 has more room to move and/or deform in those areas to allow greater conformability to the user's facial geometry. This can help improve the seal with the user's face and/or user comfort.

The frame 950 can include headgear connectors 958, for example, for a lower headgear strap 968 as described herein. The frame 950 can also or alternatively include connectors for upper headgear strap(s). For example, the frame 950 can include connectors for both lower headgear strap(s) and upper headgear strap(s) to allow for connection of a four point headgear. The illustrated embodiment includes two headgear connectors 958, one extending laterally to each side of the frame 950. The headgear connectors 958 can form loops or include apertures 959 as shown. In use, the apertures 959 receive the lower headgear strap 968, e.g., ends of the lower headgear strap 968. The frame 950 can include a conduit connection 953, for example, for an air conduit extending within a top headgear strap 962 as described herein. In the illustrated embodiment, the conduit connection 953 extends upwardly from an apex of the frame 950. The conduit connection 953 surrounds and defines an aperture through the frame 950 that provides fluid communication with an interior of the mask 910, which forms a breathing chamber. In the illustrated embodiment, the conduit connection 953 is generally D-shaped or crescent-shaped.

The mask system 900 can include headgear 960 for securing the mask system 900 to the user's face in use. The headgear 960 can operably couple to the mask 910 and the user's head and provide the force needed to obtain an adequate seal between the seal 930 and the user's face in use. Any suitable headgear can be used with the mask 910. In the illustrated embodiment, the headgear 960 includes a top strap 962, a lower strap 968, and a rear strap 964.

In the illustrated embodiment, an air conduit extends through or along the top strap 962. In some embodiments, the top strap 962 is made of extruded EVA. The extruded EVA can be backed with a fabric-wrapped rigid plastic. The top strap 962 can have a D-shaped cross-section. In some embodiments, the top strap 962 is thermo-formed into a curve to follow or accommodate the user's head profile. A first end of the top strap 962 is coupled to the frame 950, e.g., to the conduit connection 953, such that the air conduit is in fluid communication with an interior of the mask 910. A second, opposite end of the top strap 962 is coupled to a gas supply conduit in use, for example, via a supply connection 963 at the second end of the top strap 962. In use, the top strap 962 extends from the first end over the patient's forehead toward or to a top center point of the patient's head. In other words, the top strap 962 extends in line with the patient's nose, between the patient's eyes, and over the forehead and top of the user's head in a front to back direction. This arrangement can allow the top strap 962 to become less noticeable to the patient over time, which can provide a reduced sense of claustrophobia to the patient. This arrangement can allow the gas supply conduit to be hung or draped over the top of the patient's bed (e.g., over the headboard) rather than extending from the side of the bed, which some patients prefer.

The lower strap 968 extends under the user's ears and around the back of the user's head in use. The lower strap 968 can be made of an elastic material. To couple the lower strap 968 to the frame 950, each of the free ends of the lower strap 968 is threaded through one of the apertures 959 of one of the headgear connectors 958 from a rear, inner, or proximal side of the connector 958 to a front, outer, or distal side of the connector 958 and then looped back on itself so that the distal end of a portion of the strap 968 proximate the distal end can couple to a more proximal portion of the strap 968. The distal end or distal portion of the strap 968 can be releasably coupled or secured to the more proximal portion of the strap 968. For example, in some embodiments, the distal end or distal portion includes one component or half of a hook and loop connector and the more proximal portion includes the other half or component of a hook and loop connector. The lower strap 968 can therefore be adjustably connected to the frame 950 to adjust a length of the strap 968, size of the headgear 960, and/or tensile force(s) exerted on the patient.

Figure 48:
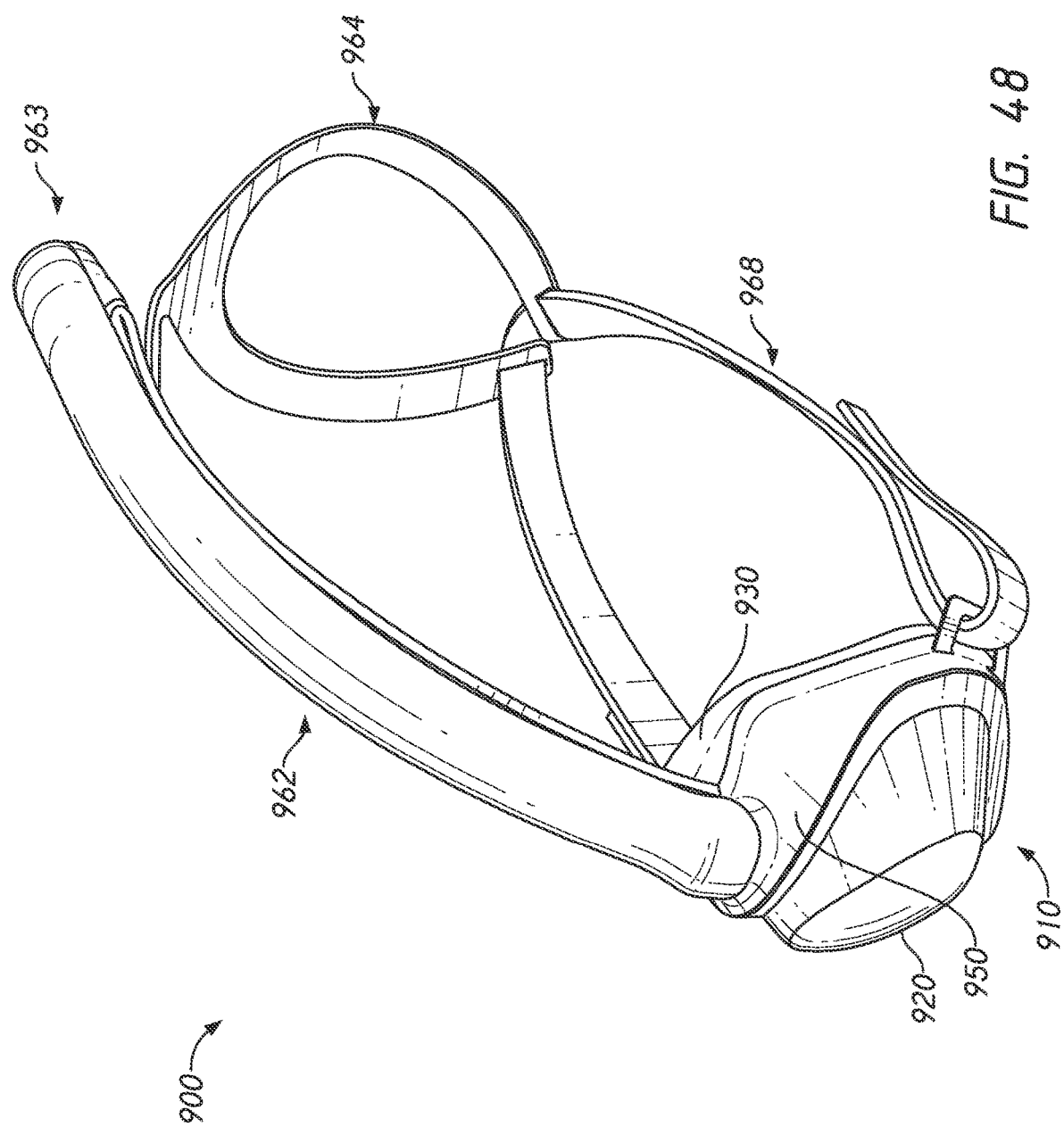
FIG. 48 illustrates a side perspective view of an example embodiment of a mask assembly including thermoformed EVA components coupled by a frame.
Figure 51:
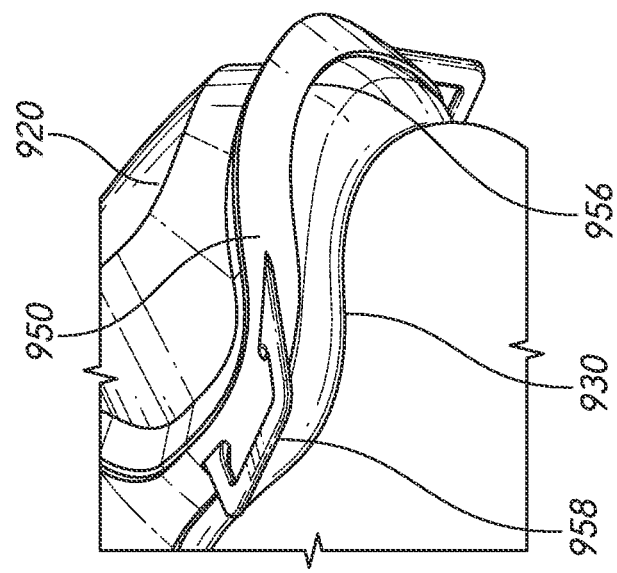
FIG. 51 illustrates a partial bottom perspective view of the mask of FIG. 49.
Figure 55:
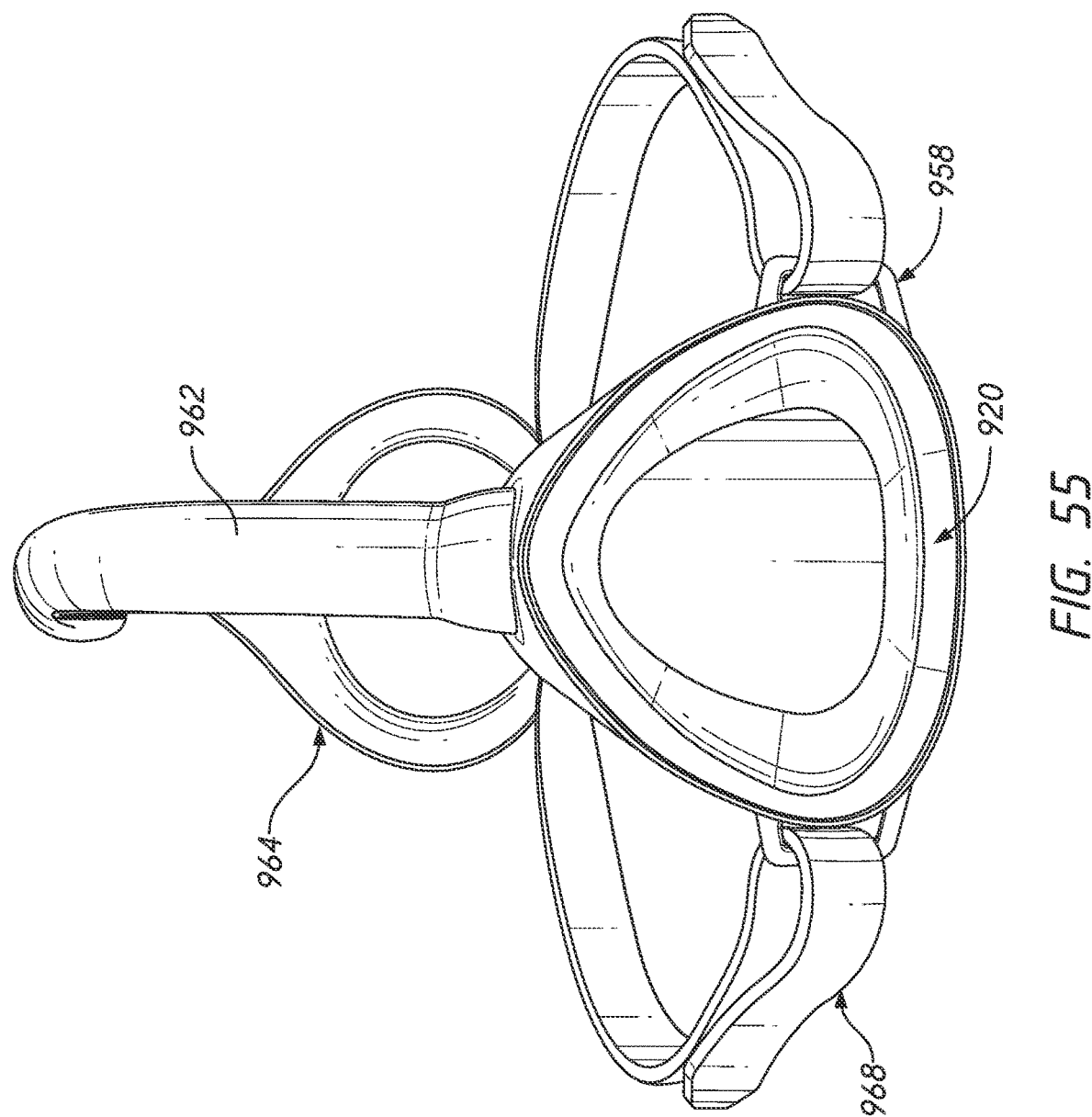
FIG. 55 illustrates a front view of the mask assembly of FIG. 48.
Figure 56:
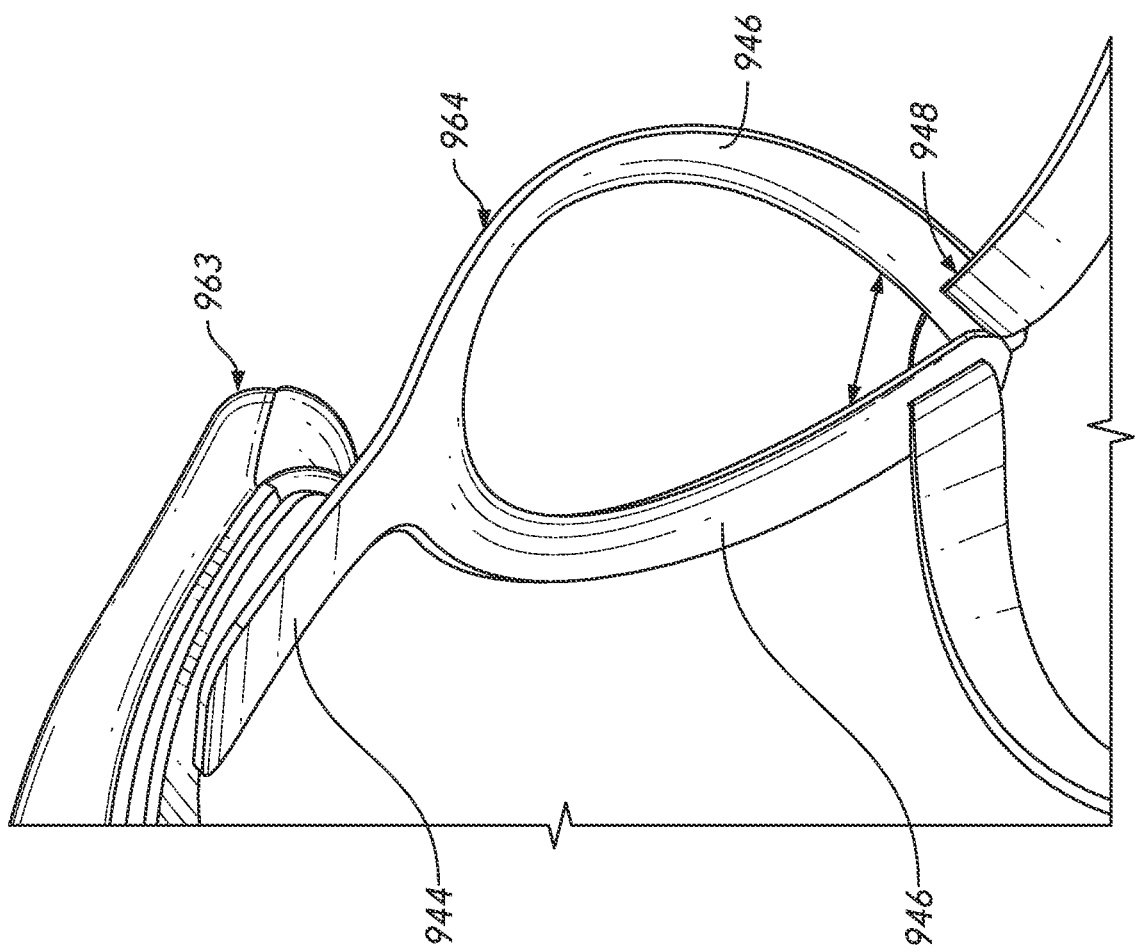
FIG. 56 illustrates a rear strap of a headgear of the mask assembly of FIG. 48.

The rear strap 964 extends between and is coupled to the top strap 962 and the lower strap 968 as shown in FIGS. 48, 55, and 56. The rear strap 964 can be made of a resilient plastic covered in a textile layer. In the illustrated embodiment, the rear strap 964 has a generally inverted Y-shape. The rear strap 964 can be bent or curved to form a cup shape to conform to or accommodate the parietal and/or occipital regions of the back of the user's head in use. The base 944 of the Y-shaped rear strap 964 is coupled to the top strap 962, and the free ends of the two arms 946 of the Y-shaped rear strap 964 are coupled to the lower strap 968. The rear strap 964 can be removably and/or adjustably coupled to the top strap 962, for example, via a hook and loop attachment. The removable attachment to the top strap 962 can allow the rear strap 964 and headgear 960 to be adjusted to accommodate users having various head shapes and/or sizes. In the illustrated embodiment, each of the arms 946 of the rear strap 964 includes an aperture 948 at or near the free end of the arm 946. The apertures 948 receive the lower strap 968. The arms 946 can slide along the lower strap 968 as indicated by the arrows in FIG. 56. The spacing between the free ends of the arms 946 can therefore be adjusted to allow the shape and/or size of the rear strap 964 and headgear 960 to accommodate users having various head shapes and/or sizes.

Figure 58:
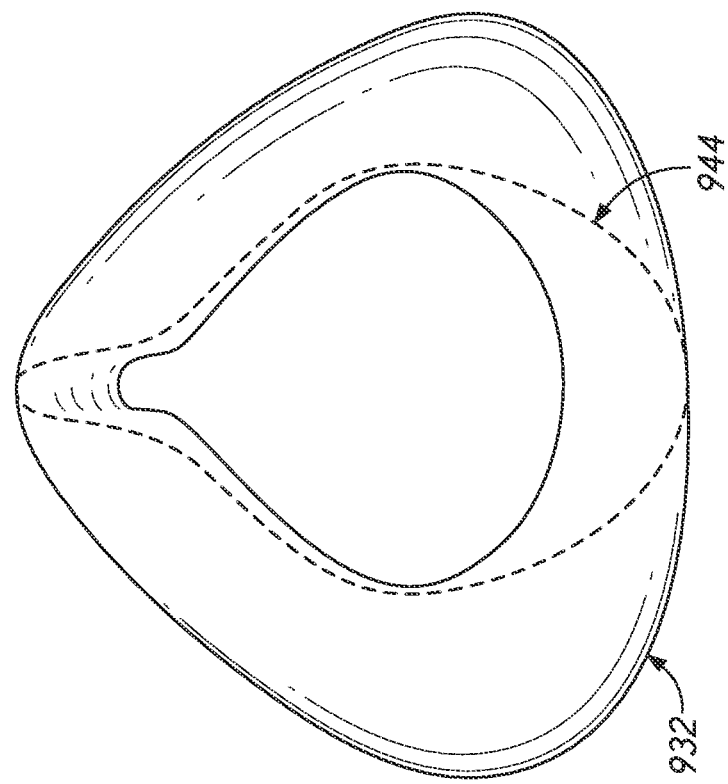
FIG. 58 illustrates a schematic rear view of the seal of FIG. 57.
Figure 57:
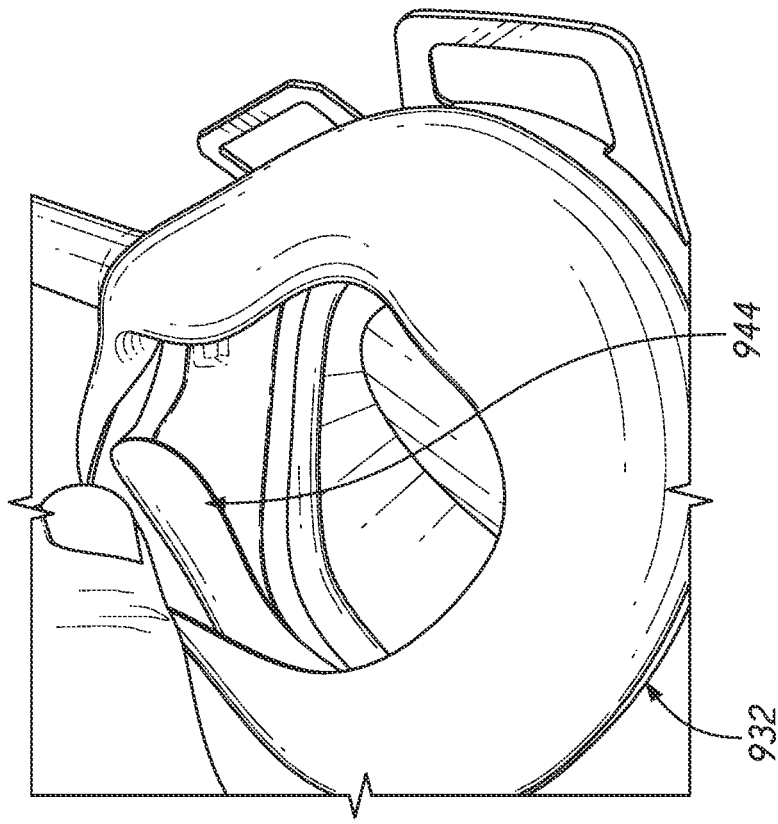
FIG. 57 illustrates a rear perspective view of an example embodiment of a seal.

The seal 930, or other seals described herein or according to the present disclosure, can be a dual-layer seal, as shown in FIGS. 57-58. In the illustrated embodiment, the seal 930 includes an external layer 932 and an internal support layer 944. Either or both of the external layer 932 and support layer 944 can be made of foam, e.g., EVA foam. The internal layer 944 includes reliefs or is absent in the nasal bridge and/or chin region(s). The internal layer 944 therefore adds support and stability in some regions, e.g., in the cheek regions, but allows increased flexibility in the nose and/or chin regions where increased mask conformability is preferred to help the mask seal effectively on users having varying facial geometries. The reliefs in or absence of the internal layer 944 in the nasal bridge and chin regions can help reduce pressure on these regions of the user's face, which can improve patient comfort and/or reduce the occurrence of pressure sores. Improved comfort and/or reduced risk of pressure sores can in turn help increase user compliance with treatment.

In some embodiments, the seal and shell or housing portions of a mask can be temporarily or removably coupled together for use. A removable coupling between the seal and shell can allow the seal to the removed and replaced as needed or desired. For example, FIGS. 66-70 illustrate an example embodiment of a cushion module 1014 including a shell or housing 1020 and a seal 1030. The housing 1020 and/or seal 1030 can be made from foam, e.g., EVA foam. The housing 1020 can be made from a material, e.g., foam that is more rigid and/or has a higher density than the material, e.g., foam of the seal 1030. This provides the housing 1020 with the structure needed to couple to and/or retain a gas supply conduit and/or headgear, while allowing the seal 1030 to be relatively more adaptable and comfortable to the user's face. If the seal is made from a softer and/or less dense foam, the seal may exhibit greater and/or earlier wear and tear than the housing. The seal may also or alternatively exhibit greater and/or earlier wear and tear due to contacting the user's face in use. The seal may therefore need replacement sooner than the housing, and can be removed from the housing and replaced.

The seal 1030 includes a sealing portion 1031 and a retention portion 1033. A rear or proximal wall or surface of the sealing portion 1031 forms a sealing surface 1032 that contacts and seals against the user's face in use. The retention portion 1033 is coupled to and/or extends from a front or distal edge of the sealing portion 1031. The retention portion 1033 removably or detachably couples the seal 1030 to the housing 1020. The retention portion 1033 can retain the housing 1020 in sealing engagement with the seal 1030 to form a breathing chamber. The retention portion 1033 allows the seal 1030 to couple directly to the housing 1020, thereby minimizing components and/or reducing the weight of the cushion module. This can improve user comfort and/or reduce manufacturing time and costs.

In the illustrated embodiment, the retention portion 1033 includes two members, wings, or arms 1034, one extending from each lateral side of the sealing portion 1031. The arms 1034 extend forwardly (i.e., away from the patient) and inwardly from the lateral sides of the sealing portion 1031. When the seal 1030 and housing 1020 are coupled, the sealing portion 1031 is disposed adjacent a proximal edge or perimeter of the housing 1020, and the arms 1034 wrap around an outer front surface 1022 of the housing 1020. As shown, the arms 1034 are undercut or rearwardly or patient-facing concave. The arms 1034 are formed, e.g., thermoformed, to curved inwards and substantially match or correspond to the shape and/or contour of the front surface 1022 of the housing 1020.

In the illustrated embodiment, the retention portion 1033 is formed separately from the sealing portion 1032 and coupled to the sealing portion 1032 at a seam 1040. The seam 1040 can be formed similar to or according to any of the embodiments shown in and described with respect to FIGS. 59-65. Forming the retention portion 1033 and sealing portion 1032 separately allows both the sealing surface 1032 and arms 1034 to be inwardly concave (in other words, concave facing each other when coupled together), which could be more difficult to achieve if formed as one component, for example, using vacuum forming techniques. Alternatively, the seal 1030 can be formed as a single component. The elasticity of the foam material can advantageously allow such a shape, e.g., with undercuts, to be removed from a mold, such as a vacuum mold.

The shape of the retention portion 1033 and/or resilience of the foam, e.g., EVA foam, material can provide or result in internal forces within the retention portion 1033 or forces by the retention portion 1033 on the housing 1020. These forces allow the retention portion 1033 to retain the housing 1020 to form the breathing chamber within the cushion module 1014. In some embodiments, the arms 1034 have a curvature that is smaller or less than a curvature of the front surface 1022 of the housing 1020, which can provide an interference between the arms 1034 and the housing 1020. In some embodiments, internal dimensions of the sealing portion 1031 are slightly smaller than external dimensions of the housing 1020, which can help improve retention forces within or of the arms 1034.

Figure 69:
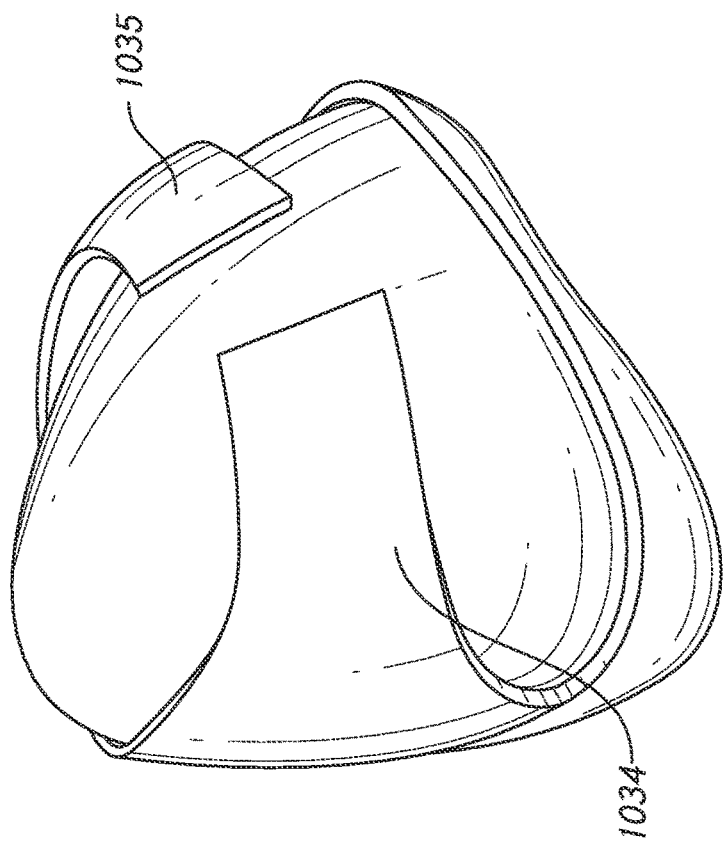
FIG. 69 illustrates a front-bottom-side perspective view of the cushion module of FIG. 66.

In the embodiment of FIGS. 66-70, the arms 1034 extend toward each other and a vertical center line (in the sagittal plane in use) of the cushion module 1014, and curve downward toward a lower portion of the cushion module 1014. In the illustrated embodiment, the arms 1034 taper in depth or height, indicated by direction D in FIG. 66, from the seam 1040 to the free ends 1035, such that the arms 1034 have a greater depth or height near the seam 1040 than at or near the free ends 1035. The downward curvature and/or taper of the arms 1034 forms an opening, which is, e.g., somewhat pear-shaped in the illustrated embodiment as shown in FIG. 69, where the housing 1020 is not covered by the arms 1034. This opening provides a space on or in the housing 1020 for, for example, an inlet aperture and/or bias vent through which gases can enter or exit the cushion module 1014, respectively. The arms 1034 overlap a lower portion of the housing 1020 having a greatest width, or a relatively greater width than an upper portion of the housing 1020. This can help provide resistance against internal pressures in use (e.g., caused by the pressurized gas supply), which may be greater at or near the widest portion of the cushion module 1014.

Figure 67:
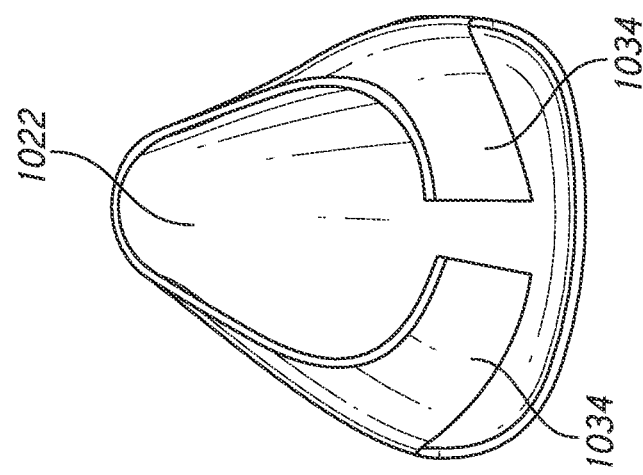
FIG. 67 illustrates a front-bottom perspective view of the cushion module of FIG. 66.
Figure 66:
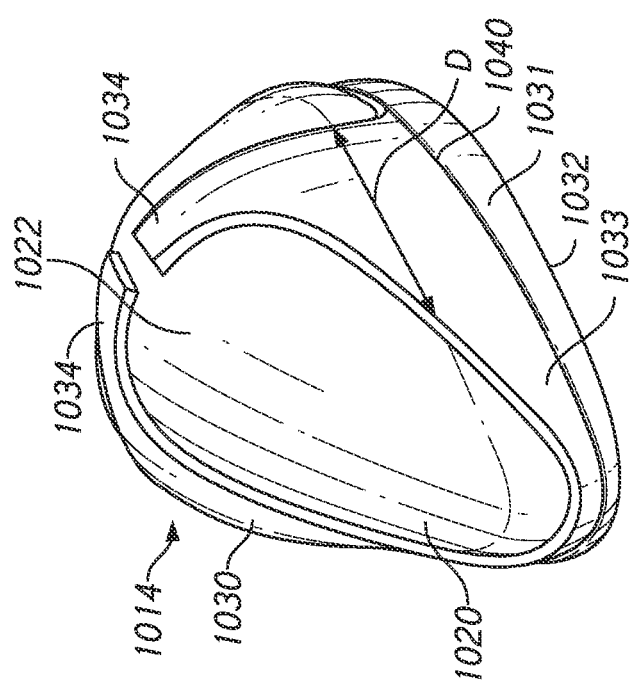
FIG. 66 illustrates a front-side perspective view of an example embodiment of a cushion module including a seal and housing removably coupled to each other.
Figure 70:
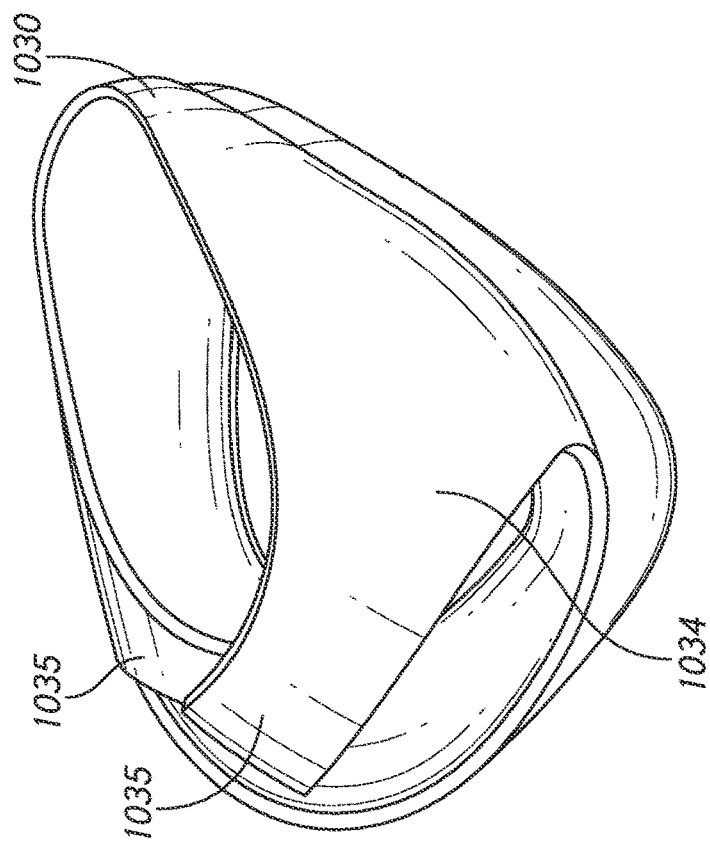
FIG. 70 illustrates a front-bottom-side perspective view of the seal of the cushion module of FIG. 66.

The arms 1034 are biased inwards such that before being coupled to the housing 1020, free ends 1035 of the arms 1034 overlap or cross over each other, as shown in FIG. 70. This bias helps increase the retention forces applied by the arms 1034 to the housing 1020 when the seal 1030 and housing 1020 are coupled. The arms 1034 can be flexed outwardly to allow the seal 1030 to be coupled to the housing 1020. When the seal 1030 is coupled to the housing 1020 and the arms are engaging the outer surface of the housing, the arms 1034 do not meet or overlap each other, as shown in FIGS. 66, 67, and 69.

Figure 72:
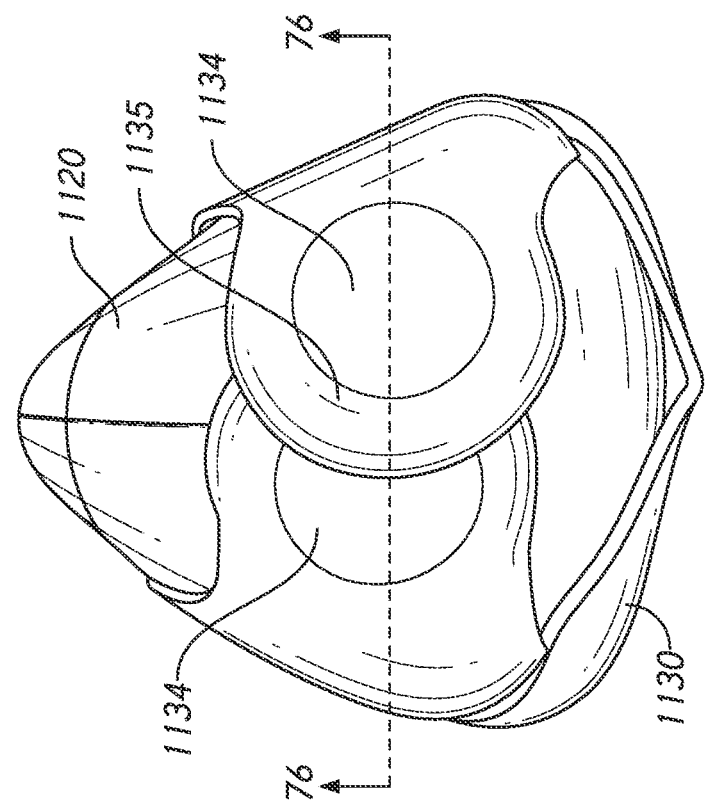
FIG. 72 illustrates a front view of the cushion module of FIG. 71.
Figure 71:
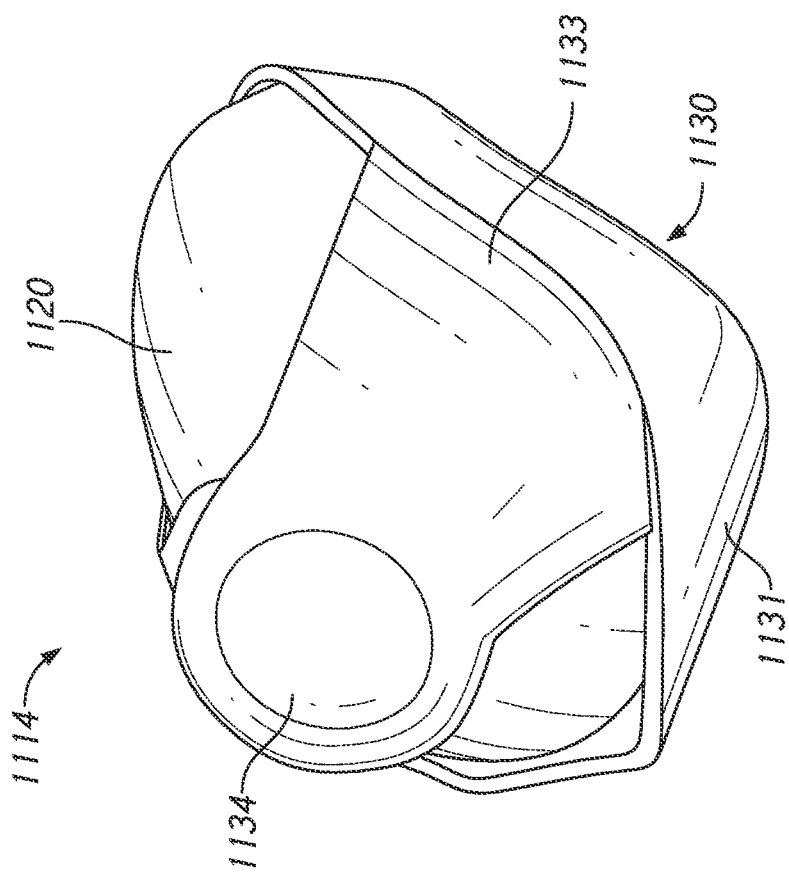
FIG. 71 illustrates a front-side-bottom perspective view of an example embodiment of a cushion module including a seal and housing removably coupled to each other.

FIGS. 71-76 illustrate another example embodiment of a cushion module 1114 including a shell or housing 1120 and a seal 1130 that are temporarily or removably coupled together for use. The cushion module 1114 can be similar to cushion module 1014 and include a sealing portion 1131 and a retention portion 1133 including two arms 1134 that extend over a lower portion of the housing 1120. The arms 1134 can have rounded free ends 1135 as shown. In this embodiment, the free ends 1135 overlap each other when the seal 1130 and housing 1120 are assembled for use, as shown in FIG. 72. The arms 1134 are inwardly (with respect to the cushion module 1114) concave and have a curvature that matches or corresponds to the front surface 1122 of the housing 1120.

The curvature of the free ends 1135 can help retain the arms 1134 in an overlapped arrangement when coupled to the housing 1120.

The housing 1120 can include a support wall 1124 extending and curving inwardly from a perimeter (or rear or patient-proximal edge) of the housing 1120, as shown in FIGS. 74-76. When the housing 1120 and seal 1130 are assembled, the support wall 1124 underlies and supports the sealing surface 1132. The support wall 1124 can help inhibit or reduce the likelihood of the sealing surface 1132 collapsing in use, thereby improving the seal between the seal 1130 and the user's face. The support wall 1124 can extend around an entirety or a portion of the perimeter of the housing 1120. If the support wall 1124 does not extend around the entirety of the perimeter, portions of the sealing surface 1132 can be unsupported, which can provide improved sealing and comfort for the user due to an increased range of allowable travel or deformation.

Figure 78:
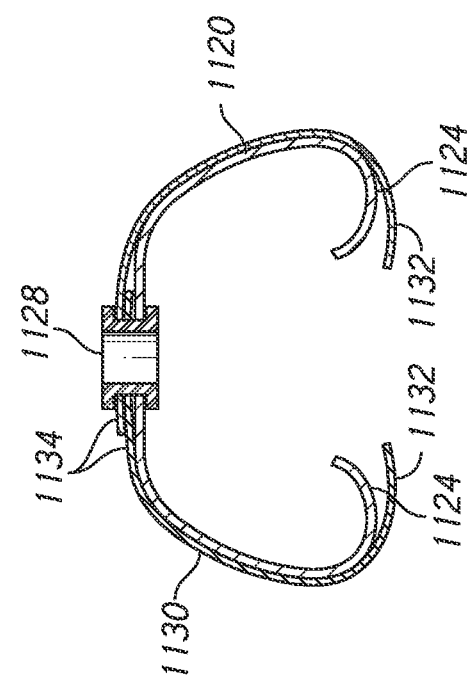
FIG. 78 illustrates a schematic cross-section of the cushion module of FIG. 77.
Figure 77:
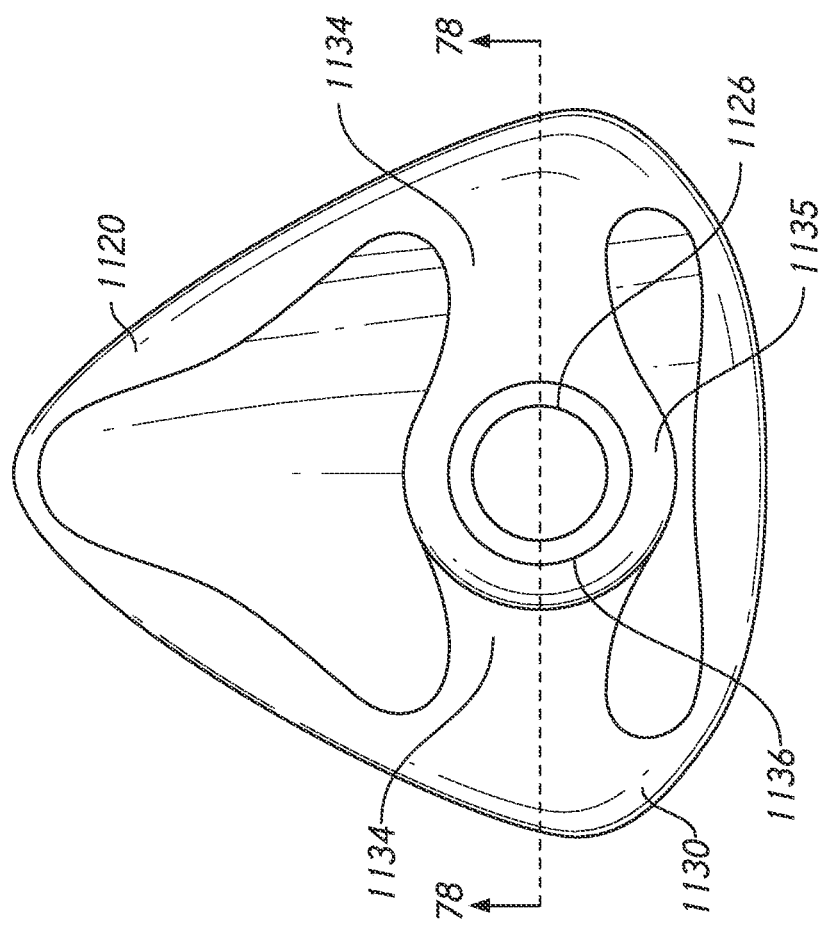
FIG. 77 illustrates a schematic front view of an example embodiment of a cushion module including a seal and housing removably coupled to each other.
Figure 79:
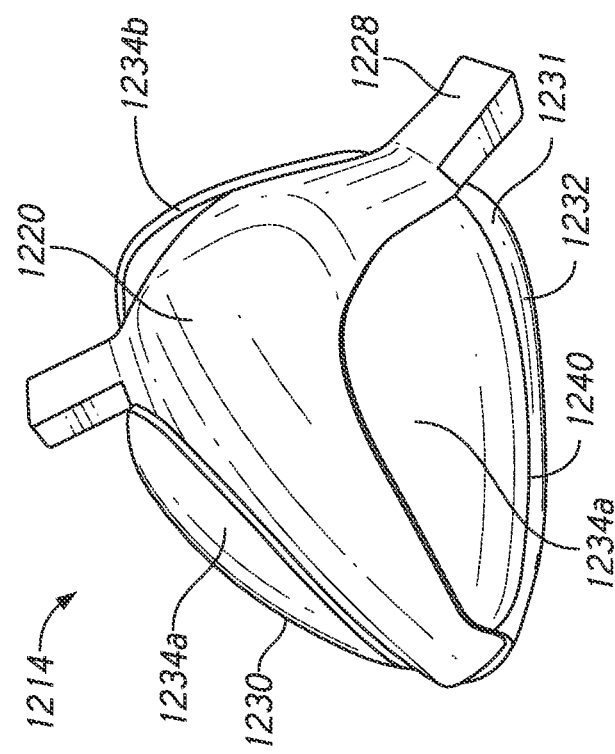
FIG. 79 illustrates a front-side perspective view of an example embodiment of a cushion module including a seal and housing removably coupled to each other.
Figure 80:
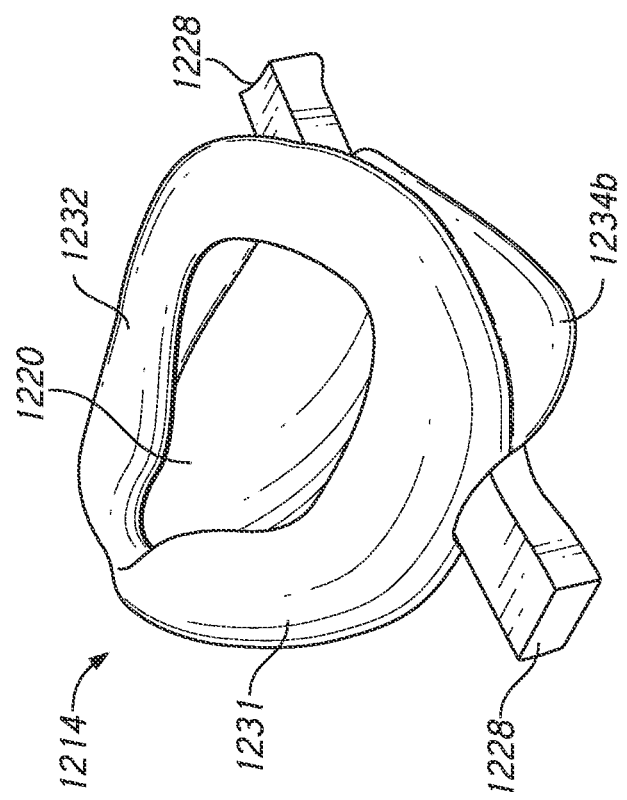
FIG. 80 illustrates a rear-bottom-side perspective view of the cushion module of FIG. 79.
Figure 82:
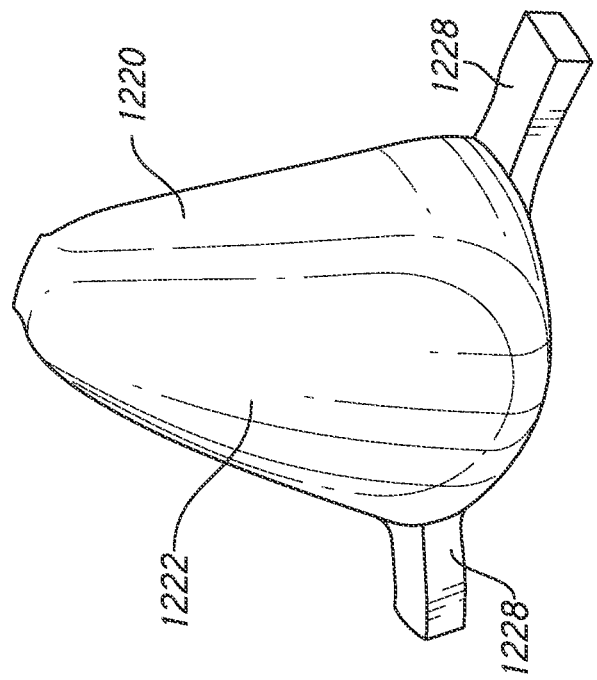
FIG. 82 illustrates a front view of the housing of the cushion module of FIG. 79.

In some embodiments, for example as shown in FIGS. 77-78, each of the free ends 1135 of the arms 1134 includes an aperture 1136. The housing 1120 includes a corresponding aperture 1126 that can serve as in inlet into the breathing chamber of the cushion module 1114. When the seal 1130 is coupled to the housing 1120, the apertures 1136 of the arms 1134 overlie and align with the aperture 1126 of the housing 1120. A swivel, elbow, supply conduit, bushing 1128 (to which a swivel, elbow, or supply conduit can be coupled) or the like can be coupled to the housing 1120 at or via the aperture 1126 to deliver a supply of pressurized breathing gases to the breathing chamber. The swivel, elbow, supply conduit, bushing 1128 or the like can be coupled to the housing aperture 1126 through the apertures 1136 of the arms 1134 and can help secure the seal 1130 to the housing 1120 by retaining the free ends 1135 of the arms 1134 in position relative to the housing 1120, as shown in FIG. 78. The swivel, elbow, supply conduit, bushing 1128 or the like can be sized such that the apertures 1136 of the arms 1134 are stretched to pass over a lip or edge of the swivel, elbow, supply conduit, bushing 1128 or the like, which can help secure the arms 1134 to the swivel, elbow, supply conduit, bushing 1128 or the like. In the illustrated embodiment, the bushing 1128 has a cylindrical or tubular body and a lip or flange extending or protruding radially outwardly from the cylindrical body at or near each axial or longitudinal end of the bushing 1128. When the housing 1120 and seal 1130 are assembled as described, portions of the arms 1134 are sandwiched or clamped about the cylindrical body of the bushing 1128 between the two lips or flanges.

FIGS. 79-82 illustrate another example embodiment of a cushion module 1214 including a shell or housing 1220 and a seal 1230 that are temporarily or removably coupled together for use. The seal 1230 includes a sealing portion 1231 having a sealing surface 1232 and a retention portion 1233. The retention portion 1233 can be coupled to the sealing portion 1231 at a seam 1240. In this embodiment, the retention portion 1233 includes two opposing side arms 1234a extending from upper lateral sides of the sealing portion 1231 and a lower arm 1234b extending from a lower edge of the sealing portion 1231. Each of the arms 1234a, 1234b can be generally triangular shaped as shown. The arms 1234a, 1234b are inwardly concave and extend over the front surface 1222 of the housing 1220 when the seal 1230 is coupled to the housing 1220.

The housing 1220 can include two opposing headgear connectors 1228 extending laterally outwardly from the perimeter of the housing 1220. In the illustrated embodiment, each of the headgear connectors 1228 extends between one of the side arms 1234a and the lower arm 1234b when the seal 1230 is coupled to the housing 1220. Headgear straps can be coupled to the headgear connectors 1228 such that the headgear connectors 1228 allow headgear straps to be coupled to the cushion module 1214. The headgear connectors 1228 can include buckle(s), hook-and-loop connection(s), clip(s) and/or other connection means to couple to the headgear straps. In some embodiments, the headgear connectors 1228 can be elongated and themselves form the headgear straps or portions thereof.

Figure 81:
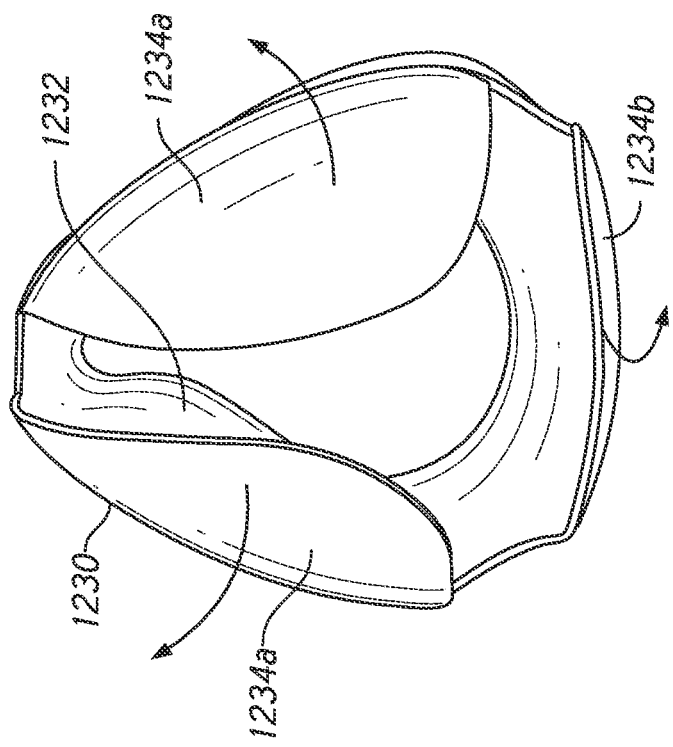
FIG. 81 illustrates a rear view of the seal of the cushion module of FIG. 79.

To couple the seal 1230 to the housing 1220, the arms 1234a, 1234b can be pulled or flipped outwardly away from a center of the seal 1230, as shown by the arrows in FIG. 81. The housing 1220 can then be inserted past the arms 1234a, 1234b into the seal 1230. The arms 1234a, 1234b can then be pushed, flipped, or allowed to return back into place to retain the housing 1220 to the seal 1230. The formed, e.g., thermoformed shape and curved contour of the arms 1234a, 1234b provides the arms 1234a, 1234b with an internal resilience and biases the arms 1234a, 1234b to return to their inwardly curved, formed shape when deformed. This resilience provides a retention force to retain the housing 1220 and seal 1230 in engagement with each other. The foam material of the seal 1230 can provide sufficient flexibility to allow the arms 1234a, 1234b to temporarily retain an open configuration, for example, to allow for coupling and/or decoupling of the housing 1220 with the seal 1230.

Figure 88:
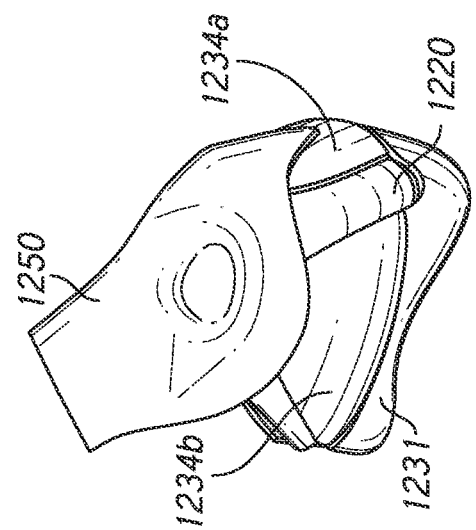
FIG. 88 illustrates a bottom-side perspective view of the cushion module of FIG. 83 with the retention cover in a partial lifted configuration.
Figure 90:
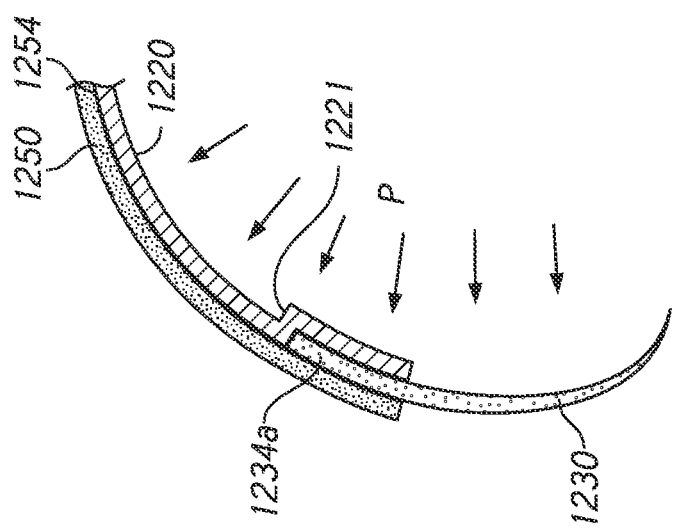
FIG. 90 illustrates a schematic partial cross-section of a variation of the cushion module of FIG. 83.
Figure 89:
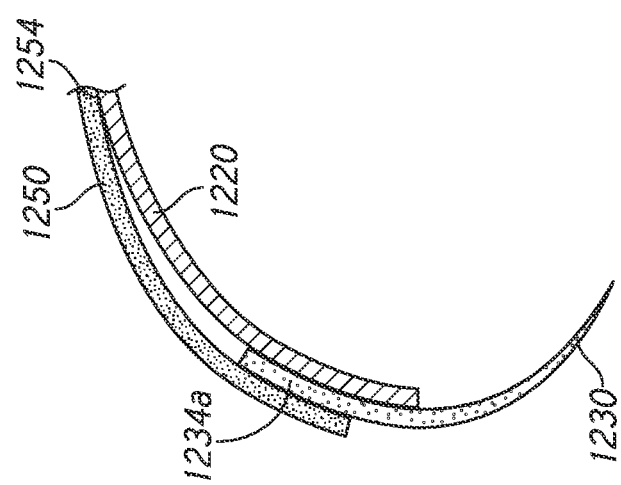
FIG. 89 illustrates a schematic partial cross-section of the cushion module of FIG. 83.
Figure 93:
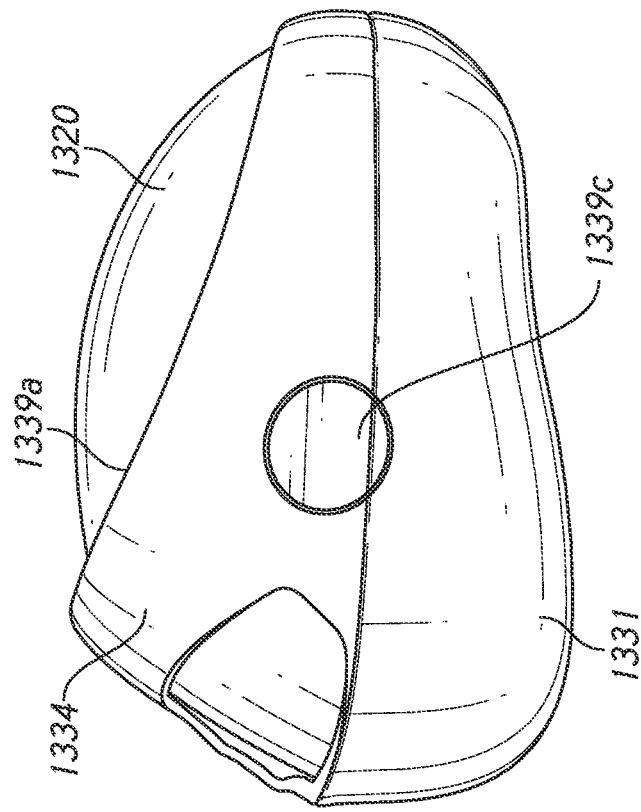
FIG. 93 illustrates a side view of the cushion module of FIG. 92.
Figure 92:
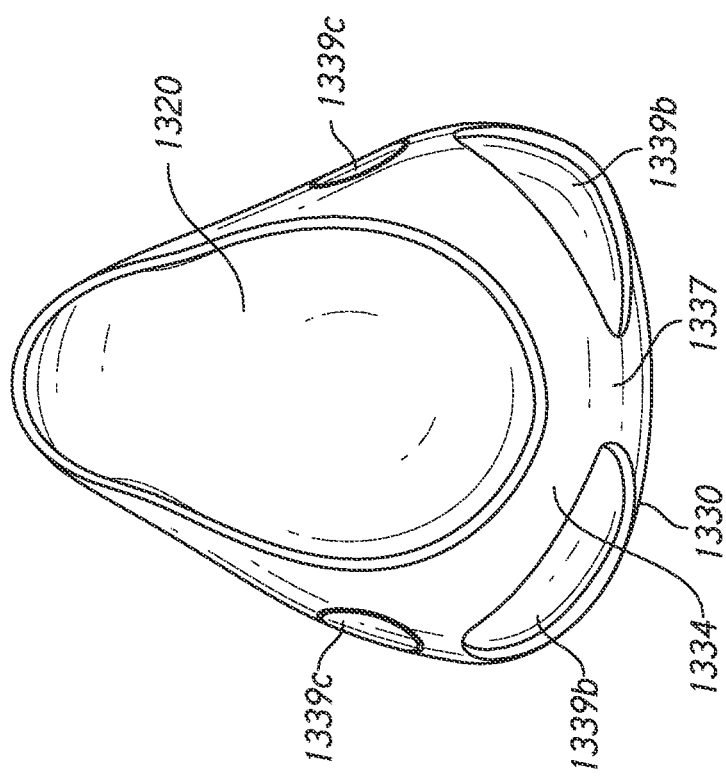
FIG. 92 illustrates a front view of an example embodiment of a cushion module including a seal and housing removably coupled to each other.

In some embodiments, a cushion module such as cushion module 1214 shown in FIGS. 79-82 includes a retention component or cover 1250, as shown in FIGS. 83-91. The cover 1250 can increase the retention force between the seal 1230 and the housing 1220, which can help achieve an adequate seal and/or reduce leaks between the housing 1220 and the seal 1230. In use the cover 1250 is positioned over portions of the front surface 1222 of the housing 1220 and the arms 1234a, 1234b such that portions of the arms 1234a, 1234b are sandwiched between the housing 1220 and the cover 1250, as shown in FIG. 89. In some embodiments, the housing 1220 can include an inward step 1221 proximate the perimeter or patient-proximal edge of the housing 1220, as shown in FIG. 90. The free ends of the side arms 1234a and/or lower arm 1234b can abut and/or be positioned adjacent or near the step 1221 when the seal 1230 is assembled with the housing 1220. The step 1221 can help align the arms 1234a, 1234b with the housing 1220 and/or can help strengthen the engagement between the housing 1220 and the seal 1230. Arrows P in FIG. 90 indicate the outward force on the housing 1220 and seal 1230 applied by the internal pressure within the breathing chamber of the cushion module 1214 during use. This outward force can help increase the engagement forces between the housing 1220 and seal 1230. The curvature of the arms 1234a, 1234b and/or the cover 1250 apply an inward force that resists forces from the internal pressure. This can help reduce leaks between the housing 1220 and seal 1230 and/or can help reduce the likelihood of the housing 1220 and seal 1230 becoming disengaged during use.

Figure 91:
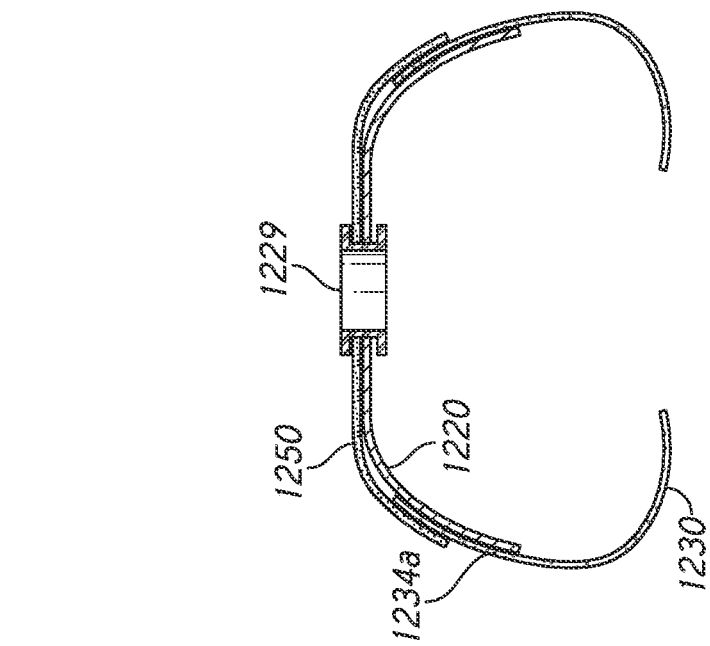
FIG. 91 illustrates a schematic cross-section of a variation of the cushion module of FIG. 83.

The cover 1250 can have an inwardly concave curvature that matches or corresponds to the curvature of the front surface 1222 of the housing 1220. The cover 1250 can be coupled, permanently or removably or temporarily, to the outer surface of the housing 1220 at one or more connection points or joints 1254 (shown in FIGS. 89-90), for example, at or near a center point of the cover 1250 and/or housing 1220. For example, the cover 1250 can be permanently attached to the housing 1220 via adhesive(s), stitching, or welding. The cover 1250 can be removably attached to the housing 1220 via a snap fit, a hole and button arrangement, or other mechanisms. In some embodiments, for example as shown in FIG. 91, the housing 1220 and cover 1250 are coupled together by a bushing 1229 that extends through aligned apertures in the housing 1220 and cover 1250. The bushing 1229 can couple to an air supply conduit or an elbow or swivel, which can in turn couple to an air supply conduit. The bushing 1229 can be similar to bushing 1128 shown in and described with respect to FIGS. 77-78.

In the illustrated embodiment, an upper portion of the cover 1250 has a generally trapezoidal shape, and a lower portion of the cover 1250 has a rounded lower edge. Other appropriate shapes are also possible. In the illustrated embodiment, upper corner or lateral end portions of the cover 1250 overlap the side arms 1234a. The upper corner or lateral end portions of the cover 1250 can form or include upper connection points 1252 for upper straps of a headgear. The cover 1250 can also or alternatively include lower connection points for lower straps of a headgear. In some embodiments, the cover 1250 can extend beyond the outer perimeter of the cushion module 1214 to form the headgear straps or portions thereof.

Figure 87:
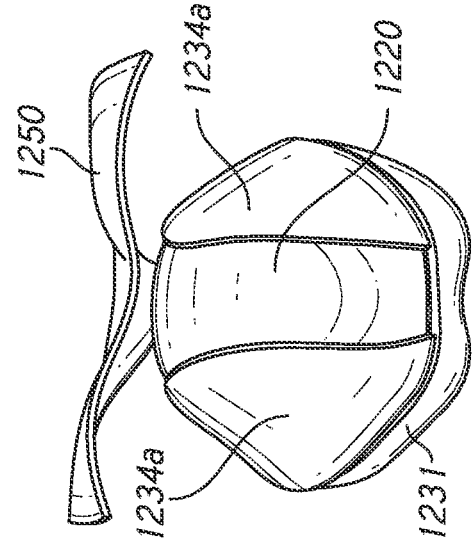
FIG. 87 illustrates a top view of the cushion module of FIG. 83 with the retention cover in a lifted configuration.
Figure 86:
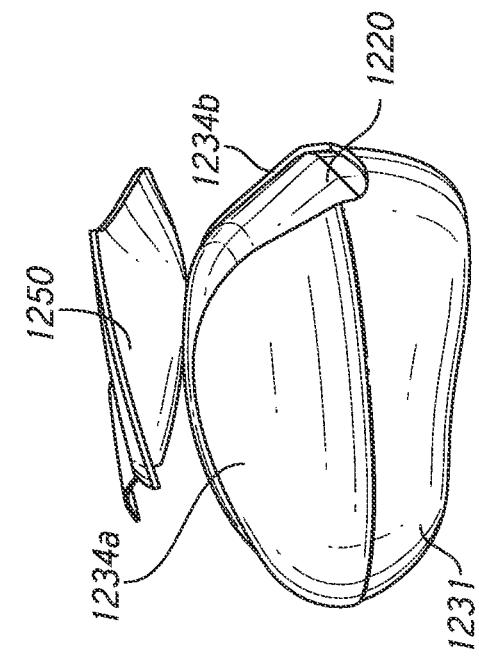
FIG. 86 illustrates a side view of the cushion module of FIG. 83 with the retention cover in a lifted configuration.

To allow for assembly of the housing 1220 and seal 1230, the cover 1250 can be deformed as shown in FIGS. 86-88. In the illustrated embodiment, a center of the cover 1250 is fixed to the housing 1220. Side portions of the cover 1250 can be lifted or flipped away from the housing 1220 and/or inside out to allow for assembly, as shown in FIGS. 86-88. In the illustrated embodiment, the cover 1250 can retain a gull-wing deformed shape during assembly. This allows the arms 1234a, 1234b to be deformed for assembly with the housing 1220 and then moved into contact or engagement with the housing 1220.

FIGS. 92-97 illustrate another example embodiment of a cushion module 1314 including a shell or housing 1320 and a seal 1330 that are temporarily or removably coupled together for use. The housing 1320 can include a support wall 1324, similar to the embodiment shown in and described with respect to FIGS. 71-78. The seal 1330 includes a sealing portion 1331 having a sealing surface 1332 that defines an aperture 1335 that receives the user's nose and/or mouth in use and a retention portion 1333 coupled to and/or extending from the sealing portion 1331. The retention portion 1333 includes a retention belt, strap, or sling 1334 that extends from one lateral side of the sealing portion 1331 to the other and helps hold the seal 1330 and housing 1320 in engagement. A tether 1337 extends between and connects a lower portion of the sealing portion 1331 and a lower edge of the retention belt 1334.

In the illustrated embodiment, the retention belt 1334 extends across a lower portion of the housing 1320. The retention belt 1334 being continuous across the width of the housing 1320 can help provide an increased retention force between the housing 1320 and the seal 1330 as the retention belt 1334 cannot flex away from the housing 1320, for example, as two separate arms might be able to, when the cushion module 1314 is under pressure and/or when a force is applied to the housing 1320. The tether 1337 can help inhibit or reduce the likelihood of the retention belt 1334 sliding up on the housing 1320.

In the illustrated embodiment, the retention belt 1334 has a curvature similar to the arms 1034 of FIGS. 66-70 and curves downward and forward from each lateral side. An upper edge of the retention belt 1334 and upper portion of the retention portion 1333 define an upper opening 1339a where the housing 1320 is not covered by the seal 1330. In the illustrated embodiment, the upper opening 1339a is somewhat pear-shaped, similar to the opening of the embodiment of FIG. 69. This opening 1339a can provide a space on or in the housing 1320 for, for example, an inlet aperture and/or bias vent through which gases can enter or exit the cushion module 1314, respectively. The tether 1337, a lower edge of the retention belt 1334, and a lower portion of the retention portion 1333 or the sealing portion 1331 define two lower openings 1339b. Any of all of the openings 1339a, 1339b can reduce the material of the seal 1330 and therefore weight of the cushion module 1314, provide aesthetic appeal, and/or allow for increased elasticity of the retention belt 1334 and tether 1337 to allow the housing 1320 to be inserted into the upper opening 1339a during assembly. Alternatively, the cushion module 1314 can be assembled by inserting the housing 1320 into the aperture 1335 of the seal 1330 and stretching the aperture 1335 to fit over the housing 1320, as shown in FIGS. 94-97. The seal 1330 can include an aperture in each lateral side at or near the location of circle 1339c. These apertures 1339c can provide aesthetic appeal and/or align with corresponding apertures in the housing 1320 to provide inlet apertures for a supply of pressurized gas to be delivered to the breathing chamber of the cushion module 1314.

Figure 47:
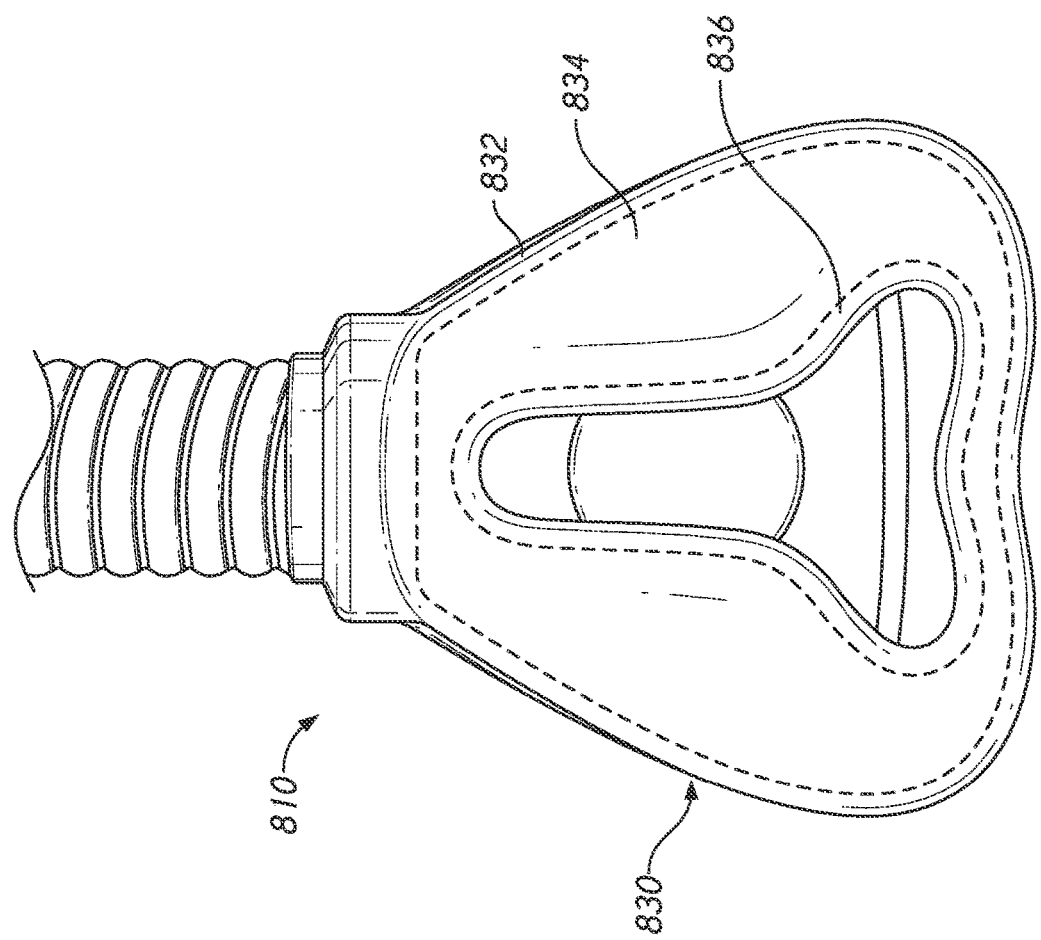
FIG. 47 illustrates a rear view of an example embodiment of a mask having a seal with varying thickness regions.

FIG. 47 illustrates an example embodiment of a mask 810 including a seal 830 having regions of varying thickness. A transition region 834, indicated by the area inside the dashed lines in FIG. 47, can contact the patient's face in use. A portion of the seal 830 outside of or distal to the transition region 834 can be a thick region 832. The increased thickness can advantageously provide greater structure and/or support to the seal 830. The thick region 832 can be adjacent to and/or coupled to the shell portion of the mask 810. A portion of the seal 830 inside of or proximal to the transition region 834 can be a thin region 836. The thin region 836 can advantageously provide adaptability to help the seal 830 better conform to and seal against the patient's face in use. The thickness of the seal 830 can increase in the transition region 834 from the thick region 832 to the thin region 836. The thick region 832 can have a thickness in the range of about 2 mm to about 5 mm. The transition region 834 can have a thickness in the range of about 1 mm to about 3 mm. The thin region 836 can have a thickness in the range of about 0.3 mm to about 2 mm, for example, about 0.5 mm to about 1 mm. Any of the seals described herein or according to the present disclosure can include such regions of varying thickness.

As described herein, masks according to the present disclosure can be manufactured via thermoforming. In some embodiments, a flat sheet of EVA foam is heated to a temperature that allows plastic deformation. The sheet of EVA is then formed to a shape over a mold using vacuum forming. The formed EVA is then trimmed to the desired shape once cooled. Thermoforming can advantageously allow for a range of options in textile coverings, colors, and/or foam densities. The flexibility of the mask can be affected or determined based on the properties of the foam and/or textile covering selected. The costs of tools and/or machines used for thermoforming can advantageously be relatively low compared to, for example, injection molding and similar processes. Thermoforming can allow for open-shut tooling and/or multi-cavity tools, which can reduce manufacturing costs. Thermoforming can allow for the construction of multiple layer components.

Figure 38:
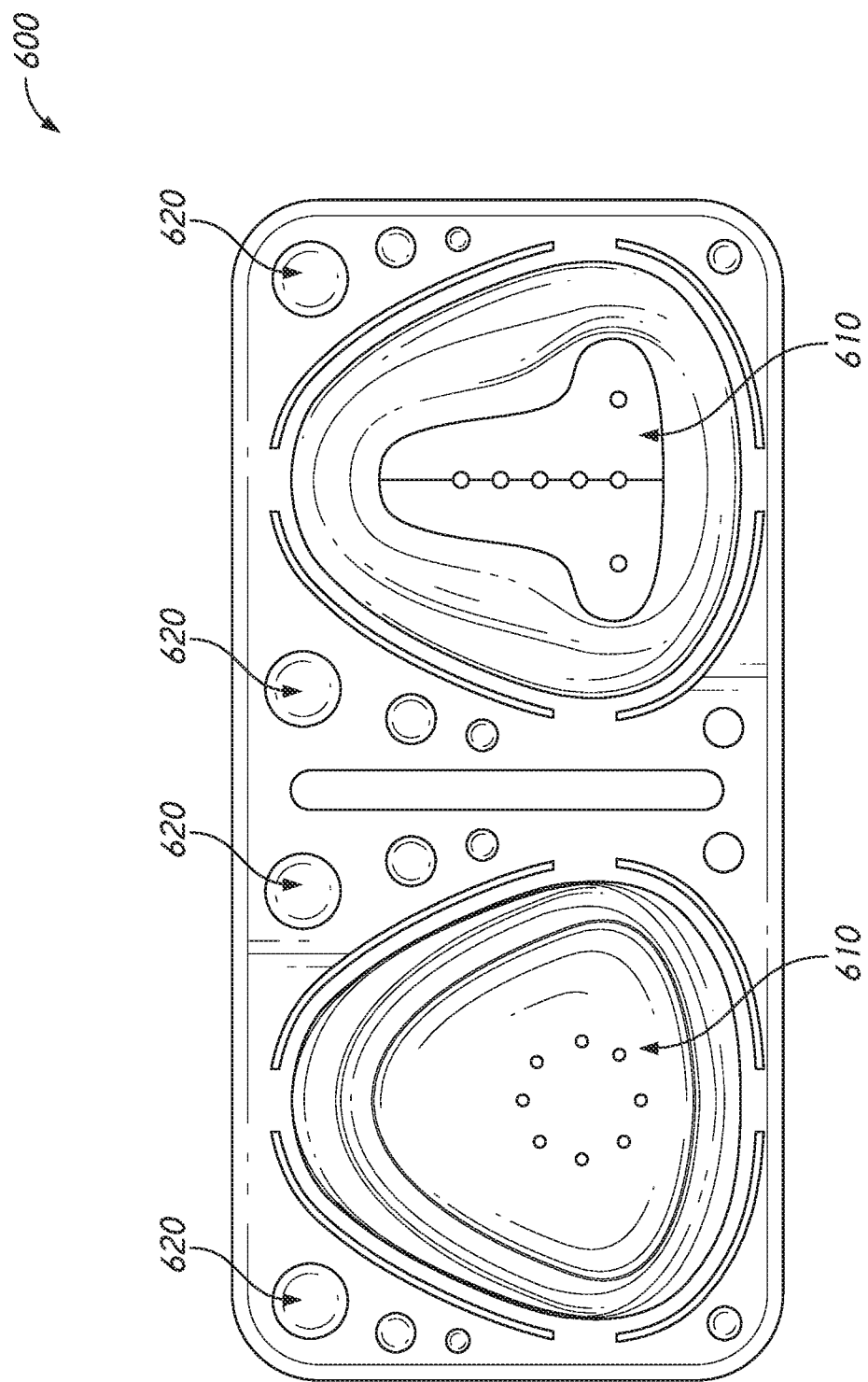
FIG. 38 illustrates an example embodiment of a mold for forming components of a mask.

FIG. 38 illustrates an example embodiment of a female mold 600 that can be used to vacuum thermoform EVA foam sheets into the desired shapes for the seal and shell or housing components of some of the masks described herein.

The illustrated embodiment can be used to form the mask 210 of FIGS. 2-11. In some embodiments, the mold is created via 3D printing. In some embodiments, the mold is made in traditional ways from, for example, plastic or metal. As shown, the mold 600 can include air holes 610 that allow the vacuum forming process to occur properly. The air holes 610 can allow air to be evacuated from between the tool and the foam sheet(s), which can allow better conformance between the foam and the tool. The mold 600 can include guides 620 to help correctly position the mold 600 in the thermoforming machine. In the illustrated embodiment, the guides 620 have a semi-spherical shape.

Figure 39:
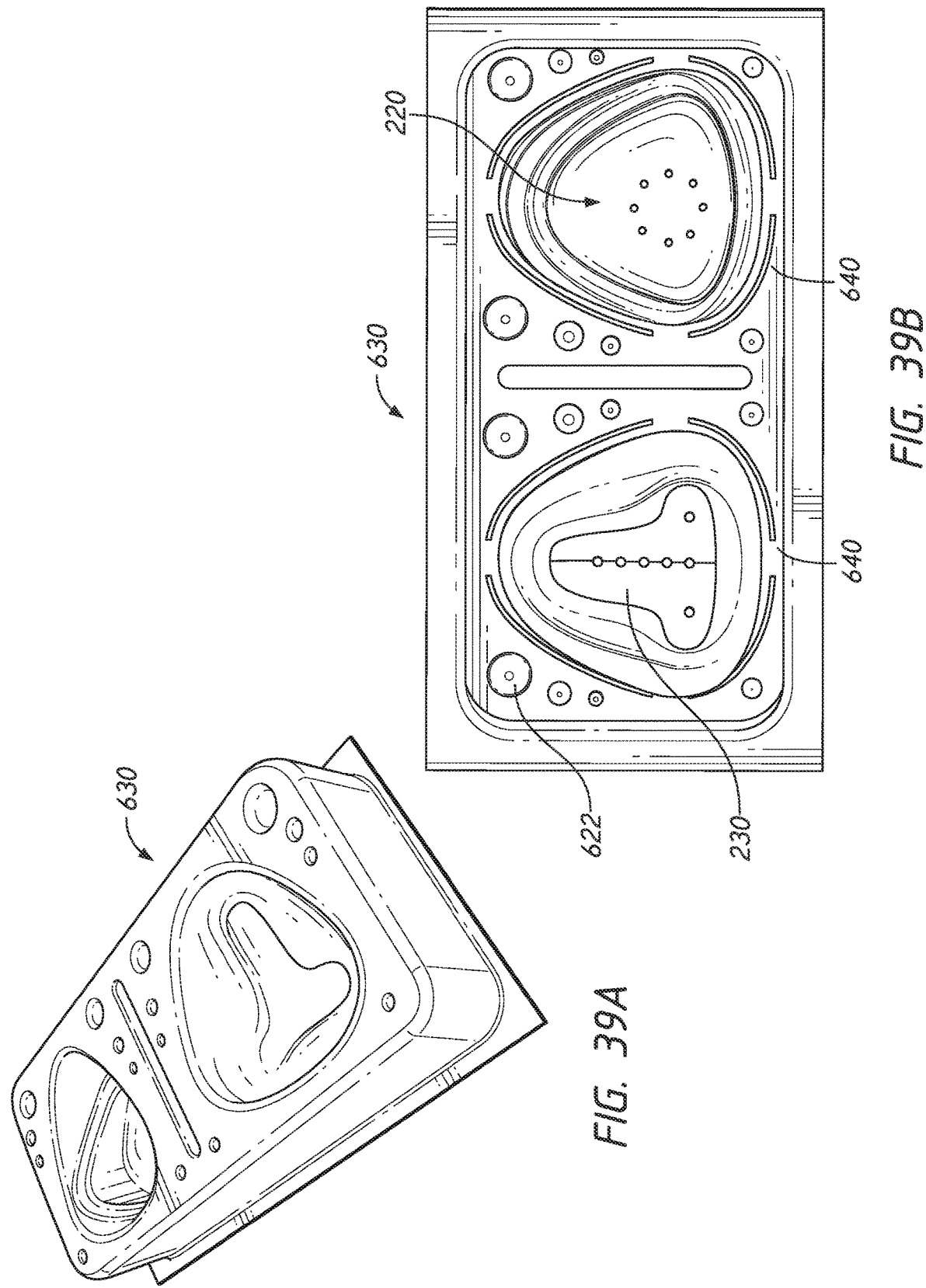
FIG. 39A illustrates a first side of an EVA foam sheet after vacuum thermoforming using the mold of FIG. 38.
FIG. 39B illustrates an opposite, second side of the EVA foam sheet of FIG. 39A.
Figure 40:
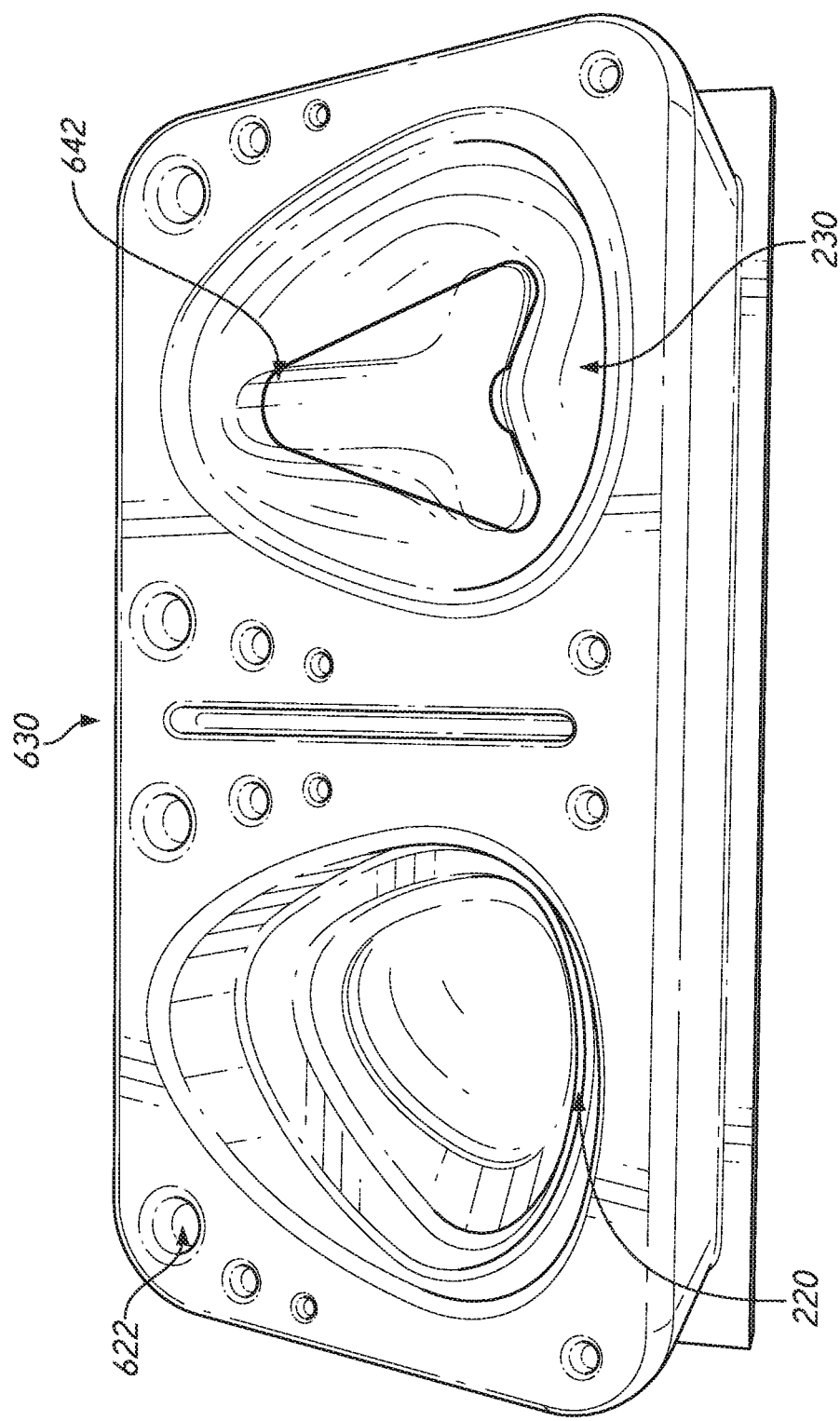
FIG. 40 illustrates the first side of the EVA foam sheet of FIG. 39A showing a cut line for creation of a nasal aperture.

FIGS. 39A-40 illustrate the EVA foam sheet 630 after thermoforming using the mold 600 of FIG. 38. As shown, the sheet 630 includes the housing 220 and seal 230 prior to trimming. The mold 600 advantageously allows both the housing 220 and seal 230 to be formed from a single sheet 630 in a single thermoforming step. The sheet 630 can include indents 622 from the guides 620 in the mold 600. After thermoforming, the housing 220 and seal 230 can be cut out of the sheet 630 along a cut line 640. As shown, the cut line 640 is positioned such that the housing 220 and seal 230 include lips 229, 239 when cut from the sheet 630. Immediately after thermoforming, the seal 230 does not include the nasal aperture 234. The nasal aperture 234 can be created after thermoforming by cutting along a cut line 642, shown in FIG. 40. After trimming, the housing 220 and seal 230 components can be joined together as described herein. When vacuum forming and/or thermoforming foam sheets, it can be difficult to form undercut geometries in some cases, so it could be difficult to form the housing and seal as a single integrated component. Instead, the housing and seal can be formed separately as described and then joined together. The housing and seal can be joined together permanently or temporarily, and directly to each other or via a joining member, as shown and described in various embodiments herein.

Figure 41B:
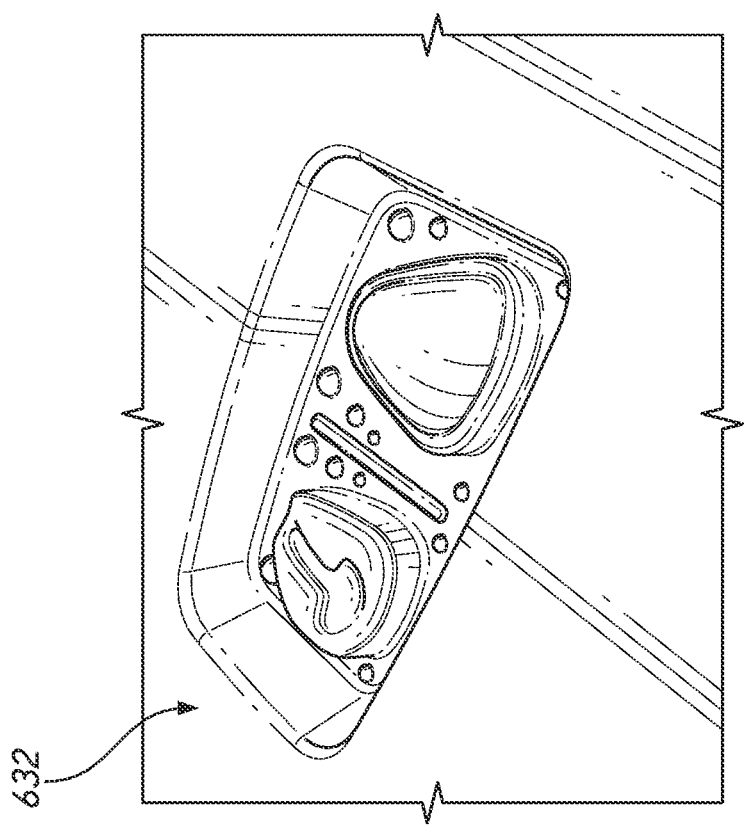
FIGS. 41A and 41B illustrate example embodiments of EVA foam sheets including textile coverings having desirable properties after vacuum thermoforming using the mold of FIG. 38.
Figure 41A:
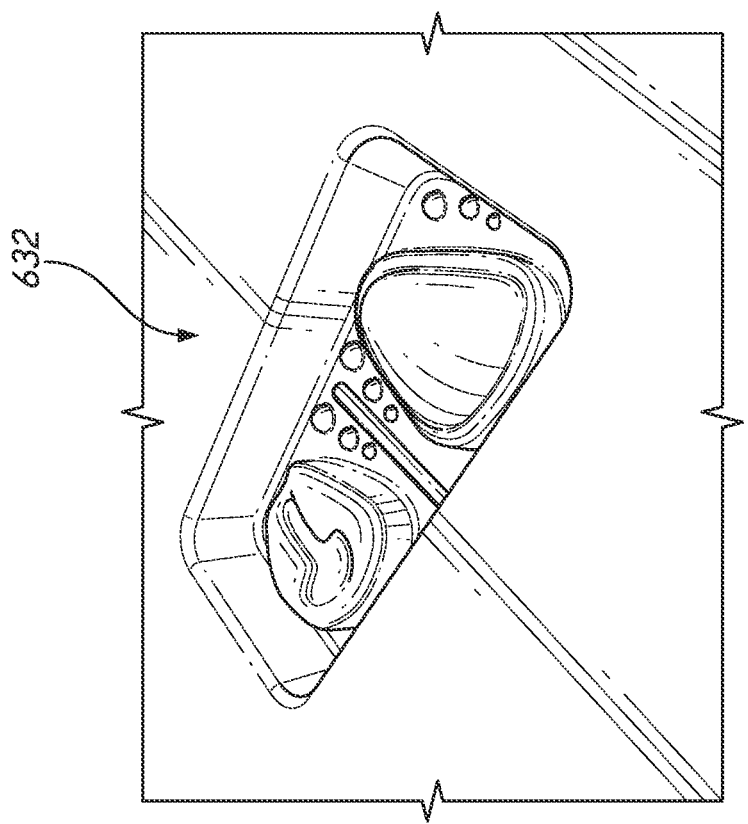

In embodiments in which one or more EVA foam components are covered with a textile covering, the textile covering can be adhered, laminated, or otherwise applied to the EVA foam prior to vacuum thermoforming. In some embodiments, the textile covering can be adhered, laminated, or otherwise applied to the EVA foam after thermoforming. FIGS. 41A-41B illustrate example embodiments of thermoformed EVA sheets 632 covered in a textile covering prior to trimming. In the illustrated embodiment, the textile covering was applied to the sheets 632 prior to thermoforming, for example, with an adhesive or flame lamination, then once the adhesive was cured, the sheets 632 were thermoformed. The EVA foam and textile covering stretch as the sheet 632 is vacuum formed over the mold. When the foam and textile covering cool, they retain the formed shape. The textile covering can advantageously provide the mask with improved aesthetics, comfort, and/or wear resistance.

Figure 41D:
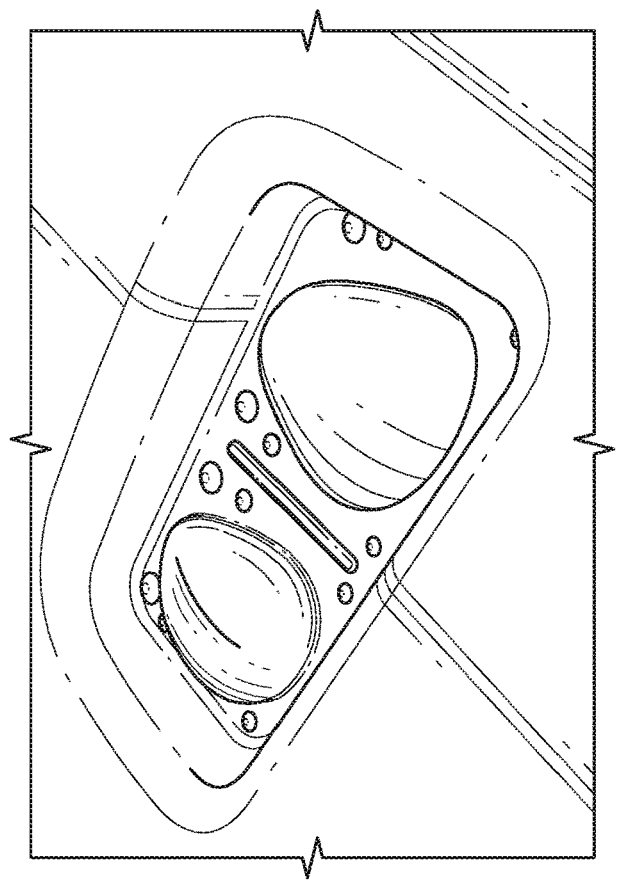
FIGS. 41C and 41D illustrate example embodiments of EVA foam sheets including textile coverings that do not stretch in all directions after vacuum thermoforming using the mold of FIG. 38.
Figure 41C:
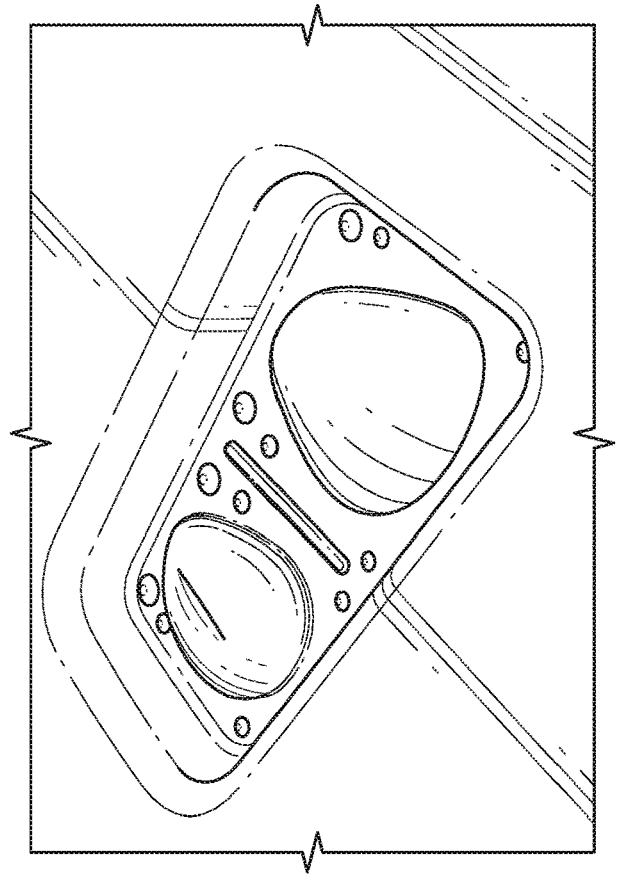

In embodiments in which the textile covering is applied to the EVA foam prior to thermoforming, selecting a material having the ability to stretch in all directions for the textile covering can allow the seal to completely form. In some cases, materials having the ability to stretch in less than all directions, e.g., only along one axis, or to an insufficient extent can cause tensile restrictions, which can limit the thermoforming process, for example as shown in FIGS. 41C-41D.

As described herein, during thermoforming, the EVA sheet, e.g., EVA sheet 630, is placed onto and formed over the mold, e.g., mold 600, as shown in FIG. 42A. The depth of draw (or displacement from neutral) during the vacuum thermoforming process can affect the thickness of the formed mask components as shown in FIGS. 42B-42D. FIGS. 42B-42D illustrate forming of the seal component (e.g., seal 230). In FIGS. 42B-42D, the portions of the EVA sheet 630 above the horizontal indicator lines 601 are the usable portions (e.g., the portions of the component that remain and are used after trimming the perimeter of the component and the nasal aperture 234). The thickness of the mask components decreases as the draw depth increases. The mold can therefore be modified to achieve varying thicknesses in different sections of the mask components. In the embodiment of FIG. 42B, the draw depth is relatively small or shallow and uniform, and the seal components are therefore relatively thick and have a uniform thickness. In the embodiment of FIG. 42C, the draw depth is relatively small or shallow near the outer edge or perimeter of the component and relatively large or deep near the inner edge or perimeter of the component (around the nasal aperture 234). The seal component is therefore relatively thick on or near the outer edge and relatively thin on or near the inner edge. In the embodiment of FIG. 42D, the draw depth is relatively large or deep near both the outer and inner edges or perimeters. The seal component therefore is relatively thin and has a uniform or generally uniform thickness. In some embodiments, sharp corners in the mask components can cause creasing of the EVA foam during vacuum thermoforming. It may therefore be beneficial to avoid sharp corners in the mold.

In some embodiments, the housing and seal can be integrally formed. This can reduce manufacturing time and costs and the amount of material used. For example, the seal and housing can be formed from a single sheet of foam as shown in FIGS. 98-99. In this embodiment, the seal 1430 and housing 1420 are joined along their lower edges by a living hinge 1450. The seal 1430 includes a sealing surface 1432 surrounding an aperture 1435 that receives the nose and/or mouth of the user in use and retention arms 1334, for example, similar to any of the embodiments of retention arms shown and described herein. The housing 1420 can include a support wall 1424. The housing 1420 can include an inlet aperture 1425 to receive a supply of gases, for example, via a gas supply conduit or a swivel or elbow that can be coupled to a gas supply conduit.

To form the integral seal 1430 and housing 1420, a sheet of foam, e.g., EVA foam, can be thermoformed or vacuum formed and cut to shape before or after thermoforming or vacuum forming. The thermoforming or vacuum forming process can include a pre-stretching process, which can help allow formation of undercut geometries, such as the retention arms 1434, sealing surface 1432, and/or support wall 1424. The elasticity of the foam can allow undercut geometries to be stretched to be removed from the mold tool. The living hinge 1450 can be formed to have a thickness, e.g., varying thickness, that allows the living hinge 1450 to bend relatively easily to allow the housing 1420 and seal 1430 to be folded relative to each other to form the final cushion module 1414.

Figure 102:
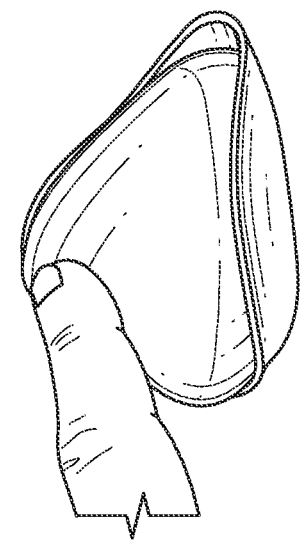
FIG. 102 illustrates the cushion module of FIG. 100 in a folded or coupled configuration.
Figure 101:
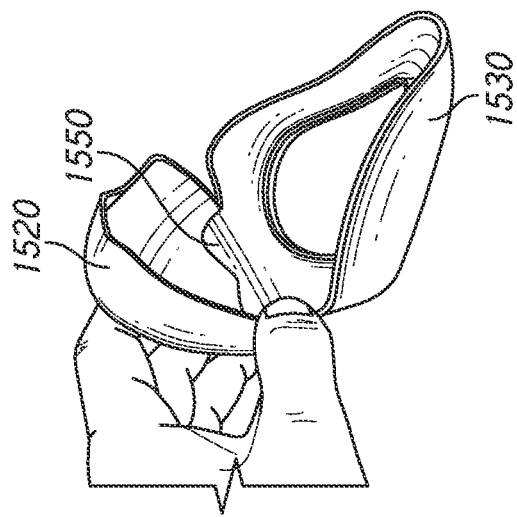
FIG. 101 illustrates the cushion module of FIG. 100 as the seal and housing are folded relative to each other.
Figure 100:
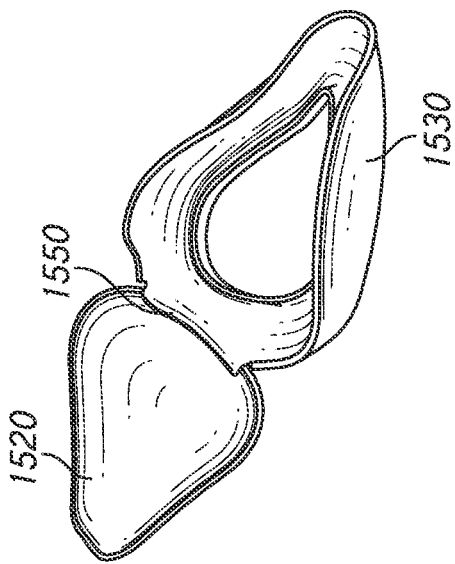
FIG. 100 illustrates an example embodiment of a cushion module including a seal and housing coupled via a living hinge in an expanded configuration.

In some alternative embodiments, a seal 1530 and housing 1520 can be formed separately and then joined together along their lower edges by a living hinge 1550, as shown in FIGS. 100-102. Similar to the living hinge 1450 of FIGS. 98-99, the living hinge 1550 can be formed to have a thickness, e.g., varying thickness, that allows the living hinge 1550 to bend relatively easily to allow the housing 1520 and seal 1530 to be folded relative to each other, as shown in FIGS. 101-102, to form the final cushion module. The living hinge 1550 can be formed by a tab that extends from a lower edge of the seal 1530 and that is coupled, e.g., welded or glued, to an internal lower surface of the housing 1520.

Figure 44B:
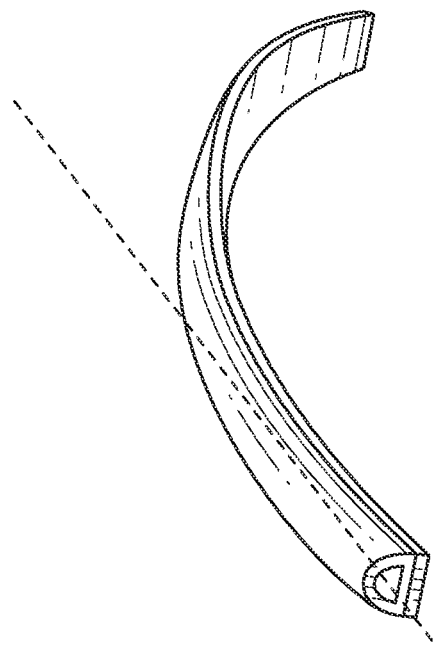
FIGS. 44A and 44B illustrate bending of the headgear component of FIG. 43A to form various shapes.
Figure 44A:
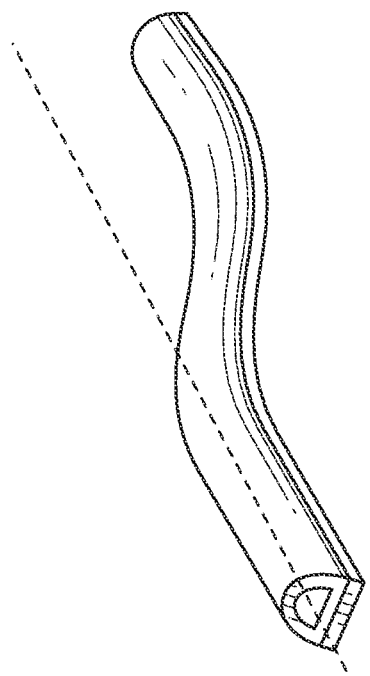

FIGS. 43A-44B illustrate a method of manufacturing headgear components 660 including an air conduit, for example, the top strap 462 and side straps 466 of the mask 410 and/or the top strap 562 of the mask 510. As shown, the headgear components 660 can include a hollow D-shaped EVA foam extrusion 662, a rigid strip 664 made of, for example, rigid plastic, and a textile covering 666. The rigid strip 664 is covered, e.g., permanently covered, with the textile covering 666. The textile covered rigid strip 664 is then connected, e.g., permanently connected, to the EVA foam extrusion 662. The headgear component 660 can then be formed into a desired shape, for example, a curved shape to correspond to the contours of the user's head. To shape the headgear component 660, a D-shaped rod is inserted into the foam extrusion 662 to hold the foam extrusion 662 open. The headgear component 660 can then be bent or formed into the desired shape and heated. The headgear component 660 can be shaped by bending the component 660 laterally and vertically about its longitudinal axis as shown in FIGS. 44A and 44B, respectively. Once cooled, the rod can be removed and the foam extrusion 662 and textile covered strip 664 will retain the formed shape as well as a constant or substantially constant cross-sectional area along the length of the component 660. In use, air flows through the hollow EVA foam extrusion 662 or through an air conduit disposed within the foam extrusion 662. The rigid strip 664 provides support to the headgear component 660. The textile covering 666 advantageously allows the patient-contacting surface of the headgear component 660 to be soft, comfortable, and/or warm to the user.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Certain terminology may have been used for the purpose of reference only, and thus are not intended to be limiting. For example, terms such as "above" and "below" may refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. Recitations of quantities, dimensions, sizes, formulations, parameters, shapes and other characteristics should also be construed as if the term "substantially" precedes the quantity, dimension, size, formulation, parameter, shape or other characteristic. Language of degree used herein, such as the terms "about," "approximately," "generally," and "substantially" as used herein represent a value, amount, or characteristic close to the stated value, amount, or characteristic that still performs a desired function or achieves a desired result and/or mean that quantities, dimensions, sizes, formulations, parameters, shapes and other characteristics need not be exact, but may be approximated and/or larger or smaller, as desired, reflecting acceptable tolerances, conversion factors, rounding off, measurement error, measurement accuracy limitations, and the like and other factors known to those of skill in the art. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A cushion module for a respiratory mask, the cushion module comprising:
    a housing comprising thermoformed foam; and
    a seal comprising thermoformed foam and coupled to the housing in use, the seal comprising a retention portion configured to removably retain the housing in engagement with the seal to form a breathing chamber;
    wherein the retention portion comprises a pair of arms, each of the pair of arms extending forwardly and inwardly from a lateral side of the seal; and
    wherein the housing comprises an inlet aperture, each of the pair of arms comprises an aperture proximate a free end of the arm, and the apertures of the pair of arms are configured to align with the inlet aperture when the seal and the housing are coupled.

2. The cushion module of claim 1, wherein the retention portion is configured to overlap at least a portion of the housing when the seal and the housing are coupled.

3. The cushion module of claim 1, wherein the retention portion is inwardly concave relative to the cushion module.

4. The cushion module of claim 1, wherein the pair of arms are configured to overlap each other.

5. The cushion module of claim 1, wherein a bushing, swivel, elbow, or air supply conduit extends through the apertures in the pair of arms and the inlet aperture to secure the arms relative to the housing.

6. The cushion module of claim 1, wherein the retention portion comprises a belt extending from a first lateral side of the seal to an opposing second lateral side of the seal.

7. The cushion module of claim 6, wherein the belt is tethered to a lower portion of the seal.

8. The cushion module of claim 1, wherein the retention portion comprises a pair of opposing arms extending from upper lateral sides of the seal.

9. The cushion module of claim 8, wherein the pair of opposing arms are substantially triangular.

10. The cushion module of claim 1, further comprising a retention cover coupled to the housing and configured to overlap at least a portion of the retention portion of the seal.

11. The cushion module of claim 10, wherein the retention cover comprises thermoformed foam.

12. The cushion module of claim 10, wherein the retention cover is coupled to the housing by a bushing.

13. The cushion module of claim 1, wherein the housing and the seal are formed from a single sheet of thermoformed foam.

14. The cushion module of claim 13, wherein the seal and the housing are joined by a living hinge.

\* \* \* \* \*